US008509867B2

(12) United States Patent
Workman et al.

(10) Patent No.: US 8,509,867 B2
(45) Date of Patent: *Aug. 13, 2013

(54) NON-INVASIVE MEASUREMENT OF ANALYTES

(75) Inventors: Jerome J. Workman, Madison, WI (US); Christopher R. Lambert, Hudson, MA (US); Robert L. Coleman, Olive Hill, KY (US)

(73) Assignee: Cercacor Laboratories, Inc., Irvine, CA (US)

( * ) Notice: Subject to any disclaimer, the term of this patent is extended or adjusted under 35 U.S.C. 154(b) by 886 days.

This patent is subject to a terminal disclaimer.

(21) Appl. No.: 11/349,731

(22) Filed: Feb. 7, 2006

(65) Prior Publication Data

US 2007/0020181 A1    Jan. 25, 2007

Related U.S. Application Data

(63) Continuation of application No. 11/153,263, filed on Jun. 15, 2005, now abandoned, which is a continuation of application No. 10/952,538, filed on Sep. 27, 2004, now abandoned, which is a continuation of application No. 10/712,669, filed on Nov. 12, 2003, now abandoned, which is a continuation-in-part of application No. 10/617,915, filed on Jul. 10, 2003, now abandoned, which is a continuation-in-part of application No. 10/616,533, filed on Jul. 9, 2003, now abandoned.

(60) Provisional application No. 60/425,488, filed on Nov. 12, 2002, provisional application No. 60/438,837, filed on Jan. 9, 2003, provisional application No. 60/439,395, filed on Jan. 10, 2003, provisional application No. 60/447,603, filed on Feb. 13, 2003, provisional application No. 60/516,352, filed on Oct. 31, 2003.

(51) Int. Cl.
*A61B 5/145* (2006.01)
*A61B 5/1455* (2006.01)

(52) U.S. Cl.
USPC ......... 600/316; 600/306; 600/310; 600/322; 600/329; 600/365; 600/473; 600/476; 436/63; 436/95; 436/164; 436/172

(58) Field of Classification Search
None
See application file for complete search history.

(56) References Cited

U.S. PATENT DOCUMENTS

| | | | |
|---|---|---|---|
| H227 H * | 3/1987 | Tracy et al. | 149/84 |
| 5,362,628 A * | 11/1994 | Haugland et al. | 435/18 |
| 5,391,250 A | 2/1995 | Cheney, II et al. | |
| 5,568,806 A | 10/1996 | Cheney, II et al. | |
| 5,586,553 A | 12/1996 | Halili et al. | |
| 5,605,152 A | 2/1997 | Slate et al. | |
| 5,777,060 A | 7/1998 | Van Antwerp | |
| 5,786,439 A | 7/1998 | Van Antwerp et al. | |
| 5,882,494 A | 3/1999 | Van Antwerp | |
| 5,954,643 A | 9/1999 | Van Antwerp et al. | |
| 5,972,199 A | 10/1999 | Heller et al. | |
| 6,002,954 A | 12/1999 | Van Antwerp et al. | |
| 6,011,984 A | 1/2000 | Van Antwerp et al. | |
| 6,040,194 A | 3/2000 | Chick et al. | |
| 6,190,315 B1 | 2/2001 | Kost et al. | |
| 6,240,306 B1 * | 5/2001 | Rohrscheib et al. | 600/316 |
| 6,304,766 B1 | 10/2001 | Colvin, Jr. | |
| 6,319,540 B1 | 11/2001 | Van Antwerp et al. | |
| 6,330,464 B1 | 12/2001 | Colvin, Jr. et al. | |
| 6,344,360 B1 | 2/2002 | Colvin et al. | |
| 6,360,888 B1 | 3/2002 | Melver et al. | |
| 6,368,274 B1 | 4/2002 | Van Antwerp et al. | |
| 6,377,721 B1 | 4/2002 | Walt et al. | |
| 6,387,059 B1 | 5/2002 | Marchitto et al. | |
| 6,400,974 B1 | 6/2002 | Lesho | |
| 6,462,162 B2 | 10/2002 | Van Antwerp et al. | |
| 6,477,395 B2 | 11/2002 | Schulman et al. | |
| 6,484,045 B1 | 11/2002 | Holker et al. | |
| 6,485,703 B1 * | 11/2002 | Cote et al. | 424/9.1 |
| 6,505,059 B1 | 1/2003 | Kollias et al. | |
| 6,512,939 B1 | 1/2003 | Colvin et al. | |
| 6,544,193 B2 | 4/2003 | Abreu | |
| 6,558,320 B1 | 5/2003 | Causey et al. | |
| 6,642,015 B2 | 11/2003 | Vachon et al. | |
| 6,663,615 B1 | 12/2003 | Madou et al. | |

(Continued)

FOREIGN PATENT DOCUMENTS

WO    WO 97/19188       5/1997
WO    WO 0014515 A1 *   3/2000

OTHER PUBLICATIONS

Connor, JA. Digital imaging of free calcium changes and of spatial gradients in growing processes in single, mammalian central nervous system cells. Proc. Natl. Acad. Sci. USA. Aug. 1986. 83: 6179-6183.*
Wachtler J et al. Glucose availability alters ischaemia-induced changes in intracellular pH and calcium of isolated rat spinal roots. Brain Research. 1996. 725: 30-36.*
International Search Report in corresponding International application No. PCT/US03/36366 mailed Jan. 6, 2005, 3 pp.
Koschinsky et al., Sensors for glucose monitoring: technical and clinical aspects, Diabetes Metab Res Rev, 2001, 17:113-123.

*Primary Examiner* — Allison Ford
*Assistant Examiner* — Susan E Fernandez
(74) *Attorney, Agent, or Firm* — Knobbe Martens Olson & Bear LLP

(57) ABSTRACT

This invention provides devices, compositions and methods for determining the concentration of one or more metabolites or analytes in a biological sample, including cells, tissues, organs, organisms, and biological fluids. In particular, this invention provides materials, apparatuses, and methods for several non-invasive techniques for the determination of in vivo blood glucose concentration levels based upon the in vivo measurement of one or more biologically active molecules found in skin.

33 Claims, 41 Drawing Sheets

(56) References Cited

U.S. PATENT DOCUMENTS

| | | |
|---|---|---|
| 6,673,625 B2 | 1/2004 | Satcher, Jr. et al. |
| 6,682,938 B1 | 1/2004 | Satcher, Jr. et al. |
| 6,711,423 B2 | 3/2004 | Colvin |
| 6,750,311 B1 | 6/2004 | Van Antwerp et al. |
| 6,766,183 B2 | 7/2004 | Walsh et al. |
| 6,770,729 B2 | 8/2004 | Van Antwerp |
| 6,784,274 B2 | 8/2004 | Van Antwerp et al. |
| 6,794,195 B2 | 9/2004 | Colvin, Jr. |
| 6,800,451 B2 | 10/2004 | Daniloff et al. |
| 6,804,544 B2 | 10/2004 | Van Antwerp et al. |
| 6,806,089 B1 * | 10/2004 | Lakowicz et al. ............ 436/68 |
| 6,809,653 B1 | 10/2004 | Mann et al. |
| 6,895,263 B2 | 5/2005 | Shin et al. |
| 6,927,246 B2 | 8/2005 | Noronha et al. |
| 6,940,590 B2 | 9/2005 | Colvin, Jr. et al. |
| 6,997,907 B2 | 2/2006 | Safabash et al. |
| 7,003,336 B2 | 2/2006 | Holker et al. |
| 7,016,714 B2 | 3/2006 | Colvin, Jr. |
| 7,022,072 B2 | 4/2006 | Fox et al. |
| 7,045,361 B2 | 5/2006 | Heiss et al. |
| 7,060,503 B2 | 6/2006 | Colvin, Jr. |
| 7,078,554 B2 | 7/2006 | Daniloff et al. |
| 7,135,342 B2 | 11/2006 | Colvin, Jr. et al. |
| 7,157,723 B2 | 1/2007 | Colvin et al. |
| 7,166,074 B2 | 1/2007 | Reghabi et al. |
| 7,190,445 B2 | 3/2007 | Colvin, Jr. et al. |
| 7,227,156 B2 | 6/2007 | Colvin, Jr. et al. |
| 7,247,138 B2 | 7/2007 | Reghabi et al. |
| 7,289,836 B2 | 10/2007 | Colvin, Jr. |
| 7,405,387 B2 | 7/2008 | Colvin, Jr. et al. |
| 7,625,951 B2 | 12/2009 | Daunert et al. |
| 2001/0008766 A1 | 7/2001 | Daunert et al. |
| 2002/0043651 A1 | 4/2002 | Darrow et al. |
| 2002/0068295 A1 | 6/2002 | Madou et al. |
| 2002/0119711 A1 | 8/2002 | Van Antwerp et al. |
| 2002/0123675 A1 | 9/2002 | Trautman et al. |
| 2004/0206916 A1 | 10/2004 | Colvin, Jr. et al. |
| 2006/0281185 A1 | 12/2006 | Colvin, Jr. |
| 2007/0059210 A1 | 3/2007 | Colvin, Jr. et al. |
| 2008/0064944 A1 | 3/2008 | Van Antwerp et al. |
| 2008/0108885 A1 | 5/2008 | Colvin, Jr. |
| 2009/0039286 A1 | 2/2009 | Colvin, Jr. et al. |

* cited by examiner

Fingertip

SMMRs

Stratum corneum
Stratum granulosum
Stratum germinativum

Dermis

Capillary fields extending into the dermal papillae from subcutaneous arteries and veins

* DR is measured diffuse reflection

FIG. 10A
FIG. 10B
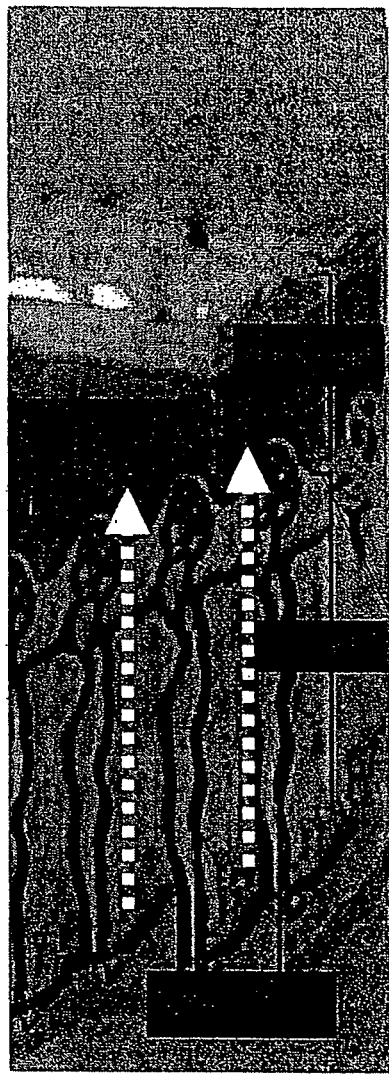
Human skin
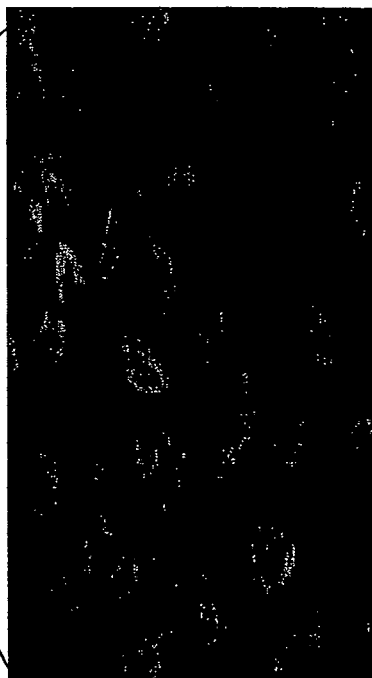
Human keratinocytes

Scheme 2. Overview of metabolic pathways for glucose in epidermis

Scheme 3. Structure of generic pH sensitive dye for specific action as a lactate/H$^+$ SMMR Scheme 4. *In Vivo* Calibration Issues

*Detectable Analytes (direct or indirect)

FRUCTOSE GLYCOLYSIS

GALACTOSE GLYCOLYSIS

*uridine diphosphate (UDP)

SMMR Mechanisms of Signal 1.0 Enhancement of Signal-to-noise of native autofluorescence 1.1 Energy Transfer from NADH, NAD(P)H, or FAD to Reporters (boosts signal by 5 to 50) indicating redox transfer coenzyme activity within cells and tissues 1.2 Redox potential Reporters indicates number of mitochondrial transmembrane redox potential events 2.0 Enhancement of Specific Metabolite and Precursor Signals 2.1 Lactate Reporters indicate lactate formation from anaerobic glycolysis activity 2.2 $Ca^{2+}$ Reporters indicate available ATP and ion pump transport activity fueled by glycolytic activity 3.0 Direct Glucose Reporters indicating quantitative levels of d-glucose 3.1 Protein-labeled fluorophores 3.2 proteins with a photooxidizable cofactor (such as FAD) to observe $^3FAD^*$

FIG. 28

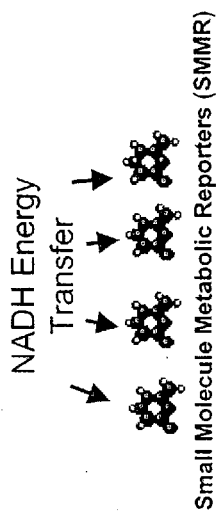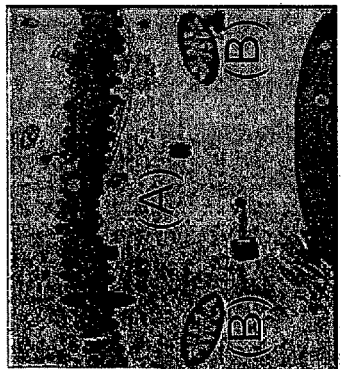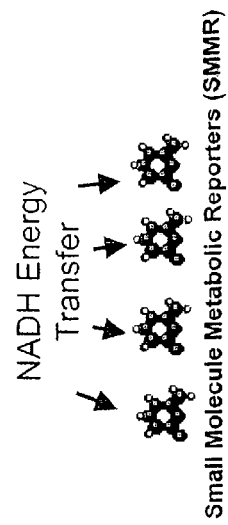
Energy Transfer Reporters
Glycolysis within the cell Cytosol (A)
Glucose + 2 $P_i$ + 2ADP 2$NAD^+$ → 2Pyruvate + 2 NADH + 2 ATP + 2$H^+$ + 2$H_2O$
Within the Mitochondria (B)
$NAD^+$ + Pyruvate + CoA → Acetyl CoA + $CO_2$ + NADH
FIG. 29

Redox Potential Reporters

In the Mitochondria $NAD^+ + Pyruvate + CoA \rightarrow Acetyl\ CoA + CO_2 + NADH + H^+$ Increase in glucose concentration increases the mitochondrial membrane potential causing more small molecule metabolic reporter (SMMR) units to attach to the membrane. This causes fluorescence quenching proportional to changes in glucose concentration

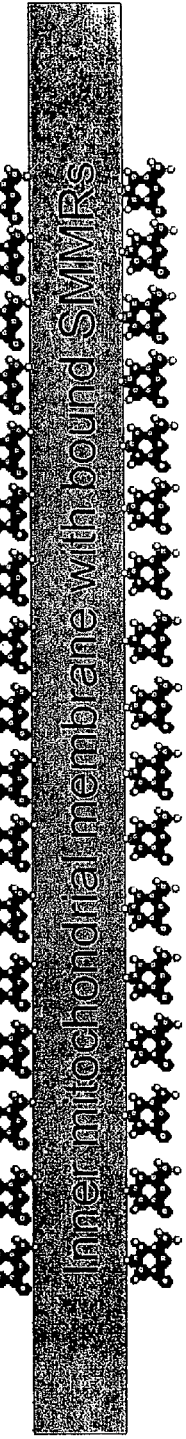

FIG. 30

Lactate Reporters

Anaerobic Glycolysis

Glucose + $2P_i$ + 2ADP → 2 lactate + 2ATP + $2H_2O$

Increase in glucose concentration increases the lactate formation in a 2:1 ratio. A small molecule metabolic reporter (SMMR) is used to detect pH changes caused by lactate concentration. The pH changes are directly related to glucose concentration pH change reduces FL of SMMRs

Ca²⁺ Reporters

Ca²⁺ and ATPase

Cell signaling is accomplished using ions such as $Ca^{2+}$. When the cell performs a signaling action $Ca^{2+}$ is released from ion storage into the cytosol where it triggers cellular activities. A small molecule metabolic reporter (SMMR) is used to detect $Ca^{2+}$ changes caused by changes in ion concentration within the cytosol. The $Ca^{2+}$ concentration changes are directly related to healthy cell function. After signaling the $Ca^{2+}$ is pumped back into storage using ATPase synthesized from Available ATP. Each molecule of ATP pumps 2 $Ca^{2+}$. If the ion pumps are not working due to respiratory stress the pumps are incapacitated. The ion concentrations equilibrate by diffusion since the pumps are incapacitated. The ion concentration gradients are maintained by ATP regulated pumps.

$Ca^{2+}$ changes increase FL of SMMRs

FIG. 32

O₂ Reporters

Aerobic Respiration

Glucose + 6$O_2$ +36 ADP +36$P_i$ → 6$CO_2$ + 6$H_2O$ +36 ATP + Heat

Increase in molecular oxygen indicates a favorable environment for aerobic respiration. A small molecule metabolic reporter (SMMR) is used to detect $O_2$ changes in the cellular environment. The $O_2$ changes are directly related to ability to manufacture ATP.

$O_2$ changes increase FL of SMMRs

FIG. 33

SMMR has been used to establish analytical methods for measuring each glucose pathway for a variety of cell types

Method for adding SMMR to peripheral epithelial cells in tissues and organs
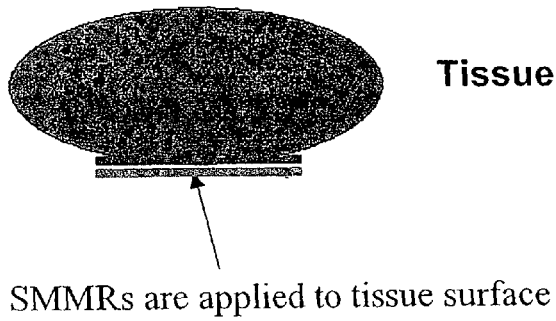
A. SMMRs are applied to tissue surface
B. SMMRs are transported for up to 10-300 microns into the top of the tissue using passive or active transport
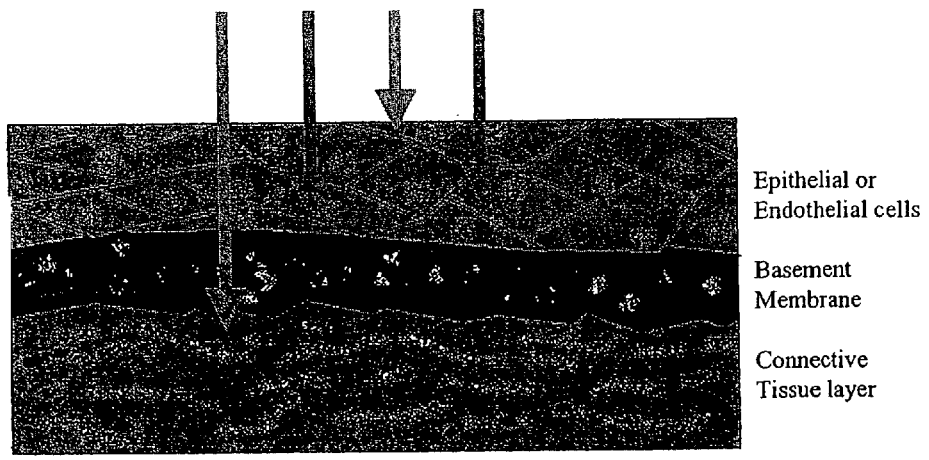
Outer (or inner) membrane of tissues and organs
FIG. 36

NON-INVASIVE MEASUREMENT OF ANALYTES

RELATED APPLICATIONS

This application is a continuation of U.S. Ser. No. 11/153,263, filed on Jul. 15, 2005, which is a continuation of U.S. Ser. No. 10/952,538, filed Sep. 27, 2004, which is a continuation of U.S. Ser. No. 10/712,669, filed on Nov. 12, 2003, which is a continuation in part U.S. Ser. No. 10/617,915, filed on Jul. 10, 2003, which is a continuation in part of U.S. Ser. No. 10/616,533, filed on Jul. 9, 2003, which claims priority to U.S. provisional patent application Ser. No. 60/425,488, filed Nov. 12, 2002, and U.S. Ser. No. 10/712,669 also claims priority to Ser. No. 60/438,837, filed Jan. 9, 2003, Ser. No. 60/439,395, filed Jan. 10, 2003, Ser. No. 60/447,603, filed Feb. 3, 2003, and Ser. No. 60/516,352 filed on Oct. 31, 2003, each of which is incorporated by reference in its entirety.

FIELD OF THE INVENTION

This invention provides devices, compositions and methods for determining the concentration of one or more metabolites or analytes in a biological sample, including cells, tissues, organs, organisms, and biological fluids. In particular, this invention provides materials, apparatuses, and methods for several non-invasive techniques for the determination of in vivo blood glucose concentration levels based upon the in vivo measurement of one or more biologically active molecules found in skin.

BACKGROUND OF THE INVENTION

Identifying and understanding the risk factors associated with diabetes is invaluable for the development and evaluation of effective intervention strategies.

Lacking normal regulatory mechanisms, diabetics are encouraged to strive for optimal control through a modulated life style approach that focuses on dietary control, exercise, and glucose self-testing with the timely administration of insulin or oral hypoglycemic medications. Invasive forms of self-testing are painful and fraught with a multitude of psychosocial hurdles, and are resisted by most diabetics. Alternatives to the currently available invasive blood glucose testing are highly desirable.

Conventional approaches to non-invasive alternatives seek to reduce or eliminate the skin trauma, pain, and blood waste associated with traditional invasive glucose monitoring technologies. In general, though never effectively demonstrated prior to this invention, noninvasive optical blood glucose monitoring requires no bodily fluid samples be withdrawn from tissue and involves external irradiation with electromagnetic radiation and measurement of the resulting optical flux (e.g., fluorescence or diffuse reflectance). In theory, but not in practice, glucose levels would be derived from the spectral information following comparison to reference spectra for glucose and background interferants, reference calibrants, and/or application of advanced signal processing mathematical algorithms.

Radiation-based technologies, which are often referred to as potential candidates for solving the non-invasive glucose problem, have included variations of sampling and data processing methods including: 1) mid-infrared (MIR) spectroscopy, 2) near-infrared radiation (NIR) spectroscopy, 3) radio wave impedance, 4) autofluorescence and white light scattering, and 5) Raman spectroscopy. Each of these methods uses optical sensors and relies on the premise that the absorption or fluorescence pattern of electromagnetic radiation can be quantitatively related to a change in blood glucose concentration. However, other endogenous substances including, but not limited to, water, lipids, proteins, and hemoglobin are known to absorb energy, particularly infrared light and can easily obscure the relatively weak glucose signal.

Other approaches to non-invasive glucose measurements are based on microvascular changes in the retina, acoustical impedance, nuclear magnetic resonance (NMR) spectroscopy and optical hydrogels that quantify glucose levels in tear fluid. While putatively non-invasive, these technologies have yet to be demonstrated as effective in clinical testing.

Nearly noninvasive techniques tend to rely on interstitial fluid extraction from skin. This can be accomplished using permeability enhancers, sweat inducers, and/or suction devices with or without the application of electrical current. One device recently approved by the FDA relies on reverse iontophoresis, utilizing an electrical current applied to the skin. The current pulls out salt, which carries water, which, in turn, carries glucose. The glucose concentration of this recovered fluid is measured and is proportional to that of blood. In keeping with its nearly noninvasive description, this technology is commonly associated with some discomfort and requires at least twice daily calibrations against conventional blood glucose measurements (e.g. invasive lancing).

Other nearly noninvasive blood glucose monitoring techniques similarly involve transcutaneous harvesting for interstitial fluid measurement. Other technologies for disrupting the skin barrier to obtain interstitial fluid include: 1) dissolution with chemicals; 2) microporation with a laser; 3) penetration with a thin needle; and/or 4) suction with a pump. Minimally invasive blood glucose monitoring can also involve the insertion of an indwelling glucose monitor under the skin to measure the interstitial fluid glucose concentration. These monitors typically rely on optical or enzymatic sensors. Although technologically innovative, these in situ sensors have had limited success. Implantable glucose oxidase ("GO") sensors have been limited by local factors causing unstable signal output, whereas optical sensors must overcome signal obfuscation by blood constituents as well as interference by substances with absorption spectra similar to glucose. Moreover, inflammation associated with subcutaneous monitoring may contribute to systematic errors requiring repositioning, recalibration or replacement, and more research is needed to evaluate the effects of variable local inflammation at the sensor implantation site on glucose concentration and transit time.

Interstitial fluid glucose concentrations have previously been shown to be similar to simultaneously measured fixed or fluctuating blood glucose concentrations. See, e.g., Bantle et al., *Journal of Laboratory and Clinical Medicine* 130:436-441, 1997; Sternberg et al., *Diabetes Care* 18:1266-1269, 1995. Such studies helped validate noninvasive/minimally invasive technologies for blood glucose monitoring, insofar as many of these technologies measure glucose in blood as well as interstitial fluid.

A noninvasive glucose monitor that is portable, simple and rapid to use, which provides accurate clinical information is desirable. In particular, the ability to derive first and second order information in real-time for dynamic glucose metabolism, such as the direction and rate of change of bioavailable glucose distributed within the blood and interstitial fluid space, would be extremely important for continuous and discrete glucose monitoring.

SUMMARY OF THE INVENTION

The methods and compositions of the present invention effectively determine the glucose concentration in blood for a living organism by non-invasive, in vivo measurement of the glucose level in skin by means of fluorescence measurements of metabolic indicators/reporters of glucose metabolism. Disclosed are dyes used as metabolic indicators that allow for specific in vivo monitoring of metabolites, which are used as indicators of metabolic activity. Dyes characterized by this invention are referred to herein as a small molecule metabolite reporters ("SMMRs").

This invention also provides for fluorescence measurements of extracellular and intracellular reporter molecules placed into the cytosol, nucleus, or organelles of cells within intact, living, tissue that track the concentration of blood glucose in an organism. When any one of a series of metabolites is measured using this technique, the molar concentration of blood glucose can be calculated. Direct or indirect fluorescence measurements of glucose using one or more of the following measurements is described: pH (as lactate/$H^+$), membrane reduction-oxidation electric potential, NAD(P)H (nicotinamide adenine dinucleotide (phosphate), reduced form) for energy transfer, $FAD^+$ (flavin adenine dinucleotide, oxidized form) for energy transfer, ATP/ADP ratio, $Ca^{2+}$-pumping rate, $Mg^{2+}$-pumping rate, $Na^+$-pumping rate, $K^+$-pumping rate, and vital mitochondrial membrane stains/dyes/molecules fluorescence response. These analytes, measured in skin using the techniques taught herein, are used to provide a complete picture of epidermal skin glycolytic metabolism where local epidermal analyte (glucose) quantities are proportional to the concentration of glucose in systemic blood, specifically the capillary fields within the papillary layer of the dermis (corium). Temperature and/or nitric oxide measurement may also be combined with the above measurements for better calibration and determination of glucose concentrations.

The invention further provides sensor compositions that are applied to at least one surface of living tissue, organs, interstitial fluid, and whole organisms and transported into the tissue at an effective concentration. The sensor composition can include at least one small molecule metabolic reporter (SMMR) at an effective concentration such that when the at least one SMMR is brought in contact with one or more specific metabolites or analytes, a change in fluorescence or absorption occurs, thereby allowing quantification of the change in fluorescence or absorption.

For example, the at least one small molecule metabolic reporter used in the sensor composition can be a fluorophore, a protein labeled fluorophore, a protein comprising a photo-oxidizable cofactor, a protein comprising another intercalated fluorophore; a mitochondrial vital stain or dye, a dye exhibiting at least one of a redox potential, a membrane localizing dye, a dye with energy transfer properties, a pH indicating dye; a coumarin dye, a derivative of a coumarin dye, an anthraquinone dye, a cyanine dye, an azo dye, a xanthene dye, an arylmethine dye, a pyrene derivative dye, or a ruthenium bipyridyl complex dye.

Examples of suitable mitochondrial vital stains or dyes include, but are not limited to, a polycyclic aromatic hydrocarbon dye, such as, for example, rhodamine 123; di-4-ANEPPS; di-8-ANEPPS; $DiBAC_4(3)$; RH421; tetramethylrhodamine ethyl ester, perchlorate; tetramethylrhodamine methyl ester, perchlorate; 2-(4-(dimethylamino)styryl)-N-ethylpyridinium iodide; 3,3'-dihexyloxacarbocyanine; 5,5',6,6'-tetrachloro-1,1',3,3'-tetraethyl-benzimidazolylcarbocyanine chloride; 5,5',6,6'-tetrachloro-1,1',3,3'-tetraethyl-benzimidazolylcarbocyanine iodide; nonylacridine orange; dihydrorhodamine 123; dihydrorhodamine 123, dihydrochloride salt; xanthene; 2',7'-bis-(2-carboxyethyl)-5-(and -6)-carboxyfluorescein; benzenedicarboxylic acid; 2(or 4)-[10-(dimethylamino)-3-oxo-3-H-benzo[c]xanthene-7-yl]; and iodine dissolved in potassium iodide.

Examples of suitable protein labeled fluorophores include, but are not limited to, Glucose Oxidase-Labeled Fluorophore (GO-LF) and Glucose Oxidase-Intercalated Fluorophore (GO-IF). Examples of a suitable protein include a photooxidizable cofactor includes Glucose Oxidase (GOx) with a flavin adenine dinucleotide (FAD) in the triplet state (GOx-$^3FAD^*$).

The one or more specific metabolites or analytes to be detected in a surface of living tissue, organs, interstitial fluid, and whole organisms include, for example, glucose, lactate, $H^+$, $Ca^{2+}$, $Mg^{2+}$, $Na^+$, $K^+$, ATP, ADP, $P_i$, glycogen, pyruvate, NAD(P)+, NAD(P)H, FAD, $FADH_2$, and $O_2$.

The in vivo information obtained when the SMMR is brought in contact with the one or more metabolites or analytes can include, but is not limited to, assessment of metabolic function; diagnosis of metabolic disease state; monitoring and control of disease state; stress status of cells, tissues and organs; determination of vitality and viability of cells based on metabolic function; critical care monitoring; diagnosis and monitoring of cardiovascular diseases, autoimmune disorders, neurological disorders, degenerative diseases; determination of metabolic concentration; and cancer diagnosis, detection, staging and prognosis.

For example, the in vivo information obtained may provide detailed information on glucose metabolism, fructose metabolism and galactose metabolism; advanced-glycosolated end products; monitoring and control of diseases such as diabetes, cancer, stress and organ transplantation.

The sensor compositions used in these methods for monitoring the concentration of one or more metabolite(s) or analyte(s) can be formulated as, but are not limited to, emulsions, ointments, disposable gel film patches, reservoir devices, creams, paints, polar solvents, non-polar solvents, or any combination thereof.

Penetration of the sensor composition can be accomplished using an active transport technique or a passive transport technique, such as, for example, electroporation, laser poration, sonic poration, ultrasonic poration, iontophoresis, mechanical-poration, solvent transport, tattooing, wicking, microneedle or pressurized delivery. In addition, penetration of the sensor composition to the desired depth can be accomplished by combining the composition with various molecular size attachments.

Typically, the quantification of the change in fluorescence or absorption is monitored using fluorescence or absorption spectroscopy.

An effective concentration of the sensor composition is, for example, at least between 0.01 to 500 µg/ml, between 0.1 to 500 µg/ml, between 1.0 to 150 µg/ml, between 1 to 100 µg/ml, and between 10 to 100 µg/ml. The SMMR can be introduced in a low concentration in a range from 10 µM to 1000 µM and in a volume from 200 µL to 0.1 µL, respectively (e.g., introducing the SMMR at a concentration in the range of 200 µL of a 10 µM SMMR solution to 0.1 µl of a 1000 µM SMMR solution). One specific application of the sensor composition is, for example, a 5 µL volume of a 400 µM SMMR solution, or a 10 µL volume at 200 µM concentration.

The one or more metabolite(s) or analyte(s) can directly report on, and/or relate to, in vivo blood glucose levels. Suitable metabolites or analytes include any of the metabolites or analytes listed herein.

The SMMR may be chosen based on one or more properties selected from the group consisting of molecular size, charge, structure, pKa, solubility, polarity, and solvent system used to transport the one or more small molecule metabolic reporters to living tissue.

The invention also provides methods for identifying a small molecule metabolic reporter (SMMR). According to these methods, one or more metabolites required to characterize a selected metabolic pathway in a living system are delineated. A basic mechanism of action for the SMMR is determined. One or more wavelength choices for excitation and emission of the SMMR are selected by analysis of absorption and fluorescence measurements. A molecular structure to meet quantum efficiency and yield requirements is selected, as well as location, diffusion rate, and duration or lifetime of the SMMR within a tissue or organ layers, as well as toxicity requirements and limitations. Optionally, measured real-time metabolic conditions are related to disease state for diagnosis or patient care.

The invention also provides in vivo methods for determining the metabolic health and well-being in living organisms by applying at least one small molecule metabolic reporter (SMMR) to a surface of an organ for a predetermined period of time. The SMMR penetrates to a depth of about 10 μm to about 300 μm. A change in the fluorescence or absorption is measured based upon peripheral or epithelial tissue metabolite levels. The metabolite levels within peripheral or epithelial tissue are then correlated with cellular metabolite levels.

Also provided by this invention are in vivo methods for monitoring and controlling disease states that affect metabolic processes in living organisms. According to these methods, at least one small molecule metabolic reporter (SMMR) is applied to at least one surface of a living tissue, organs, and/or whole organisms for a predetermined period of time. The SMMR penetrates to a depth of about 10 μm to about 300 μm. A change in the fluorescence or absorption is monitored based upon peripheral or epithelial tissue metabolite levels. The metabolite levels within peripheral or epithelial tissue is then correlated with cellular metabolite levels.

For example, disease states may include diabetes, diabetes progression, aging, critical care states, organ transplantation, tissue and cell viability and vitality, cardiovascular disease, autoimmune disorders, neurological disorders, degenerative disease; and cancer diagnosis, detection, staging and prognosis.

Also provided are in vivo methods for monitoring the concentration of one or more metabolites or analytes. According to these methods, at least one small molecule metabolic reporter (SMMR) is applied to at least one surface of a living tissue, organs, and/or whole organisms for a predetermined period of time. The SMMRs then penetrate to a depth of about 10 μm, wherein the depth corresponds with the bottom of the dead stratum corneum layer, to about 175 μm, wherein the depth corresponds with the top of the dermal layer, into the epidermis. A change in the concentration of the one or more metabolites or analytes in a metabolic pathway is monitored by detecting changes in the at least one SMMR at one or more time points using an optical reader by detecting at least one wavelength above 350 nm.

The SMMR can include a mitochondrial vital stain or dye sensitive to membrane potential or chemical gradient. For example, the mitochondrial stain can be a polycyclic aromatic hydrocarbon dye, such as, for example, rhodamine 123; di-4-ANEPPS; di-8-ANEPPS; DiBAC$_4$(3); RH421; tetramethylrhodamine ethyl ester, perchlorate; tetramethylrhodamine methyl ester, perchlorate; 2-(4-(dimethylamino)styryl)-N-ethylpyridinium iodide; 3,3'-dihexyloxacarbocyanine; 5,5',6,6'-tetrachloro-1,1',3,3'-tetraethyl-benzimidazolylcarbocyanine chloride; 5,5',6,6'-tetrachloro-1,1',3,3'-tetraethyl-benzimidazolylcarbocyanine iodide; nonylacridine orange; dihydrorhodamine 123; dihydrorhodamine 123, dihydrochloride salt; xanthene; 2',7'-bis-(2-carboxyethyl)-5-(and -6)-carboxyfluorescein; benzenedicarboxylic acid; 2(or 4)-[10-(dimethylamino)-3-oxo-3-H-benzo[c]xanthene-7-yl]; and iodine dissolved in potassium iodide.

The SMMR can include a dye or stain that transfers energy from a molecule generated as a result of the oxidative metabolic pathway and that has a stoichiometric or highly correlated relationship with glucose concentration.

Alternatively, the SMMR includes a dye selected from the group consisting of: coumarin; derivatives of coumarin; anthraquinones; cyanine dyes; azo dyes; xanthene dyes; arylmethine dyes; pyrene derivatives; and ruthenium bipyridyl complexes.

The SMMR may be a protein labeled fluorophore. For example, Glucose Oxidase-Labeled Fluorophore (GO-LF) and Glucose Oxidase-Intercalated Fluorophore (GO-IF).

The SMMR may also be a protein comprising a photooxidizable cofactor, such as, for example Glucose Oxidase (GOx) with a flavin adenine dinucleotide (FAD) in the triplet state (GOx-$^3$FAD*).

The one or more metabolites or analytes that can be monitored can be one of glucose; lactate; hydrogen ion ($H^+$); calcium ion ($Ca^{2+}$) pumping rate; magnesium ion ($Mg^{2+}$) pumping rate; sodium ion ($Na^+$) pumping rate; potassium ion ($K^+$) pumping rate; adenosine triphosphate (ATP); adenosine diphosphate (ADP); the ratio of ATP to ADP; inorganic phosphate ($P_i$); glycogen; pyruvate; nicotinamide adenine dinucleotide phosphate, oxidized form (NAD(P)+); nicotinamide adenine dinucleotide phosphate, reduced form (NAD(P)H); flavin adenine dinucleotide, oxidized form (FAD); and flavin adenine dinucleotide, reduced form ($FADH_2$); and oxygen ($O_2$) utilization.

The SMMRs of the invention can be formulated as emulsions, ointments, disposable gel film patches, reservoir devices, creams, paints, polar solvents, non-polar solvents, or any combination thereof.

Penetration of the SMMR can be accomplished using an active transport technique or a passive transport technique, such as, for example, electroporation, laser poration, sonic poration, ultrasonic poration, iontophoresis, mechanical-poration, solvent transport, tattooing, wicking, microneedle or pressurized delivery. In addition, penetration of the sensor composition to the desired depth can be accomplished by combining the composition with various molecular size attachments.

The invention also provides in vivo methods for measuring metabolite levels by monitoring in a population of cells one or more relevant metabolites, parameters or analytes in at least one metabolic pathway, wherein the monitoring involves measuring the fluorescence spectrum emitted by at least one small molecule metabolic reporter (SMMR), wherein at least one fluorescence spectrum emitted by the SMMR is stoichiometrically related to the metabolite, parameter or analyte concentration in the population of cells, whereby analyzing the relatedness provides the in vivo metabolite level.

The population of cells can have a predominantly glycolytic metabolism, or alternatively, the population of cells can be induced to have a glycolytic metabolism. The population of cells in the skin can be located in the epidermis, which contains a dynamic, metabolically homogeneous, and homeostatic population of cells. For example, the population of cells having a glycolytic metabolism can include live keratinocytes. These live keratinocytes can be present in the epidermal layer of skin. In some cases, the live keratinocytes can be present in the skin at a depth, from the surface of the skin, of about 10 μm, which corresponds to the bottom of the dead stratum corneum layer, to about 175 μm, which corresponds to the top of the dermal layer.

The metabolic pathways monitored within the population of cells, according to these methods for measuring in vivo blood glucose levels through the skin, can be monitored by measuring a specific metabolite or analyte of the glycolytic pathway, wherein the specific metabolite or analyte has a known stoichiometric or highly correlated relationship with glucose concentration. The metabolic pathways can also be monitored within the population of cells by observing a physico-chemical parameter that is related to the glycolytic pathway, wherein the selected physico-chemical parameter has a stoichiometric or highly correlated relationship with glucose concentration.

For example, the relevant metabolites or analytes that are monitored in these methods for measuring in vivo blood glucose levels through the skin can be lactate; hydrogen ion ($H^+$); calcium ion ($Ca^{2+}$) pumping rate; magnesium ion ($Mg^{2+}$) pumping rate; sodium ion ($Na^+$) pumping rate; potassium ion ($K^+$) pumping rate; adenosine triphosphate (ATP); adenosine diphosphate (ADP); the ratio of ATP to ADP; inorganic phosphate ($P_i$); glycogen; pyruvate; nicotinamide adenine dinucleotide phosphate, oxidized form (NAD(P)+); nicotinamide adenine dinucleotide (phosphate), reduced form (NAD(P)H); flavin adenine dinucleotide, oxidized form (FAD); flavin adenine dinucleotide, reduced form ($FADH_2$); or oxygen ($O_2$) utilization.

The population of cells to be monitored in these methods for measuring in vivo blood glucose levels through the skin can have a predominantly oxidative metabolism, or alternatively, the population of cells can be induced to have a metabolism predominantly based on oxidative phosphorylation. The metabolic pathways monitored within the population of cells can be monitored by measuring a metabolite or analyte that is generated as a result of the oxidative metabolic pathway, wherein the specific metabolite or analyte has a stoichiometric or highly correlated relationship with glucose concentration. Alternatively, the metabolic pathways can be monitored within the population of cells by observing a physico-chemical parameter that is generated as a result of the oxidative metabolic pathway, wherein the physico-chemical parameter has a stoichiometric or highly correlated relationship with glucose concentration.

Also provided are noninvasive methods for monitoring in vivo blood glucose levels. According to these methods at least one small molecule metabolic reporter (SMMR) is applied to at least one surface of skin for a predetermined period of time causing penetration of the one or more SMMRs to a depth of about 10 μm, wherein the depth corresponds with the bottom of the dead stratum corneum layer, to about 175 μm, wherein the depth corresponds with the top of the dermal layer, into the epidermis. The one or more SMMRs come in contact with one or more metabolites or analytes and a change in the concentration of the one or more metabolites or analytes is monitored by detecting changes in the SMMRs using an optical reader. The change in the concentration of the one or more metabolites or analytes is then correlated with in vivo blood glucose levels.

The at least one small molecule metabolic reporter can be selected from the group consisting of a fluorophore, a protein labeled fluorophore, a protein comprising a photooxidizable cofactor, a protein comprising another intercalated fluorophore, a mitochondrial vital stain or dye, and a dye exhibiting one or more of a redox potential, a membrane localizing dye, a dye comprising energy transfer properties, a pH indicating dye, a coumarin dye, a derivative of a coumarin dye, an anthraquinone dye; a cyanine dye, an azo dye; a xanthene dye; an arylmethine dye; a pyrene derivative dye and a ruthenium bipyridyl complex dye.

The one or more specific metabolites can be selected from the group consisting of glucose, lactate, $H^+$, $Ca^{2+}$, $Mg^{2+}$, $Na^+$, $K^+$, ATP, ADP, $P_i$, glycogen, pyruvate, NAD(P)+, NAD(P)H, FAD, $FADH_2$, and $O_2$.

For example, when the SIR is a protein labeled fluorophore, Glucose Oxidase-Labeled Fluorophore (GO-LF) is used and the metabolite monitored is glucose.

Alternatively, the SMMR can be a protein comprising a photooxidizable cofactor such as Glucose Oxidase (GOx) with a flavin adenine dinucleotide (FAD) in the triplet state (GOx-$^3$FAD*).

The SMMRs used in these methods for monitoring in vivo blood glucose levels can include, for example, a mitochondrial stain sensitive to membrane potential or chemical gradient. Examples of suitable mitochondrial stains include a polycyclic aromatic hydrocarbon dye, such as, for example, rhodamine 123; di-4-ANEPPS; di-8-ANEPPS; $DiBAC_4(3)$; RH421; tetramethylrhodamine ethyl ester, perchlorate; tetramethylrhodamine methyl ester, perchlorate; 2-(4-(dimethylamino)styryl)-N-ethylpyridinium iodide; 3,3'-dihexyloxacarbocyanine; 5,5',6,6'-tetrachloro-1,1',3,3'-tetraethyl-benzimidazolylcarbocyanine chloride; 5,5',6,6'-tetrachloro-1,1',3,3'-tetraethyl-benzimidazolylcarbocyanine iodide; nonylacridine orange; dihydrorhodamine 123; dihydrorhodamine 123, dihydrochloride salt; xanthene; 2',7'-bis-(2-carboxyethyl)-5-(and -6)-carboxyfluorescein; benzenedicarboxylic acid, 2(or 4)-[10-(dimethylamino)-3-oxo-3-H-benzo[c]xanthene-7-yl]; and iodine dissolved in potassium iodide. Monitoring the change in the one or more metabolite or analyte concentrations can be accomplished by measuring at least one spectral emission at a wavelength above 350 nm.

Also included in the invention is a reagent strip for use in a glucose measuring instrument comprising a polymer strip and a known concentration of at least one small molecule metabolic reporter (SMMR), wherein when a sample of a biological fluid containing an amount of glucose is interacted with the reagent strip, a change in fluorescence or absorption of the one or more molecular sensor proteins occurs, and the change is measured by the glucose measuring instrument, thereby detecting the glucose concentration of the biological fluid.

The at least one SMMR can be selected from Glucose Oxidase-Labeled Fluorophore (GO-LF), Glucose Oxidase-Intercalated Fluorophore (GO-IF) and Glucose Oxidase (GOx) with a flavin adenine dinucleotide (FAD) in the triplet state (GOx-$^3$FAD*).

The change in fluorescence or absorption can be monitored using fluorescence or absorption spectroscopy. Those of ordinary skill in the art will recognize that any fluorescence or absorption spectroscopic techniques can be used in accordance with the invention.

Also provided is a reagent strip for use in calibrating a glucose measuring instrument comprising a polymer strip, a known concentration of at least one small molecule metabolic reporter (SMMR), and at least one sample containing a known concentration of glucose, wherein when the at least one sample is interacted with the reagent strip, a change in fluorescence or absorption of the one or more molecular sensor proteins occurs, wherein the change is measured by the glucose measuring instrument, thereby calibrating the instrument.

The at least one SMMR may be selected from the group consisting of Glucose Oxidase-Labeled Fluorophore (GO- LF) and Glucose Oxidase (GOx) with a flavin adenine dinucleotide (FAD) in the triplet state (GOx-$^3$FAD*).

The change in fluorescence or absorption can be monitored using fluorescence or absorption spectroscopy.

The invention also provides sensor systems that include a device having a component that transmits radiation to a material or tissue, a component that detects radiation emitted from a material or tissue, and a component to display the detection results, each component is operably linked. The sensor systems further include an applicator that delivers the sensor composition of the invention to the material or tissue. Typically, there is an air interface between the device and the material or tissue, wherein the air interface measures a resulting excitation radiation emitted from the irradiated sensor composition.

The device included in the sensor system can emit radiation at one or more wavelengths that have been chosen to specifically excite the SMMR mixture that is applied to the material or tissue. The sensor composition can include a reporter dye and a marker dye, or alternatively, a dye exhibiting a wavelength shift in absorption or fluorescence emission in the presence of a metabolite. The sensor composition can be present at a depth from the surface of the skin of about 10 μm to about 175 μm in the epidermis in a concentration that is effective for detection of one or more metabolites or analytes in a biological sample.

The sensor system can detect radiation at one or more wavelengths that have been chosen to specifically identify fluorescence emission that has been scattered back to the system from the sensor composition.

The invention also provides additional methods for determining in vivo blood glucose concentration. According to these methods, an instrument response measurement is performed on a calibration target, and the response data is recorded. At least one SMMR mixture is applied to the skin in a first, controlled area, such that the SMMR resides in the epidermal layer of the skin, and a second SMMR mixture is applied to the skin in a second controlled area. The second area is perturbed, such that one or more extreme changes that the mixture may undergo is achieved. A calibration measurement is performed on the perturbed area, and the calibration data is recorded. A background measurement is made on an area of skin that has no SMMR, and this background data is recorded. A measurement on the first area is performed by illuminating the first area with light, and at least one wavelength spectrum of light reflected back from the first area is detected. Further measurements on the first area are performed at wavelengths suitable for each SMMR present. At least one parameter from the response data is calculated to normalize the background data, calibration data and measurement data for the response of the spectrometer. At least one parameter from the background data is calculated to correct the calibration data and measurement data for emission, absorption and scattering properties of the tissue. At least one metabolite parameter from the calibration data is calculated to relate the measurement data to the blood glucose concentration, thereby determining in vivo blood glucose concentration. The one or more extreme changes can be, for example, a change in concentration of the metabolite or analyte between a zero or low measurable concentration and a saturation level or high measurable concentration.

The invention also provides methods of calculating blood glucose concentration. According to these methods, at least one background response and at least one autofluorescence tissue response and measured from a calibration target comprising an epidermal layer of skin. A first SMMR mixture is provided to a first skin location, and portions of the first SMMR mixture are transferred into the epidermal layer of the skin. A second SMMR mixture is provided to a second skin location, and at least one extreme change in the mixture is triggered and recorded. The extreme change can be, for example, a change in concentration of the analyte comprising a zero or low measurable concentration and a saturation level or high measurable concentration. These extremes are used to calibrate the sensor enabling it to measure a test sample accurately with a concentration between the extremes. See e.g., equations (13) through (21), as described herein. The first skin location is illuminated with a radiative emission, and a resulting wavelength spectrum reflected from the first skin location is detected. The illuminating and detecting can be repeated using at least one irradiation and wavelength spectrum associated with each SMMR provided. At least one physico-chemical parameter that is related to the glycolytic pathway is detected. Preferably, the physico-chemical parameter has a stoichiometric or highly correlated relationship with glucose concentration, which is used in determining the blood glucose concentration. The sensor system can include a bloodless calibration procedure such as, for example, the procedure(s) outlined in equations 13, 16, 17, 18, 19, 20 or 21 set forth herein.

The invention also provides methods for determining the concentration of at least one metabolite or analyte in skin tissue. According to these methods, a small molecule metabolite reporter (SMMR) agent is administered to the skin tissue. The SMMR agent penetrates to a region of the skin at a depth between the dermis and the epidermis, wherein the depth from the surface of the skin is from about 10 μm to about 175 μm. The SMMR agent is irradiated with a source of electromagnetic radiation, and the fluorescence spectra emitted from the SMMR agent are detected. The emitted fluorescence spectra are then analyzed, which results in a determination of the concentration of the metabolite or analyte. Measuring the fluorescence spectra according to these methods can include a bloodless calibration procedure, such as, the procedure(s) outlined in equations 13, 16, 17, 18, 19, 20 and 21 set forth herein.

Unless otherwise defined, all technical and scientific terms used herein have the same meanings as commonly understood by one of ordinary skill in the art to which the invention belongs. Specific technical and scientific terms used herein have the following meanings:

As used herein and in the claims, the singular forms "a", "and" and "the" include plural referents unless the context clearly dictates otherwise. For example, the term small molecule metabolic reporter "SMMR" includes one or more small molecule metabolic reporters "SMMRs". Those skilled in the art will recognize that the terms "SMMR" and "SMMRs" are used interchangeably herein.

As used herein, the term "biologically active molecule" includes, but is not limited to, enzymes, coenzymes, metabolites, analytes, reactive species, polypeptides, proteins, cofactors, small molecules and other macromolecules of physiological significance including mixtures or active fragments or subunits thereof. A "small molecule" is defined as a molecule from 100 Da to 250 kDa. Molecules of this molecular weight range have a demonstrated ability for use as quantitative reporters of glucose activity.

The terms "small molecule metabolic reporter(s)", "SMMR(s)", "analyte enhancing molecules", "reporter" and "reporters" include, but are not limited to, fluorophores, protein-labeled fluorophores, proteins with a photooxidizable cofactor (such as FADH contained in a glucose oxidase), and proteins with another intercalated fluorophore.

As used herein, a "chromophore" is defined as a molecule exhibiting specific absorption or fluorescence emission when excited by energy from an external source. This is a more generic term than fluorophore.

As used herein, a "fluorophore" is defined as a molecule exhibiting specific fluorescence emission when excited by energy from an external source.

As used herein, an "intercalated fluorophore" is defined as a fluorophore that will fluoresce when intercalated with a molecule. For example, Glucose Oxidase-Intercalated Fluorophore (GO-IF) is a molecule with specific glucose binding sites. The fluorescent properties will change when glucose binds to the molecule, causing a measurable change.

As used herein, a "dye" is defined as a molecule having large absorptivity or high fluorescence quantum yield and which demonstrates affinity for certain materials or organic (cellular) structures.

As used herein, a "xanthene dye" is defined as a molecule having a xanthene-like skeletal structure, which exhibits large absorptivity and high fluorescence quantum yield and which demonstrates affinity for certain materials or organic (cellular) structures.

The phrase "energy transfer from reducing equivalents (e.g., NAD/NADH, NAD(P)/NAD(P)H, FAD/FADH$_2$) indicating SMMRs" refers to a use of SMMRs whereby the presence of these reducing equivalents molecules, is detected by excitation of the reducing equivalents molecules from an external source, energy transfer from the reducing equivalents molecule(s) to an SMMR, and detection of the fluorescence emission at the SMMR emission wavelength.

The phrase "transmembrane redox potential indicating SMMRs" refers to the use of SMMRs to indicate the degree of reduction-oxidation electric potential occurring within the cell, including such organelle structures as the inner mitochondrial membrane. In one such case, the degree of reduction-oxidation electric potential is indicated by the number of SMMR molecules bound to the inner mitochondrial membrane. In this case, SMMR binding is proportional to the membrane potential as indicated by quantitative fluorescence quenching. Thus, an increase in glucose brings about an increase in glycolysis and membrane potential, thereby reducing the fluorescence signal. This phrase refers to the generic use of SMMRs as a means for detecting intracellular reduction-oxidation electric potential.

The phrase "mitochondrion-selective vital SMMRs" refers to SMMRs that bind selectively to the inner mitochondrial membrane of living cells.

The phrase "pH:lactate/H$^+$ indicating SMMRs" refers to SMMRs that report on the local intra- or extracellular environment with respect to hydrogen ion concentration, pH, or lactate concentration.

The phrase "enzyme-based SMMR, including a fluorescent protein SMMR" refers to a protein-based SMMR that is capable of reacting directly with glucose to form a fluorescence response, whether measured directly as fluorescence emission intensity or fluorescence lifetime.

The phrase "intracellular pH sensitive SMMRs" refers to SMMRs that enter the cell membrane and report on intracellular pH within the cytosol. Other pH SMMRs are distinguished, as they report on organelle pH or extracellular pH, independent of cytosolic pH.

The phrase "extracellular pH sensitive SMMRs" refers to SMMRs that remain on the outside of the cell and report on extracellular pH within the interstitial fluid or extracellular environment. Other pH SMMRs are distinguished, as they report on intracellular pH, independent of extracellular pH.

The phrase "absorption/diffuse reflection or fluorescence spectrum" refers to two types of spectra measured independently. The absorption/diffuse reflection spectrum refers to the energy reflection spectrum from a material reported in either the dimensions of reflectance or absorbance versus wavelength. The fluorescence spectrum is measured independently as the fluorescence emission intensity or the fluorescence lifetime of a fluorophore following excitation from an external source.

The phrase "molecular size attachment" refers to the molecular size in Angstroms (Å), which is related to molecular weight in Daltons (Da), of an attachment added as an adjunct to an SMMR. As used herein, "molecular size attachments" is defined as adducts to the fluorescent moieties of SMMRs that include, but are not limited to, structural modifications of fluorescence SMMRs as the additions to the fluorescence structure of: acetoxy methyl esters, chloro-methyl derivatives, alkyl chain adducts, highly charged moieties, enzyme substrate mimics, enzyme cofactor tethers, and membrane binding tethers.

As used herein, a "reporter" is defined as an SMMR having the property of optical or fluorescence signal related to the quantity of analyte in the immediate vicinity of the SMMR. Thus, as the analyte quantity increases, the fluorescence signal changes (up or down) in proportion.

As used herein, a "marker" is defined as a molecule having the property of yielding a fluorescence signal that is constant when applied to target cells or tissues. Its main purpose is for use as a reference signal channel. As such, it is applied in a ratiometric measurement for correction of a reporter signal. The variation in physiological and optical characteristics of individual subjects requires a reference channel signal to correct or normalize a reporter channel signal when the ratio of reporter to marker is used for quantitative applications.

As used herein, a "sensor" is defined as a handheld device capable of making absorption or fluorescence measurements at one or more wavelengths, and converting the ratios and sums of these measurements into analyte concentrations. These analyte concentrations are used to infer the rate or quantity of a specific metabolic process.

As used herein, a "metabolite" is defined as a substance produced by a metabolic process, such as glycolysis, which can be quantitatively measured as an indication of the rate or quantity of a specific metabolic process.

As used herein, an "analyte" is defined as a measurable parameter, using analytical chemistry, which can be quantitatively measured as an indication of the rate and quantity of a specific metabolic process. The term analyte is a generic term describing such concepts as metabolites, ions, processes, conditions, physico-chemical parameters, or metabolic results that can be used to infer the rate or quantity of specific metabolic processes.

As used herein, a "response range" is defined as an analyte range (lower and upper limits) over which a metabolic process, and its measured absorption or fluorescence signal, follow a linear or defined mathematical function.

The phrase "physico-chemical parameter" refers to a subset of broadly defined analyte parameters specifically related to the physical chemistry constants of materials. These constants can be used in combination with the measurement of other analytes to infer the rate or quantity of specific metabolic processes. Such constants refer specifically to, e.g., atomic mass, Faraday constant, Boltzmann constant, molar volume, dielectric properties, and the like.

As used herein, "wicking" is defined as the flow of a liquid into a solid material via the pull of gravity, Brownian motion, adhesion, mass transport, or capillary action such that a natural movement of a liquid occurs into a solid material.

The phrases "direct metabolic reporters," and "indirect metabolic reporters" refer to the mechanism of action of SMMR for reporting glucose concentration. Direct metabolic reporters report the concentration of glucose directly, whereas indirect metabolic reporters report the concentration of analytes used to infer the concentration of glucose.

As used herein, an "octanol-water coefficient ($K_{ow}$)" is defined as a measure of the extent to which a solute molecule is distributed between water and octanol in a mixture. The octanol-water partition coefficient is the ratio of a chemical's solubility (concentration) in octanol to that in water using a two-phase mixture at equilibrium.

As used herein, "toxicity" is defined as the degree or quality of being toxic or hazardous to the health and well being of human and other mammalian organisms, organs, tissues, and cells.

The phrase "specialized tattoo" or more precisely the "active viewing window" refers to an area of tissue treated with an SMMR. That area is used for viewing the fluorescence ratio measurements of the SMMR interaction with tissue, in order to directly measure, calculate, or otherwise infer the concentration of skin and blood glucose or other metabolites of interest.

As used herein, "organ" is defined as a structure that contains at least two different types of tissue functioning together for a common purpose. Examples of organs in the body include, but are not limited to, the brain, heart, liver, kidneys, pancreas, stomach, intestines, lungs, skin.

As used herein, a "keratinocyte" is defined as a living cell comprising the majority of the epidermis of mammalian skin. The keratinocyte is unique in both its proximity to the surface of an organism as well as in its glycolytic behavior. The keratinocyte metabolizes glucose in such a way as to produce a number of analytes whereby the glucose concentration within the cell can be inferred.

As used herein, "Rt (in ohms)" is defined as the sum of a 5-ohm series resistor and the resistance (impedance) of the skin in parallel with a 50-ohm resistor.

As used herein, "Rskin" is defined as impedance representing a function of the electrode contact resistance, the distance between electrodes, and the applied pulse. Rskin is typically in the range of 30 to 100 kohm/cm$^2$.

As used herein, a "mammal" includes both a human and a non-human mammal (e.g., rabbit, mouse, rat, gerbil, cow, horse, sheep, etc.). Transgenic animals are also encompassed within the scope of the term.

Although methods and materials similar or equivalent to those described herein can be used in the practice or testing of the present invention, suitable methods and materials are described below. All publications, patent applications, patents, and other references mentioned herein are incorporated by reference in their entirety. In the case of conflict, the present specification, including definitions, will control. In addition, the materials, methods, and examples are illustrative only and not intended to be limiting. Other features and advantages of the invention will be apparent from the following detailed description and claims.

BRIEF DESCRIPTION OF THE DRAWINGS

FIG. 4A depicts Reporter and Marker channel detection using a dual wavelength measurement technique. FIG. 4B depicts measurement of the Total Integrated Fluorescence Signal (gray region). The initial signal measured to determine glucose concentration [Glucose$_I$] is derived as a function of the ratio of the fluorescence signal from the reporter to marker such that [Glucose$_I$]=f(Reporter/Marker). A multichannel wavelength correction is applied later. As designated in the FIG. 4A, FL*=Fluorescence detection;

FIG. 5A depicts light correction profile detection. FIG. 5B depicts broad wavelength reflection signal measurement (gray area). As designated in the FIG. 5A, DR*=Diffuse Reflection;

FIG. 10A and FIG. 10B are a schematic and a magnified insert, respectively, showing how small metabolites present in the blood are transported from the blood vessels of the dermis into the interstitial fluid of the epidermis. This occurs as the metabolites move from small blood vessels in the subcutaneous layers of the integument into the capillary fields of the dermis. Metabolite molecules useful for tracking glucose include D-glucose; lactate; H$^+$; NAD(P)H; Ca$^{2+}$; FAD$^+$; redox potential (mitochondrial membrane); ATP/ADP; and O$_2$ (aerobic). Such small metabolite molecules move from the capillaries to the interstitial fluid surrounding the epidermal keratinocytes via mass transport. Thus the metabolite concentration for interstitial fluid outside the keratinocytes is proportional to the concentration of metabolites in peripheral dermal blood vessels. The only exception to this is oxygen, which decreases with distance from the subcutaneous blood vessels. At approximately 50 to 100 μm down from the surface of the skin, there is very little oxygen, which is why the keratinocytes function using anaerobic glycolysis. Applications of SMMRs as reporters for blood metabolite and precursor levels can be inferred from peripheral tissue metabolite levels (i.e., why measurements of skin are useful for measurement of some blood metabolites). Small metabolite molecules move from the capillaries to the interstitial fluid via non-insulin regulated, concentration dependent, mass transport (i.e., a diffusion rate of ~4 to 10% per minute of the difference in concentration between capillary and skin metabolite levels). The skin cells transport via GluT1 (GenBank Accession Number: K03195), not GluT4 (GenBank Accession Number: M91463);

FIG. 17A depicts mechanisms operating in skin metabolism and points of measurement using SMMRs (Scheme 1). FIG. 17B depicts an overview of the metabolic pathways for glucose in epidermis (Scheme 2). FIG. 17C depicts the structure of a generic chemical backbone for designing a pH sensitive dye for specific action as a lactate/$H^+$ SMMR (Scheme 3). FIG. 17D illustrates fluid issues related to in vivo skin calibration (Scheme 4);

FIG. 28 lists mechanisms of action of the reporters of the invention. The mechanisms of action are threefold: (1) as a technology to increase the signal-to-noise of native autofluorescence signals indicative of human glucose metabolism [for FAD, NADH, and NAD(P)H], (2) for the enhancement of specific metabolite and precursor signals in tissue that are indicative of glucose metabolism and allow determination of changes in blood glucose [$Ca^{2+}$, lactate, oxygen], and (3) as a technology to directly measure the presence of intracellular or extracellular molecular glucose [GOx-LF, and GOx-$^3$FAD*];

FIG. 29 is a diagram demonstrating the mechanism of action for energy transfer reporters;

FIG. 30 is a diagram demonstrating the mechanism of action for redox potential reporters;

FIG. 32 is a diagram demonstrating the mechanism of action for ion pump reporters (via calcium ion tracking);

FIG. 33 is a diagram demonstrating the mechanism of action for oxygen utilization reporters;

FIG. 36 is a schematic showing the method for adding SMMRs to peripheral epithelial cells in tissues and organs;

DETAILED DESCRIPTION

Figure 1:
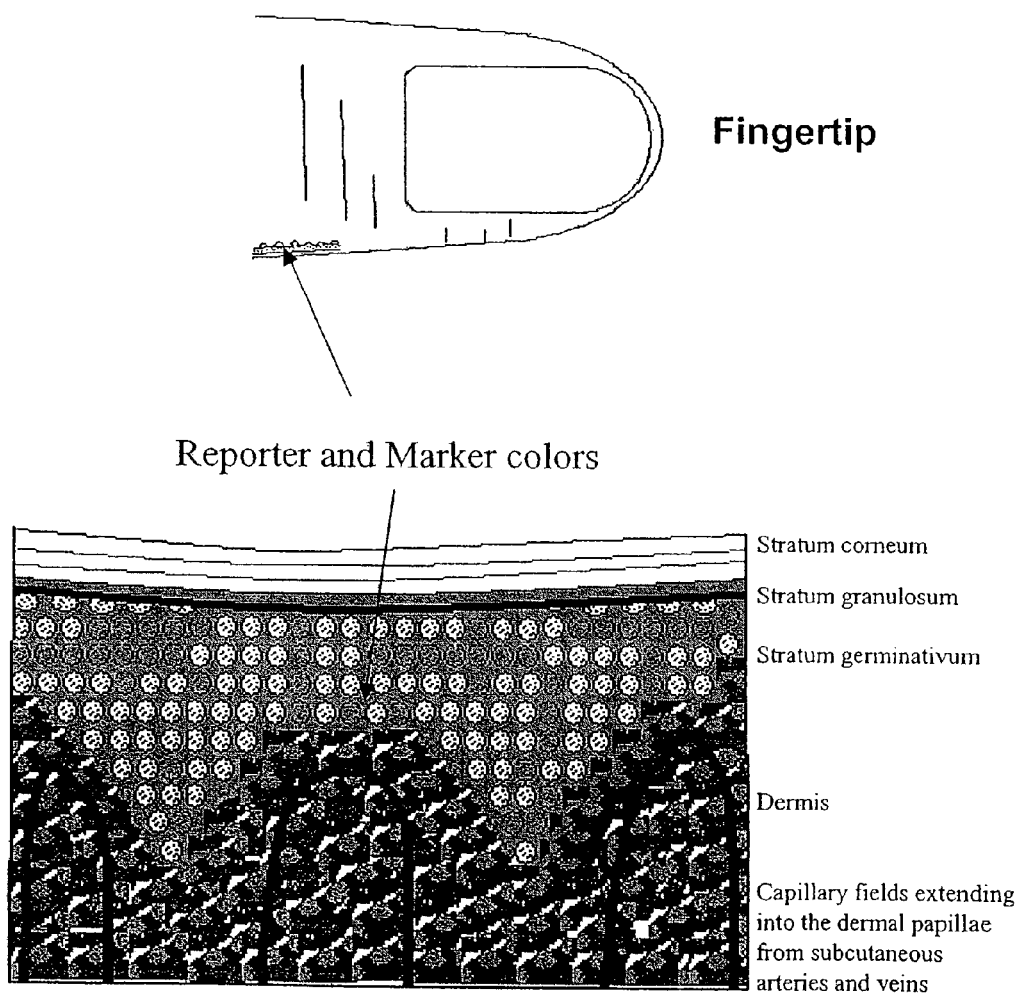
FIG. 1 is a schematic showing the preferred location for small molecule metabolic reporters (SMMRs) as they are introduced into the stratum germinativum or dermis near the surface of peripheral tissue or skin using one of many possible techniques disclosed for monitoring of blood borne metabolites which move to peripheral cells and tissues.
Figure 2A:
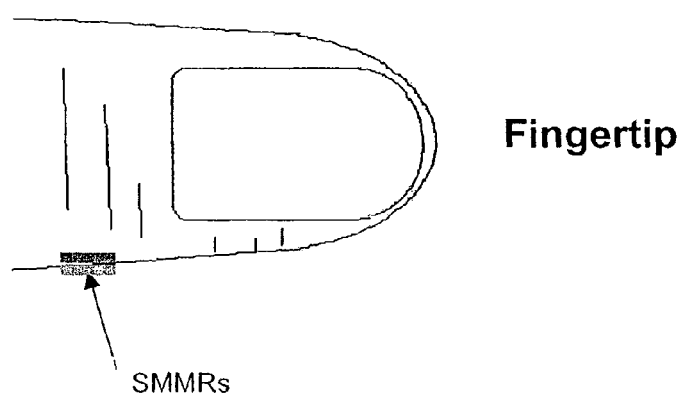
FIG. 2A and FIG. 2B are schematics showing the method for coloring epidermal skin cells (i.e., keratinocytes) of the fingertip (FIG. 2A) using a sensor composition of the invention, wherein one or more SMMRs are applied to the skin surface and transported up to 1500 microns (μm) through the top of the skin using passive or active transport (FIG. 2B)
Figure 2B:
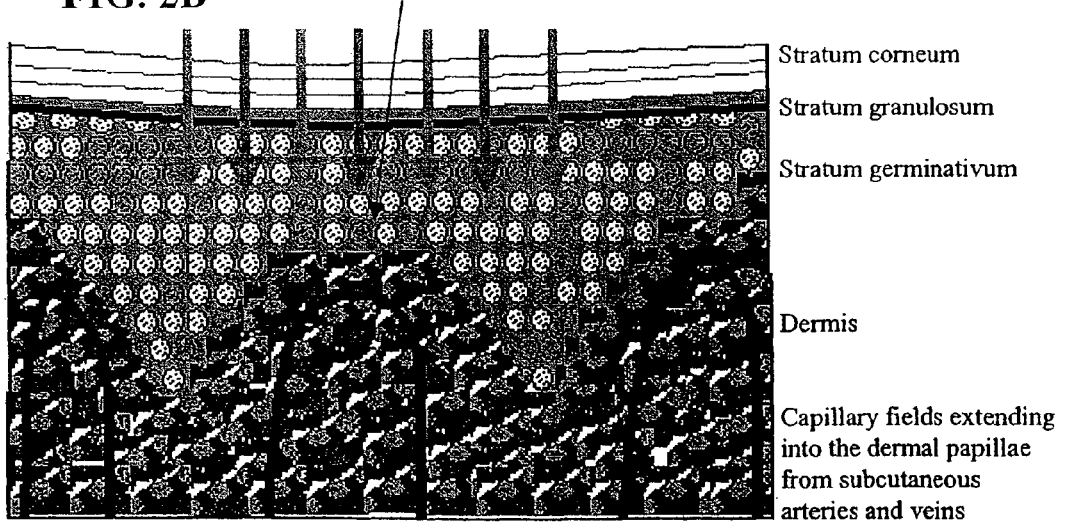
Figure 3A:
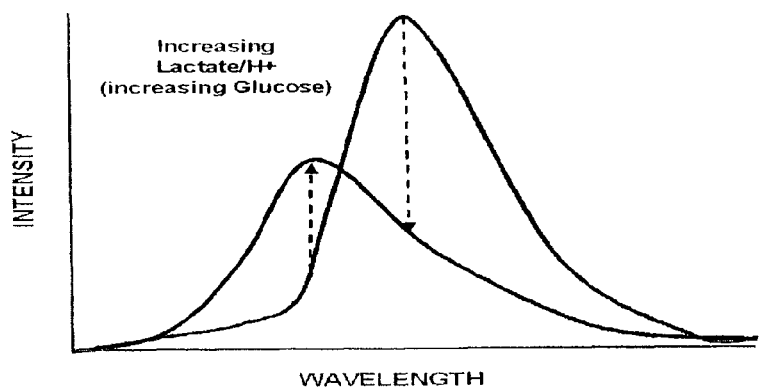
FIG. 3A and FIG. 3B are schematics showing the fluorescence response to D-glucose using a Lactate/H$^+$ small molecule metabolite reporter (FIG. 3A), and the corresponding epidermal location of the SMMR in the stratum germinativum near the surface of the skin (FIG. 3B) and demonstrates a spectral response to changes in D-glucose as measured by lactate/H$^+$ reporting shown in FIG. 3A.
Figure 3B:
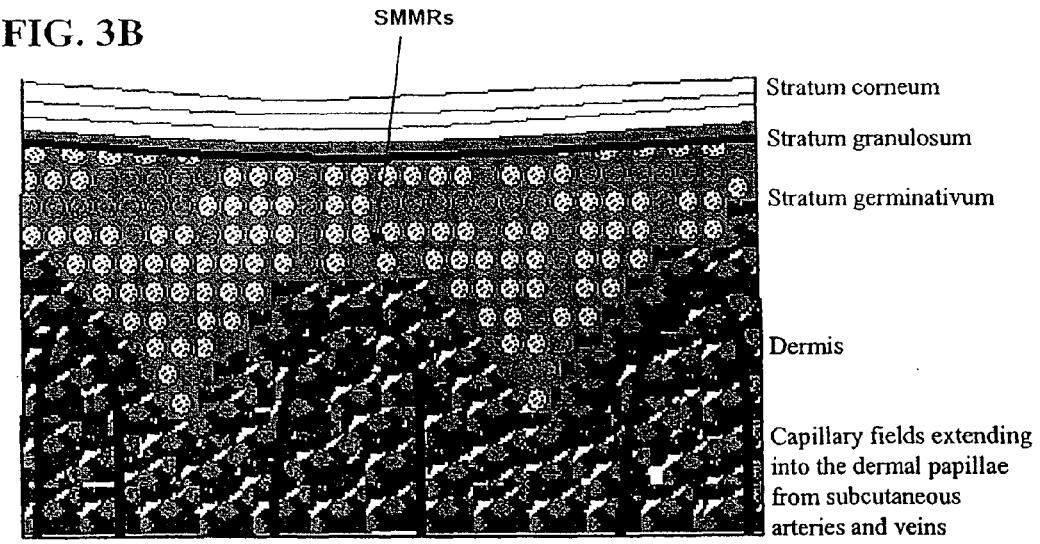

The non-invasive devices, compositions, and methods of the present invention directly yield in vivo information for the assessment of intracellular and extracellular metabolic state, as well as the stress status of cells, tissues, and organisms. In a preferred embodiment, the devices, compositions and methods of the invention can be used to monitor and determine metabolite concentration levels, and more specifically, determine blood glucose concentration levels.

Truly non-invasive methods require that no device is placed into or under the tissue; that no probe is used to remove fluid or to inject materials into the tissue; and that the protective layers of tissue, such as the stratum corneum of skin, or outer membrane layers of organs, are not mechanically penetrated or otherwise physically compromised.

Procedures that create pores or holes in the tissue for introducing molecules or extracting fluid are considered somewhat invasive. Ideally, a non-invasive monitoring device would supply continuous, accurate monitoring of intracellular activity, extracellular state, and whole organism or tissue metabolic status. In this way direct, real-time information regarding tissue, organ, and organism metabolic status is produced. In contrast, chemical sensors making measurements of highly buffered and highly regulated body fluids such as interstitial fluids and blood provide less responsive, more indirect data regarding tissue and overall subject status.

The invention provides non-invasive sensor compositions that comprise one or more small molecule metabolic reporters ("SMMRs" or "reporters"). When applied topically to skin, peripheral tissues, or organs, these reporters are able to penetrate the upper tissue layers and interact with a specific biologically active molecule in such a way as to report metabolic or health status, while not interfering with metabolic function. The reporters provide a metabolic signal that can be used for multiple purposes including, but not limited to, assessment of metabolic function (e.g., particularly as related to glucose metabolism); diagnosis of metabolic disease states (e.g., as related to advanced glycosylated end-products); monitoring and control of disease state; stress status of cells, tissues and organs; determination of vitality and viability of cells based on metabolic function; critical care monitoring; diagnosis and monitoring of cardiovascular diseases, autoimmune disorders, neurological disorders, degenerative diseases; determination of metabolic concentration; and cancer diagnosis, detection, staging and prognosis. Specifically, applying the reporters of the invention to living peripheral or epithelial tissue provides detailed information on the state of multiple metabolic pathways in living organisms that can be analyzed using low-cost, hand held instrumentation.

The advantages of the mechanisms of action of the reporters of the invention are threefold: (1) as a technology to increase the signal-to-noise of native autofluorescence signals indicative of human glucose metabolism [for FAD, NADH, and NAD(P)H], (2) for the enhancement of specific metabolite and precursor signals in tissue that are indicative of glucose metabolism and allow determination of changes in blood glucose [$Ca^{2+}$, lactate, oxygen], and (3) as a technology to directly measure the presence of intracellular or extracellular molecular glucose [GOx-LF, and GOx-$^3$FAD*]. The mechanisms of action for these small molecule metabolic reporters are described in FIGS. 28-35.

The invention provides techniques whereby one or more reporters are applied to solid tissue (i.e., are introduced to the upper cell layers of tissues and organisms following local and/or topical administration). The reporters are added in trace quantities (from about 10 to about 1000 μL of 0.1 to 200 μM, preferably from about 5 to about 100 μL), using a substance that is transparent to visible light and that has a pre-specified temporary residence at the application site (e.g., 2 days-up to 30 days, 24-48 hours, preferably 2-6 hours, more preferably 30 seconds to 5 minutes, and most preferably 5 seconds to 5 minutes). Contemplated diffusion times include periods less than 48 hrs, 24 hrs, 10 hrs, 6 hrs, 2 hrs, 1 hr, 30 min, 15 min, 10 min, 5 min, 1 min, 30 sec, 10 sec, or 1 sec. Reporters that are placed on skin are able to penetrate the skin and be transported to a depth from the surface of from about 10 μm to about 300 μm into the tissue and are brought in contact with a specific metabolite, wherein a change in fluorescence or absorption (e.g., measured using fluorescence or absorption spectroscopy) of the one or more reporters occurs, thereby allowing quantification of the change in fluorescence or absorption that provides detailed in vivo information regarding picomolar through millimolar cellular metabolite and precursor levels for living tissue, organs, interstitial fluid, and whole organisms.

The reporters can be monitored non-invasively using any low-cost instrumentation capable of directly analyzing the metabolic state in tissue (e.g., using optical instrumentation). The reporters are chosen to specifically enhance the signal of pre-specified analytes in order to assess metabolic state of a tissue or organism and to yield detailed, real-time information regarding the state of intracellular and extracellular metabolism.

Methods are provided for the direct measurement of intracellular and extracellular metabolism in epidermal or epithelial cells using these reporters in combination with fluorescence or absorption detection. The specific optical signal used to measure metabolite or precursor levels is derived from emission or reflection using fluorophores or analyte-binding proteins with fluorescence labels. These analyte-enhancing molecules, e.g., SMMRs, have specific properties as described herein.

In one embodiment, the invention provides methods for deriving SMMRs as follows: (1) delineating the metabolites or precursors (analytes) required to characterize a metabolic pathway in a living system (e.g., see FIG. 34 for various/optional alternative glucose metabolism pathways); (2) selecting a basic mechanism of action for the SMMR (see FIGS. 22-27 for examples of glycolytic activities); (3) selecting the wavelength options for excitation and emission of the SMMR by absorption and fluorescence measurements; (4) selecting molecular structure to meet quantum efficiency and yield requirements; (5) selecting location, diffusion rate, and duration or lifetime of the SMMR within the tissue or organ layers; (6) selecting toxicity requirements and limitations; and (7) relating measured real-time metabolic conditions to normal versus disease state for diagnostics or patient care.

In order to accomplish this, the reporter is derived using a combination of molecular properties including, but not limited to, specific molecular size, polarity, charge, structure, pKa, solubility, and the size and type of molecular attachments or anchors. Each of the steps are provided to optimize the real-time monitoring of metabolic conditions in living cells using non-invasive, in vivo, and low-cost instrumentation, as described herein.

Metabolic pathways for glucose, fructose, and galactose have been described in detail in numerous references delineating biochemical pathways (See, Metzler, D. E., 1977, Biochemistry: The Chemical Reactions of Living Cells, Academic Press, New York, pp. 539-543, 673; Stryer, L., 1988, Biochemistry, 3$^{rd}$ Ed., W.H. Freeman and Company, New York, pp. 349-370; Champe, P. C., Harvey, R. A., 1994, Biochemistry, 2$^{nd}$ Ed., Lippincott Williams & Wilkins, Philadelphia, pp. 61-157).

Metabolic monitoring, as provided using the reporters of the invention, requires a detailed understanding of the metabolic pathways and analytes required to understand the relationship between a measured analyte and the metabolic or disease state. Simply measuring a specific analyte does not necessarily give detailed information on disease or metabolic state of cells, tissues, or organisms. FIGS. 22-27 show various metabolic pathways of interest, and depict how the reporters of the invention can be used to analyze specific analytes for the assessment of metabolic function, providing detailed information on glucose metabolism, fructose metabolism and/or galactose metabolism. Examples of specific analytes include, but are not limited to, glucose, NAD(P)H, ATP, NADH, FAD, lactate, $Ca^{2+}$, and $O_2$.

The invention provides sensor compositions that can be present in the epidermis at a depth from the surface of the skin of about 10 μm, which corresponds to the bottom of the dead stratum corneum layer, to about 175 μm, which typically corresponds to the top of the dermal layer. However, those skilled in the art will recognize that depths up to about 1500 µm are also contemplated as part of the invention. In a preferred embodiment, the sensor compositions of the invention can be present in the epidermis at a depth from the surface of the skin to about 175 µm. However, in certain embodiments, the sensor composition can be present in the epidermis at a depth from the surface of the skin to about 300 µm, about 500 µm, about 1000 µm and about 1500 µm. For example, when the sensor compositions are present on the eyelids, the sensor composition may be present in the epidermis at a depth from the surface of the skin of about 50 µm. When the sensor compositions of the invention are present on the soles of the feet, it may be desirable for the compositions to be present in the epidermis at a depth from the surface of the skin of up to about 1500 µm. Thus, those skilled in the art will recognize that the sensor composition may be present in the epidermis at varying depths from the surface of the skin depending on site of measurement and variation among individuals.

The skin SMMR compositions are present in the epidermis at an effective concentration that allows one or more metabolites or analytes in a metabolic pathway to be detected in a subject or biological sample.

The invention is designed to target analytes capable of providing detailed information for peripheral tissue metabolic pathways that are driven specifically by the measured analyte or analytes. Where these biosynthetic processes require multiple analytes, or are for metabolic systems that are distinctly non-linear, analytes representing more than one pathway may be combined to model such systems. A final measurement system for multiple analytes provides a wide dynamic range and is less prone to interference. For human subjects, first principle mathematical models can be developed, preferably for individual subjects, more preferably for small local populations, and most preferably for the universal case.

The mechanism of action of any specific reporter of the invention is related to its unique properties in interacting in real-time with a known metabolic biochemical reaction for the explicit purpose of instantaneously defining metabolic function in living tissue. It is noted that one skilled in the art could easily adapt this invention for either additional in vivo or in vitro applications on other tissue, if desired, by using the same principles taught herein.

In one embodiment, the invention provides in vivo methods for monitoring and controlling disease states that affect metabolic processes in living organisms by applying one or more reporters to a surface of the skin for a predetermined period of time; causing penetration of the reporter to a depth of about 10 µm to about 175 µm; monitoring a change in the fluorescence or absorption based upon peripheral or epithelial tissue metabolite levels; and correlating the metabolite levels within peripheral or epithelial tissue with cellular metabolite levels, thereby monitoring and controlling disease states that affect metabolic processes in living organisms.

In another embodiment, the invention provides in vivo methods for determining the metabolic health and well-being in living organisms by applying one or more reporters to a surface of the skin for a predetermined period of time; causing penetration of the reporter to a depth of about 10 µm to about 175 µm; monitoring a change in the fluorescence or absorption based upon peripheral or epithelial tissue metabolite levels; and correlating the metabolite levels within peripheral or epithelial tissue with cellular metabolite levels, thereby determining the metabolic health and well-being in living organisms.

The invention also provides methods for monitoring the concentration of one or more metabolite(s) or analyte(s) in a metabolic pathway using the sensor compositions of the invention. According to these methods, the sensor composition is applied to the surface of the skin for a predetermined period of time. The sensor composition penetrates the epidermis to a depth of about 10 µm, which corresponds to the bottom of the dead stratum corneum layer, to about 175 µm, which corresponds to the top of the dermal layer. An optical reader is used to monitor changes in the concentration of the one or more metabolite(s) or analyte(s) in a metabolic pathway. These changes in concentration are monitored by detecting changes in one or more reporter dyes, at one or more points in time. Monitoring the change in metabolite or analyte concentration can be accomplished by detecting at least one wavelength above 350 nm, including wavelengths above 400 nm, 450 nm, 500 nm, 550 nm, 600 nm, 650 nm, 700 nm, 750 nm, 800 nm, 850 nm, 900 nm and above. In a preferred embodiment, the change in metabolite or analyte concentration can be accomplished by detecting at least one wavelength above 450 nm.

The invention provides methods for determining the concentration of at least one metabolite or analyte in skin tissue. According to these methods, a small molecule metabolite reporter SMMR is administered to the skin tissue. The SMMR penetrates to a region of the skin at a depth between the dermis and the epidermis, wherein the depth from the surface of the skin is from about 10 µm to about 175 µm. The SMMR is irradiated with a source of electromagnetic radiation, and the fluorescence spectra emitted from the SMMR is detected. The emitted fluorescence spectra are then analyzed, which results in a determination of the concentration of the metabolite or analyte. Measuring the fluorescence spectra according to these methods can include a bloodless calibration procedure, such as, for example, the procedure(s) outlined in equations 13, 16, 17, 18, 19, 20 and 21 set forth herein (See Examples 5-8).

The ability to derive primary and secondary order information regarding real time, dynamic glucose metabolism (such as the direction and rate of change of bioavailable glucose distributed within the blood and interstitial fluid space) is desirable. In vivo fluorescence (autofluorescence) has been used for a number of years to determine the metabolic state and to monitor pharmaceutical effects in cells and tissues. See, e.g., Dellinger et al., *Biotechnol Appl Biochem*, 28 (Pt. 1): 25-32, (1998). Consideration of the photophysics involved in autofluorescence rapidly leads one to the conclusion that the use of autofluorescence alone, as the analytic probe or mechanism, imposes some severe limitations on any measurement technique. Specifically, signal-to-noise is not sufficient to meet the requirements for an accurate, low-cost, quantitative measurement.

Recently, the state-of-the-art in making time resolved fluorescence measurements have advanced to a degree whereby robust and low-cost instrumentation can be readily assembled. However, effective measurements have only been made in vitro for specific analytes, and real-time in vivo analysis has yet to be reported. Researchers have used phase-modulation fluorometry in vitro to demonstrate first generation sensing devices for a number of analytes ($pO_2$, pH, $pCO_2$, $NH_3$, etc.). See e.g., Dalbey, R. E., et al., *J. Biochem. Biophys. Meth.*, 9: 251-266, (1984). The use of long lifetime red-sensitive probes has resulted in transdermal sensing becoming a reality since human skin is translucent at wavelengths above 630 nm.

Fluorescent lifetime-based sensing offers novel applications in the bioprocessing and biomedical arenas. For instance, in measurement of Green Fluorescent Protein (GFP) as a marker for expression of heterologous proteins does not require any additional co-factors for its visualization. GFP-fusion proteins have been expressed in a variety of cell lines and in situ measurements in bioreactors have been made. Fluorescence polarization measurements for the quantitation of large antigens, such as antibodies labeled with long-lived fluorescent labels, can, in principle, directly measure antigens of several million Daltons (Da).

Fluorescence techniques are capable of detecting molecular species at picomole (pm) levels or less. This sensitivity arises because of the simplicity of detecting single photons against a dark background. This advantage disappears if there are other fluorescent species in the detection volume that is obtained from the sample material being measured. Furthermore, fluorescence intensity is not an absolute technique and measurements must be referenced to an internal standard using a ratiometric or comparative method.

Autofluorescence arises from the innate fluorescence of compounds that are not particularly efficient fluorophores and that are not photostable. Because of these properties, detectors for autofluorescence need to have an excellent signal-to-noise ratio, with sufficient dynamic range, and require that the excitation source be of low enough power so as not to cause photosensitization. In addition, there are a number of fluorescing species present in the skin that constitute a significant background signal. The situation is further complicated in that it is quite difficult to identify or introduce a standard optical reference material or apparatus into the skin.

Fluorophores, or colored dyes utilizing absorption spectroscopy, can be used to measure glucose in solution or serum by using a series of separate generic reagents. These generic reagents include, but are not limited to, glucose oxidase (which oxidizes glucose forming hydrogen peroxide) or peroxidase (generally horseradish peroxidase ("HRP") used to create an oxidizing reaction in the presence of hydrogen peroxide with the dye or fluorophore), and a dye reagent or fluorophore, which changes its color or fluorescence spectrum when brought in contact with hydrogen peroxide and peroxidase. The resultant colored or fluorescent species is measured with a colorimeter or fluorometer, and the amount of glucose in solution is calculated. In addition, other standard analytical techniques have been shown to be commercially useful for measuring hydrogen peroxide generated from the reaction of glucose oxidase and glucose.

Tissues derive free energy from the oxidation of fuel molecules, including glucose and fatty acids. In energy releasing metabolic processes, fuel molecules transfer electrons to carrier molecules for transport and conservation. These basic carrier molecules are either pyridine nucleotides or flavins. The carrier molecules, in their reduced form, transfer high-energy electrons to molecular oxygen by means of an electron transport chain located in the inner membrane of mitochondria. Upon electron transport, adenosine diphosphate (ADP) and orthophosphate ($P_i$) yield adenosine triphosphate (ATP) useful as an energy source in many metabolic processes.

Aerobic glycolysis results in the biosynthesis of pyruvate which serves as a substrate for the mitochondria. In turn, this substrate feeds oxidative phosphorylation resulting in ATP production. Mitochondrial inner membrane redox potential can be measured using the reporters of the invention as an indication of healthy or perturbed aerobic cell function as exemplified by oxidative phosphorylation. The mitochondrial membrane potential indicates status of the biosynthetic process of ATP production for powering cellular metabolism. This ATP synthesis is directly coupled to the flow of electrons from the reduced forms of the coenzymes nicotinamide adenine dinucleotide (NADH), nicotinamide adenine dinucleotide phosphate (NAD(P)H), and flavin adenine dinucleotide ($FADH_2$) to molecular oxygen ($O_2$) by a proton gradient across the inner mitochondrial membrane.

Nicotinamide adenine dinucleotide ($NAD^+$) is a major electron acceptor in the oxidation of fuel molecule (e.g., glucose, fructose, galactose) oxidation. The nicotinamide ring of $NAD^+$ (oxidized form) accepts a hydrogen ion plus two electrons becoming NADH (reduced form). Another major electron acceptor is flavin adenine dinucleotide (FAD) due to its isoalloxazine ring. The oxidized form of FAD is denoted as FAD, whereas the reduced form is $FADH_2$. The major electron donor in most reductive biosyntheses is NAD(P)H (reduced form). The oxidized form of this electron donor is $NAD(P)^+$. NADH is used for ATP production, whereas NAD(P)H is used for reductive biosynthesis. SMMRs are useful for energy transfer enhancement for direct detection of NADH and NAD(P)H as well as $FADH_2$ thereby indicating biosynthetic activity levels. An increase in the formation of these electron transfer species can be measured and is indicative of substrate concentration (e.g. glucose) and overall metabolic health and activity.

In one preferred embodiment of the invention, the devices, compositions, and methods effectively determine and monitor the glucose concentration in blood for a living organism by non-invasive, in vivo measurement of the glucose level in skin by means of fluorescence measurements of metabolic indicators/reporters of glucose metabolism, or by means of direct measurement of glucose levels in the skin, as described below.

Indirect Measurements using the Sensor Compositions of the Invention

This invention provides for fluorescence measurements of extracellular and intracellular reporter molecules placed into the cytosol, nucleus, or organelles of cells within intact, living, tissue that track the concentration of blood glucose in an organism. When any one of a series of metabolites or analytes is measured using this technique, the molar concentration of blood glucose can be calculated. The one or more metabolite(s) or analyte(s) can directly report on, and relate to, in vivo blood glucose levels. Suitable metabolites or analytes include for example, lactate; hydrogen ion ($H^+$); pH (as lactate/$H^+$); calcium ion ($Ca^{2+}$) pumping rate; magnesium ion ($Mg^{2+}$) pumping rate; sodium ion ($Na^+$) pumping rate; potassium ($K^+$) pumping rate; adenosine triphosphate (ATP); adenosine diphosphate (ADP); the ratio of ATP to ADP; glycogen; pyruvate; nicotinamide adenine dinucleotide phosphate, oxidized form (NAD(P)+); nicotinamide adenine dinucleotide phosphate, reduced form (NAD(P)H); flavin adenine dinucleotide, oxidized form ($FAD^+$); flavin adenine dinucleotide, reduced form ($FADH_2$); or oxygen ($O_2$) utilization. These analytes, measured in skin using the techniques taught herein, provide a complete picture of epidermal skin metabolism where local epidermal analyte (glucose) quantities are proportional to the concentration of glucose in systemic blood, specifically the capillary fields within the papillary layer of the dermis (corium). Temperature and/or nitric oxide measurement may also be combined with the above measurements for better calibration and determination of glucose concentrations.

The invention provides methods for monitoring in vivo blood glucose levels by applying the sensor composition of the invention to a surface of the skin for a predetermined period of time. The sensor composition penetrate the epidermis to a depth of about 10 µm, which corresponds to the bottom of the dead stratum corneum layer, to about 175 µm, which corresponds to the top of the dermal layer. However, depths up to about 300 µm are also contemplated as part of the invention. An optical reader is used to detect changes in the reporter dye by monitoring changes in the concentration of the one or more metabolites or analytes. The change in the concentration of the one or more metabolites or analytes is then correlated with in vivo blood glucose levels. Monitoring the change in metabolite or analyte concentration can be accomplished by detecting at least one wavelength above 350 nm.

The invention also provides methods for measuring in vivo blood glucose levels through the skin by monitoring, in a population of cells, one or more relevant metabolites or analytes in at least one metabolic pathway. The one or more metabolite(s), parameter(s) or analyte(s) is monitored by measuring the fluorescence spectrum emitted by a reporter composition located in the skin. The fluorescence spectrum emitted by the reporter is stoichiometrically related to the metabolite, parameter or analyte concentration in the population of cells. The in vivo blood glucose level is determined by analyzing the fluorescence spectrum, using the known stoichiometric relationship between the fluorescence spectrum of the reporter and the metabolite, parameter or analyte concentration.

The population of cells can have a predominantly glucose metabolism, or alternatively, the population of cells can be induced to have a glucose metabolism. The population of cells in the skin can be located in the epidermis, which contains a dynamic, metabolically homogeneous, and homeostatic population of cells. For example, the population of cells having a glucose metabolism can include live keratinocytes. These live keratinocytes can be present in the epidermal layer of skin. In some cases, the live keratinocytes can be present in the skin at a depth, from the surface of the skin, of about 10 µm, which corresponds to the bottom of the dead stratum corneum layer, to about 175 µm, which corresponds to the top of the dermal layer.

The metabolic pathways monitored within the population of cells, according to these methods for measuring in vivo blood glucose levels through the skin, can be monitored by measuring a specific metabolite or analyte of the glycolytic pathway, wherein the specific metabolite or analyte has a known stoichiometric or highly correlated relationship with glucose concentration. The metabolic pathways can also be monitored within the population of cells by observing a physico-chemical parameter that is related to the glycolytic pathway, wherein the selected physico-chemical parameter has a stoichiometric or highly correlated relationship with glucose concentration.

Metabolites produced as the result of glycolysis that are present in the cell can also be measured in vivo, using the reporters of the invention. These metabolites include lactate; hydrogen ion ($H^+$); calcium ion ($Ca^{2+}$) pumping rate; magnesium ion ($Mg^{2+}$) pumping rate; sodium ion ($Na^+$) pumping rate; potassium ion ($K^+$) pumping rate; adenosine triphosphate (ATP); adenosine diphosphate (ADP); the ratio of ATP to ADP; inorganic phosphate ($P_i$); glycogen; pyruvate; nicotinamide adenine dinucleotide phosphate, oxidized form (NAD(P)+); nicotinamide adenine dinucleotide (phosphate), reduced form (NAD(P)H); flavin adenine dinucleotide, oxidized form (FAD); flavin adenine dinucleotide, reduced form ($FADH_2$); or oxygen ($O_2$) utilization. Individually or in combination, these metabolites measured in skin using the techniques taught herein give a complete picture of epidermal skin glucose metabolism, and an indirect measure of the quantity of glucose molecules entering the cells.

The population of cells to be monitored in these methods for measuring in vivo blood glucose levels through the skin can have a predominantly oxidative metabolism, or alternatively, the population of cells can be induced to have a metabolism predominantly based on oxidative phosphorylation. The metabolic pathways monitored within the population of cells can be monitored by measuring a metabolite or analyte that is generated as a result of the oxidative metabolic pathway, wherein the specific metabolite or analyte has a stoichiometric or highly correlated relationship with glucose concentration. Alternatively, the metabolic pathways can be monitored within the population of cells by observing a physico-chemical parameter that is generated as a result of the oxidative metabolic pathway, wherein the physico-chemical parameter has a stoichiometric or highly correlated relationship with glucose concentration.

The invention also provides methods for determining blood glucose concentration. According to these methods, a first instrument response measurement is performed using a calibration target, and the response data is recorded. A first SMMR mixture is applied to the skin in a first, controlled area, such that the SMMR resides in the epidermal layer of the skin, and a second SMMR mixture is applied to the skin in a second, controlled area. The second area is perturbed, such that extreme changes that the mixture may undergo are achieved. The extreme change can be, for example, a change in concentration of the analyte comprising a zero or low concentration and a saturation level or high concentration; or the extreme change can be, for example, a change in temperature, as described herein. A second calibration measurement is then performed on the perturbed area, and the calibration data is recorded. A third background measurement is made on an area of skin that has no SMMR, whereby this background data is recorded. A measurement on the first area is performed by illuminating the first area with light, and the wavelength spectrum of light reflected back from the first area is detected. Further measurements on the first area are performed at wavelengths suitable for each SMMR present. A parameter from the response data is calculated in order to normalize the background data, calibration data and measurement data for the response of the spectrometer. A parameter from the background data is calculated in order to correct the calibration data and measurement data for emission, absorption and scattering properties of the tissue. A metabolite parameter from the calibration data is calculated in order to relate the measurement data to the blood glucose concentration.

The invention also provides methods of calculating a blood glucose concentration. Accurate direct or indirect in vivo measurement of glucose concentration in immortal cell lines, human keratinocyte cell cultures, and mammalian (including human) skin are achieved by using this application of in vivo fluorescence labeling and detection of SMMRs in skin. According to these methods, a background response and an autofluorescence tissue response is measured from a calibration target that includes an epidermal layer of skin. A first dye is provided to a first skin location, and residues of the first dye mixture are transferred into the epidermal layer of the skin. A second dye is provided to a second skin location, and at least one extreme change in the mixture is triggered and recorded. The extreme change can be, for example, a change in concentration of the analyte comprising a zero or low concentration and a saturation level or high concentration; or the extreme change can be, for example, a change in temperature, as described herein. These extremes are used to calibrate the sensor enabling it to measure a test sample accurately with a concentration between the extremes. See e.g., equations (13) through (21), as described herein (Examples 5-8). The first skin location is illuminated with a radiative emission, and a resulting wavelength spectrum reflected from the first skin location is detected. The illuminating and detecting can be repeated using irradiation and wavelength spectra associated with each dye provided. At least one physico-chemical parameter that is related to the glycolytic pathway is then detected. Preferably, the physico-chemical parameter has a stoichiometric or highly correlated relationship with glucose concentration, which is used in determining the blood glucose concentration. The sensor system can include a bloodless calibration procedure such as, the procedure(s) outlined in equations 13, 16, 17, 18, 19, 20 or 21 set forth herein (Examples 5-8).

The methods and compositions of the present invention use reporters such that two basic techniques are available for obtaining ratiometric measurements of glucose concentration or exemplary utilization versus fluorescence response. Mechanism 1 utilizes a combination of a reporter dye having a specific and fluorescence response proportional to a change in metabolite concentration, where that metabolite has a direct stoichiometric relationship to a change in glucose concentration. Mechanism 1 also utilizes a marker dye, that is stable but unresponsive to changes in glucose and is used explicitly to produce a reference signal. In this case, the marker dye is used as a reference wavelength for the reporter dye, which changes emission at only one wavelength in response to glucose. An example of a suitable marker dyes includes the class of coumarins, which fluoresce in the blue region of the spectrum and localize in the cytosol of the cell, but do not respond to a change in glucose or metabolite concentration. In certain embodiments, the reporter dye can be located in the cytosol of the cell, and the marker dye can be in a different cellular compartment. One skilled in the art of photochemistry (including synthetic organic chemistry) can readily synthesize derivatives of these dyes that have these altered properties. For example, alkyl coumarins maintain the fluorescent properties of the coumarin parent but localize in the membranes of cell.

Figure 9A:
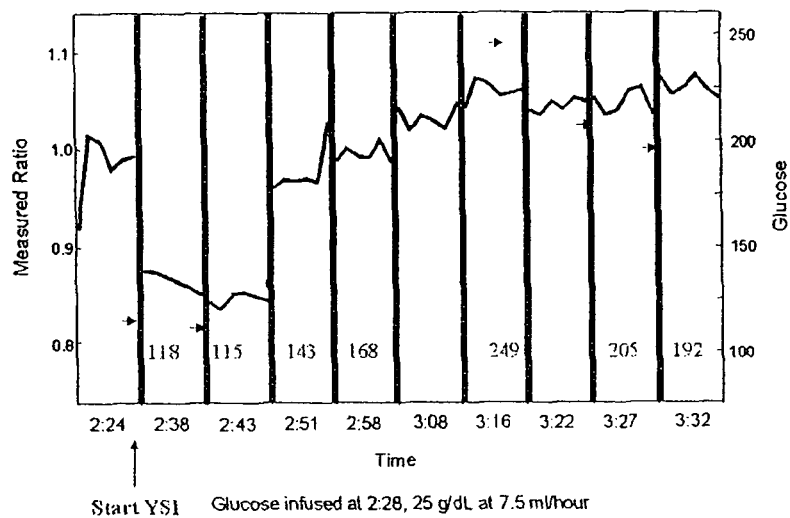
FIG. 9A and FIG. 9B are schematics showing blood glucose concentration results determined for actual versus measured SMMR ratios for a timed rat-clamp study. Blood glucose concentration determination using measured fluorescence ratio versus blood D-glucose ranges from 118 to 249 mg/dL blood D-glucose concentration obtained using the YSI method (YSI Incorporated, PO Box 279, Yellow Springs, Ohio 45387 USA) (FIG. 9A). Glucose is infused at 2:28, 25 g/dL at 7.5 ml/hr. The results of this study are plotted in FIG. 9B on a standard Clarke Error grid showing all data points from the experiment in Region A (center diagonal labeled "A") having 6.76% total error, 1 sigma. As shown, the Clarke Error grid analysis divides the correlation plot into five regions. Region A represents glucose values that deviate from the comparative value by <20%, or are <70 mg/dL when the comparative value is <70 mg/dL. The B regions (broader center diagonal labeled "B") represent values that deviate by greater than 20%, and if heeded would lead to benign treatment. Deviations within Regions A and B are considered clinically acceptable. Region C (mid-axis near top and bottom labeled "C") values are described as those deviations that would overcorrect an acceptable glucose. Region D (mid-axis left and right labeled "D") consists of those deviation values that would result in a dangerous failure to detect and treat a blood sugar condition. Region D values below 70 mg/dL are particularly common among the majority of consumer use glucose measurement devices. Many home blood glucose meters have up to 20% of data points in the D region. Region E deviations (left vertical and bottom labeled "E") are described as those points that if heeded would result in a potentially erroneous and dangerous treatment.
Figure 9B:
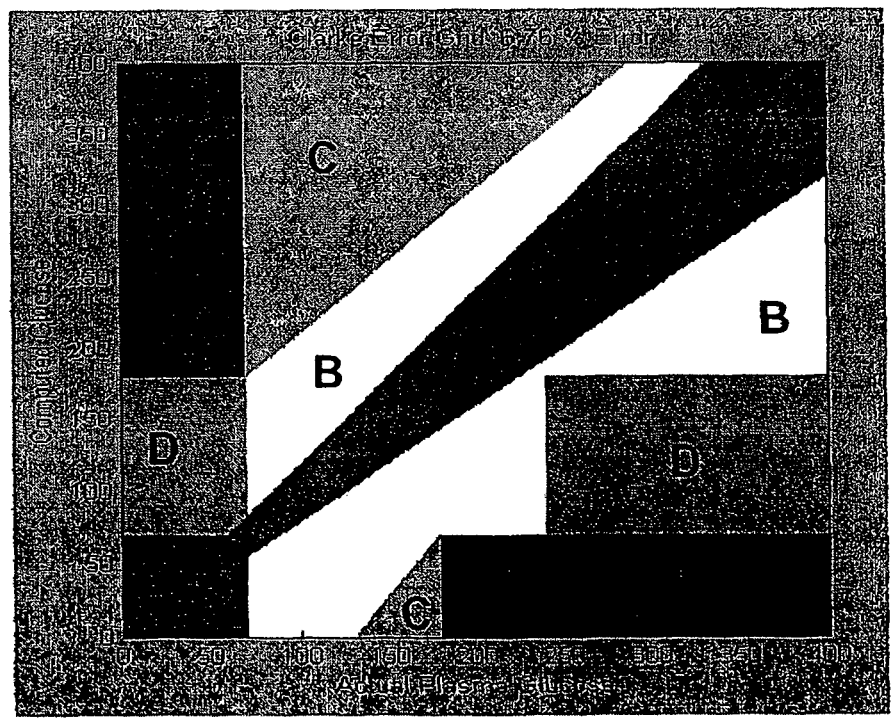
Figure 11:
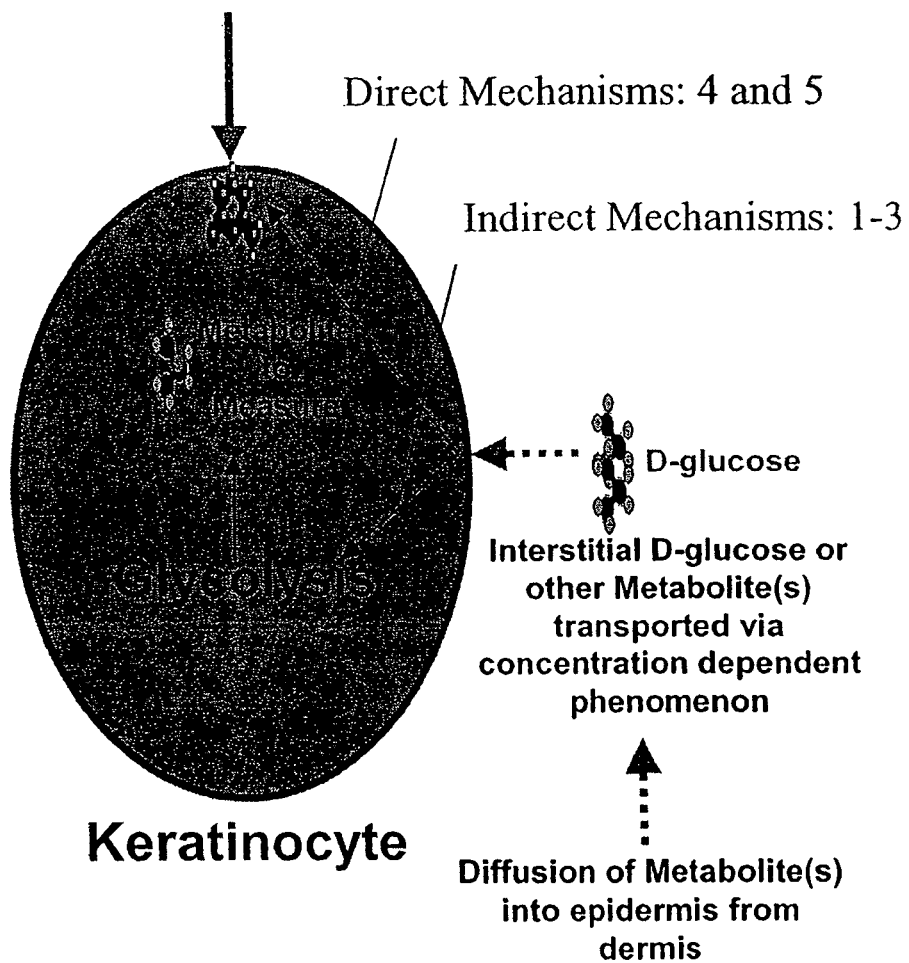
FIG. 11 is a schematic showing the placement of at least one SMMR into a keratinocyte. SMMRs are added to the skin surface with, e.g., a disposable patch, and are passively or actively transported to a keratinocyte. Indirect Mechanisms 1-3 and Direct Mechanisms 4-5 for fluorescence measurement are further detailed in FIGS. 12-16.

Alternatively, the sensor composition can include a dye that exhibits a wavelength shift in absorption or fluorescence emission in the presence of a metabolite, such as, for example, glucose. In this second case, Mechanism 2, only one dye is used that has two wavelengths where fluorescence signal varies with the introduction of D-glucose concentration to living cells (i.e., a first emission wavelength of the fluorescence spectrum increases with glucose, while a second emission wavelength decreases). The ratio of the first and second emission wavelengths can be determined, thereby allowing the selected dye to act as a self-referencing reporter. This phenomenon is illustrated in FIGS. 3-5, and 8 with analytical results demonstrated in FIG. 9. The mechanisms by which SMMRs report on the rate and quantity of metabolic activity, particularly glycolytic processes for the invention are described herein.

Prediction of Blood Glucose from Skin Glucose

The fluorescence measurement of extracellular and intracellular reporter molecules placed into the cytosol, nucleus, or organelles of cells within intact living tissue will track the concentration of blood glucose in an organism. When any one of a series of analytes or metabolites is measured using this technique, the molar concentration of blood glucose can be calculated. Fluorescence measurements of metabolite reporters described for this invention in a metabolic pathway of interest can be taken from one or more of the following parameters: pH (e.g., as lactate/H+); redox potential; NAD(P)H (nicotinamide adenine dinucleotide phosphate, for the reduced form using energy transfer); $FAD^+$ (flavin adenine dinucleotide, for the oxidized form using energy transfer); ATP/ADP ratio; $Ca^{2+}$-pumping rate; $Mg^{2+}$-pumping rate; $Na^+$-pumping rate; $K^+$-pumping rate; and redox potential of mitochondrial and other cellular membranes.

Previous studies have demonstrated that the lag time between blood glucose levels and glucose levels in non-perturbed epidermis is 2.9 to 4 percent per minute for the differential concentrations. Thus, the time required for the epidermis to reach an equilibrium with blood glucose at steady-state is 25 to 35 minutes as described by K. Jungheim and T. Koschinsky Diabetes Care 25(6), 956, 2002; and J. Ellison et al. Diabetes Care 25(6), 961, 2002. When blood glucose is rapidly increasing (hyperglycemia) or decreasing (hypoglycemia), this lag time becomes a critical issue for determining the response of any blood glucose monitor.

Thus, a rapid response is required for identifying important health related changes in glucose level and to avoid critical blood glucose scenarios. In one embodiment, issues of rapid response are addressed by using elevated temperatures at the measurement site to increase blood flow to these regions. The sensors are calibrated by comparing actual blood glucose to the sensor output. The zero and slope of the sensor calibration are determined by measuring an initial glucose level and a later glucose level to determine the change in glucose. The sensor calibration is then measured as $[G]=K_1$(sensor response)$+K_0$. The $K_1$ and $K_0$ values are entered into the sensor and calibration is checked against a reference standard material. The reference standard material is comprised of a matrix, which responds to glucose concentration in such a way as to provide primary standard concentration and response data.

In addition, the measurement of temperature may be combined with direct or indirect fluorescence measurements of glucose using one or more of the following parameter measurements: pH (as lactate and/or $H^+$); redox potential; inorganic phosphate ($P_i$); glycogen; pyruvate; nicotinamide adenine dinucleotide phosphate, oxidized form (NAD(P)$^+$); nicotinamide adenine dinucleotide (phosphate), reduced form (NAD(P)H); flavin adenine dinucleotide, oxidized form (FAD$^+$) for energy transfer; flavin adenine dinucleotide, reduced form (FADH$_2$) for energy transfer; adenosine triphosphate (ATP); adenosine diphosphate (ADP); the ATP/ADP ratio; $Ca^{2+}$-pumping rate; $Mg^{2+}$-pumping rate; $Na^+$-pumping rate; $K^+$-pumping rate; oxygen ($O_2$) utilization and vital mitochondrial membrane stains/dyes/molecules fluorescence response. These analytes measured in skin using the techniques taught herein give a complete picture of epidermal skin glycolytic metabolism where local epidermal analyte (glucose) quantities are proportional to the concentration of glucose in systemic blood, specifically the capillary fields within the papillary layer of the dermis (corium). The control of temperature at the measurement site, or the additional measurement of temperature, can be useful to correct measured fluorescence for optical pathlength, vasodilation, perfusion, and local physiology.

The fluorescence response of the reporter protein is then related to blood glucose level by the relationships shown in equations M1 and M2. The action of a reporter meeting the requirements of this invention include those molecules that are reactive with glucose following the mechanisms described herein. The reporter (used singly or in combination) has an affinity for and a response to the presence of glucose in a quantity that is directly proportional to the concentration of glucose within the individual cells or interstitial fluids, including blood. All such reporters useful for this invention are preferably nontoxic, non-carcinogenic, non-teratogenic, and do not deleteriously affect the skin when exposed to ultraviolet light or natural sunlight. The reporters included in the present invention are highly fluorescent or absorptive, evenly dispersible in the cell and interstitial cell fluid, do not aggregate or agglomerate, and do not exhibit binding-dependent fluorescent efficiency and quantum yields. Preferably, the reporters do not inhibit or restrict normal cell metabolism nor adversely affect cell viability or health in the concentrations and manner used.

Indirect measurement of blood glucose concentration is made as follows. A first molecule that exhibits no fluorescence or absorptive change with a change in glucose or other specific metabolites (i.e., the marker molecule) and a second molecule that exhibits direct changes in fluorescence intensity with a change in glucose (i.e., the reporter molecule) are measured individually. The molecules are safe, relatively permanent, and non-absorbing into the dermal tissue. Individual molecule fluorescence intensity measurements are ideally made using an ultraviolet or visible light emitting diode (LED) or laser diode for an excitation source or an equivalent known to those skilled in the art. The emission detector collects the light from the emission of the molecule signal within the skin and calculates the ratio of reporter dye fluorescence or absorption (following a predetermined lag time as lagt) to the marker dye fluorescence or absorption (following the same lag period lagt). A linear univariate computational formula for calibrating such an analyzer for blood glucose is given in equation M1 as:

$$[Glucose_{Blood}] = k_4 \times \frac{\text{Reporter } signal_{lagt}}{\text{Marker } signal_{lagt}} + k_o \quad (M1)$$

where $k_1$ is the regression coefficient (slope) for the line describing a change in fluorescence or absorption signal for the Reporter to Marker ratio versus glucose concentration in the blood, and $k_0$ is the calibration line intercept. Additionally, a change in glucose concentration over a time interval from $T_1$ to $T_2$ involves the following relationship shown in equation M2:

$$\Delta[Glucose_{Blood}] = k_4 \times \frac{\text{Reporter } signal_{lagt}(T_2 - T_1)}{\text{Marker } signal_{lagt}(T_2 - T1)} + k_o \quad (M2)$$

where $\Delta[Glucose_{Blood}]$ represents the change in blood glucose concentration and the terms $(T_2-T_1)$ represent the change in reporter or marker dye fluorescence or absorption over the time interval measured.

The dyes described within this invention may also exhibit an exponential relationship between fluorescence or absorption intensity and glucose concentration such that the computational formula for calibrating such an analyzer for blood glucose is given as equation M3:

$$[Glucose_{blood}] = k_0 e^{k_1 R} \quad (M3)$$

where R is the ratio of Reporter $signal_{lagt}$ to Marker $signal_{lagt}$.

Once activated, the response of the tissue cells to metabolite content or metabolic state is monitored directly using an optical reader. The optical reader calculates the tissue response to metabolite levels, applies first principles mathematical models to the response, and provides a determination of the organ, system, or organism metabolite levels.

A quality value is simultaneously calculated, which tells the user the quality of the measurement taken and of the resultant metabolite value reported. Based on this quality value, the user may be instructed to make one or more additional measurements until the quality value is indicative of an accurately reported metabolite value result.

It should be noted that an extension of this embodiment is the addition of other reporters, which are allowed to penetrate more deeply into the tissue; in some cases penetrating as far as 300 μm of the tissue. In some applications, reporters may be applied into the deeper layers of tissues and organs. In other embodiments of this invention, injection or ingestion of reporters into the bloodstream, or into specific organs or tissues may be utilized and the resultant fluorescence or absorption response measured at the site of application using an optical reader having remote optics.

Figure 24:
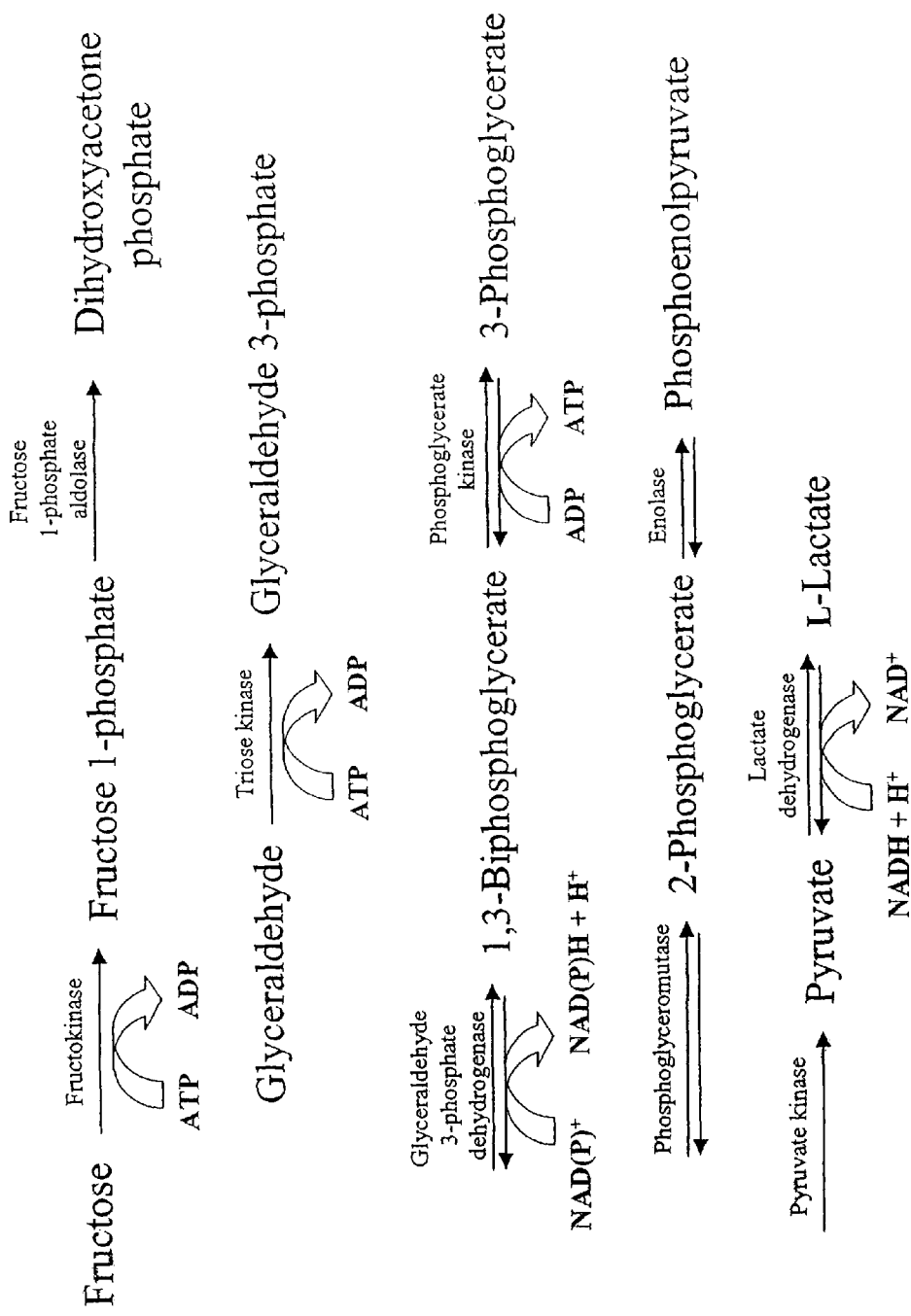
FIG. 24 is a schematic showing fructose metabolism.
Figure 25:
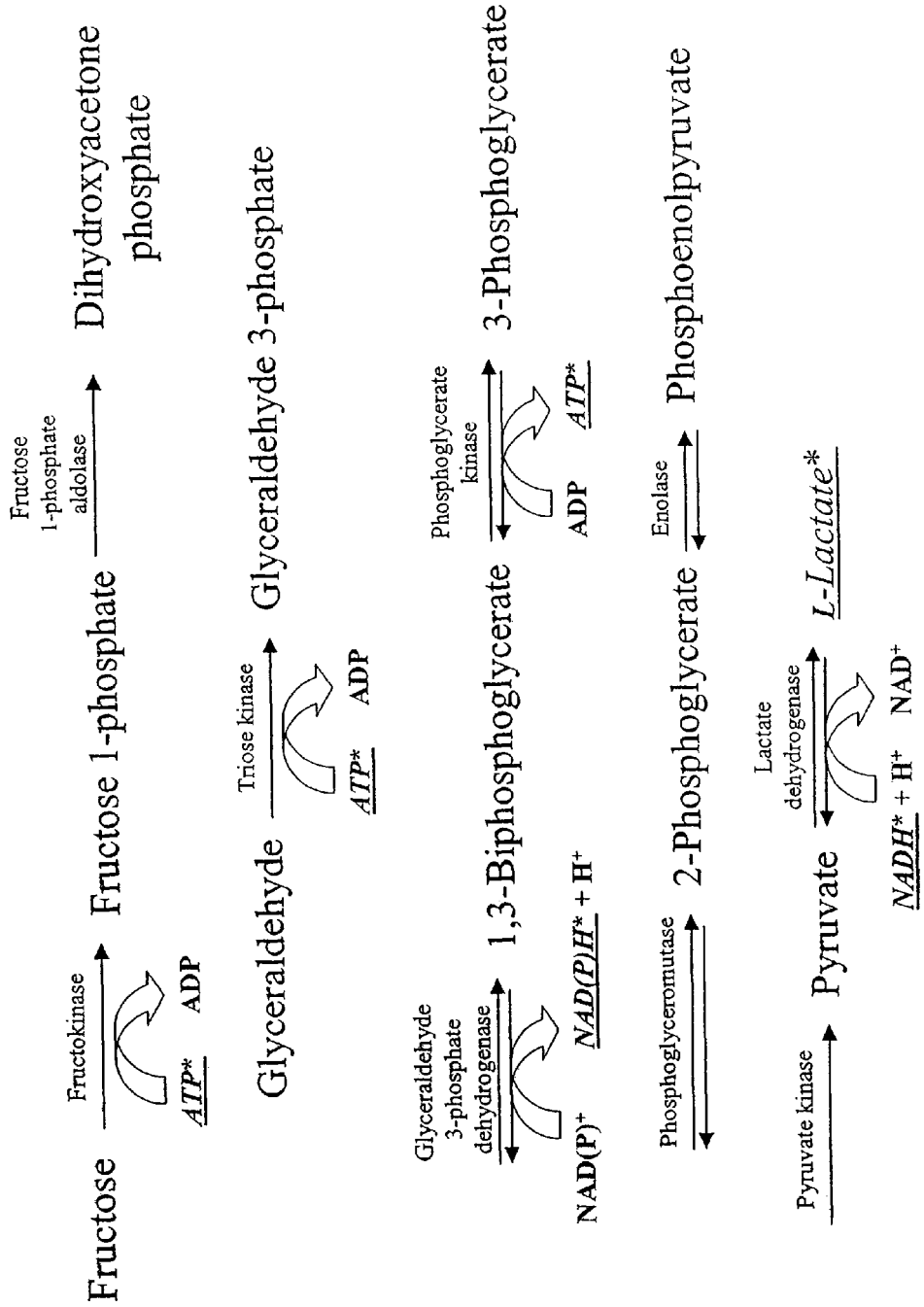
FIG. 25 is a schematic of fructose metabolism showing the specific analytes where glucose measurements are made for the invention, shown as bold, underlined and italicized*. SMMR are used by measuring glucose directly, or by measuring metabolites as indirect indicators of the quantity of glucose entering the cellular glycolytic pathway. Such metabolites are described in detail for the invention and examples are given here as: reducing equivalents molecules (e.g., NAD(P)H, NADH, FAD, $FADH_2$); changes in ATP-driven processes (e.g., cation pumping, transport at membranes, membrane reduction-oxidation electric potential, and pH gradient); and stoichiometric products of glucose utilization in glycolysis (e.g., lactate, hydrogen ion, pH, and pyruvate)
Figure 26:
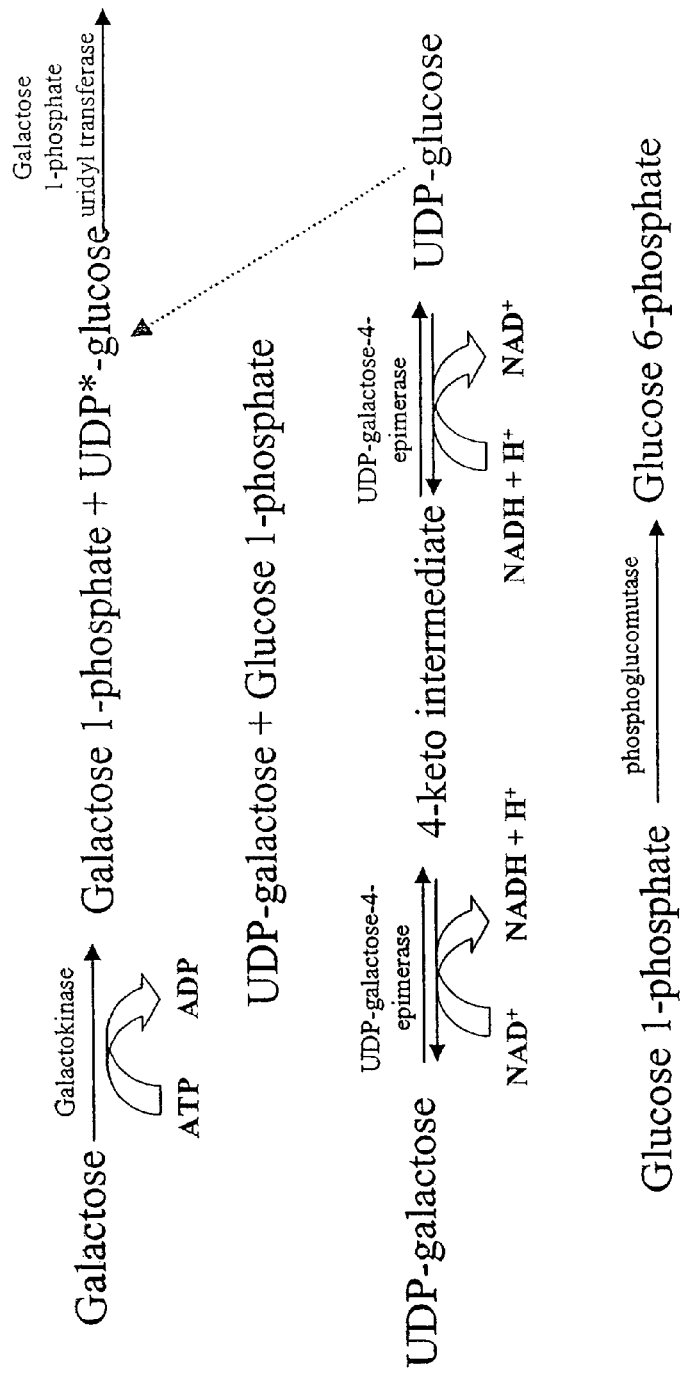
FIG. 26 is a schematic showing galactose metabolism.
Figure 27:
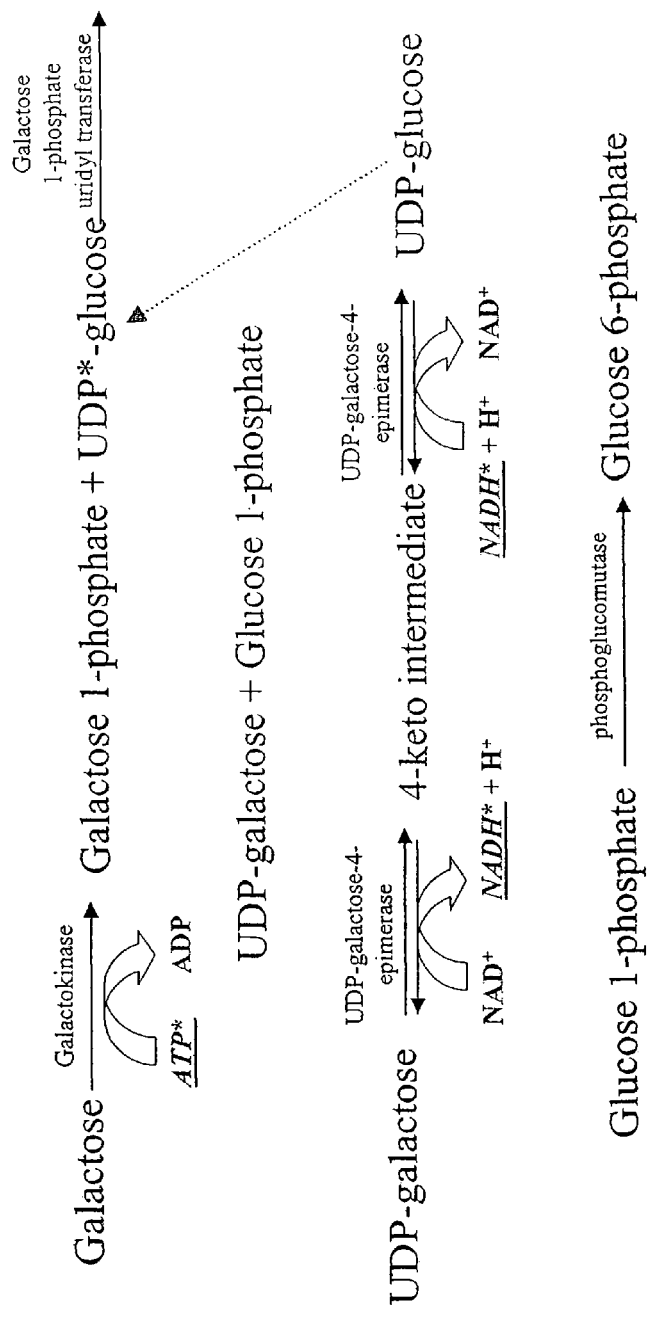
FIG. 27 is a schematic of galactose metabolism showing the specific analytes where glucose measurements are made for the invention, shown as bold, underlined and italicized*. SMMR are used by measuring glucose directly, or by measuring metabolites as indirect indicators of the quantity of glucose entering the cellular glycolytic pathway. Such metabolites are described in detail for the invention and examples are given here as: reducing equivalents molecules (e.g., NAD(P)H, NADH, FAD, $FADH_2$); changes in ATP-driven processes (e.g., cation pumping, transport at membranes, membrane reduction-oxidation electric potential, and pH gradient); and stoichiometric products of glucose utilization in glycolysis (e.g., lactate, hydrogen ion, pH, and pyruvate)
Figure 31:
FIG. 31 is a diagram demonstrating the mechanism of action for lactate reporters.
Figure 34:
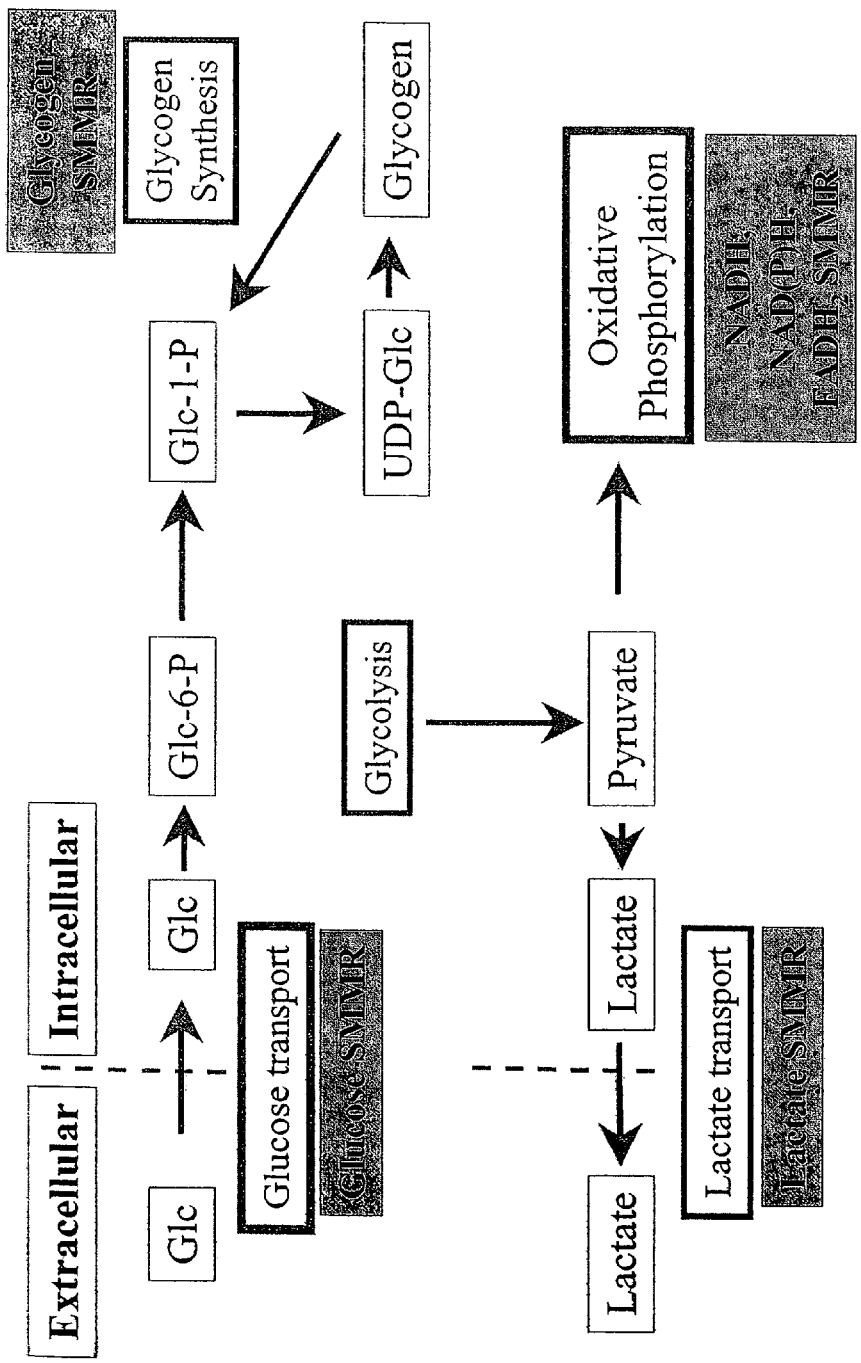
FIG. 34 is a schematic showing the use of SMMRs to establish analytical methods for measurement of each glucose pathway for a variety of cell types.
Figure 35:
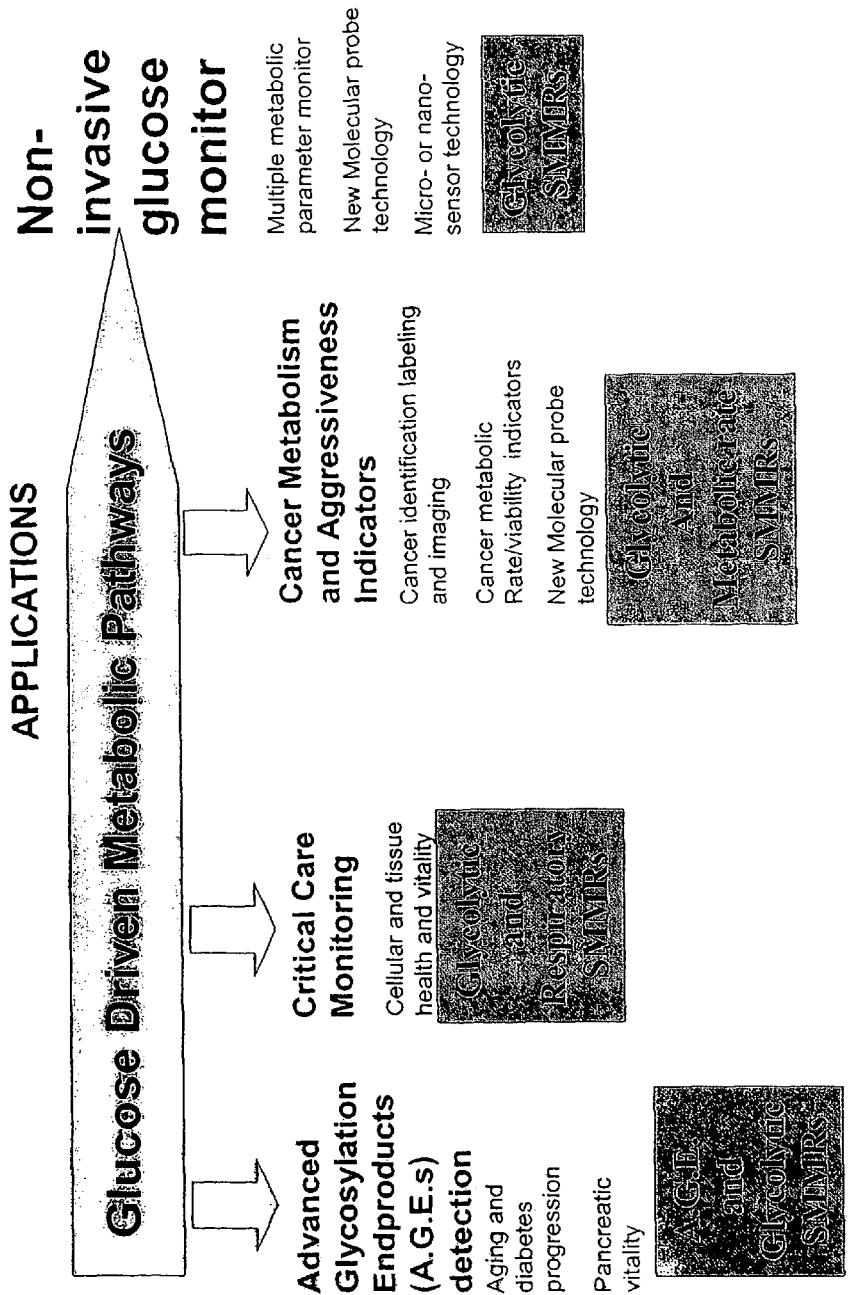
FIG. 35 is a diagram summarizing various applications using the SMMRs of the invention.
Figure 37:
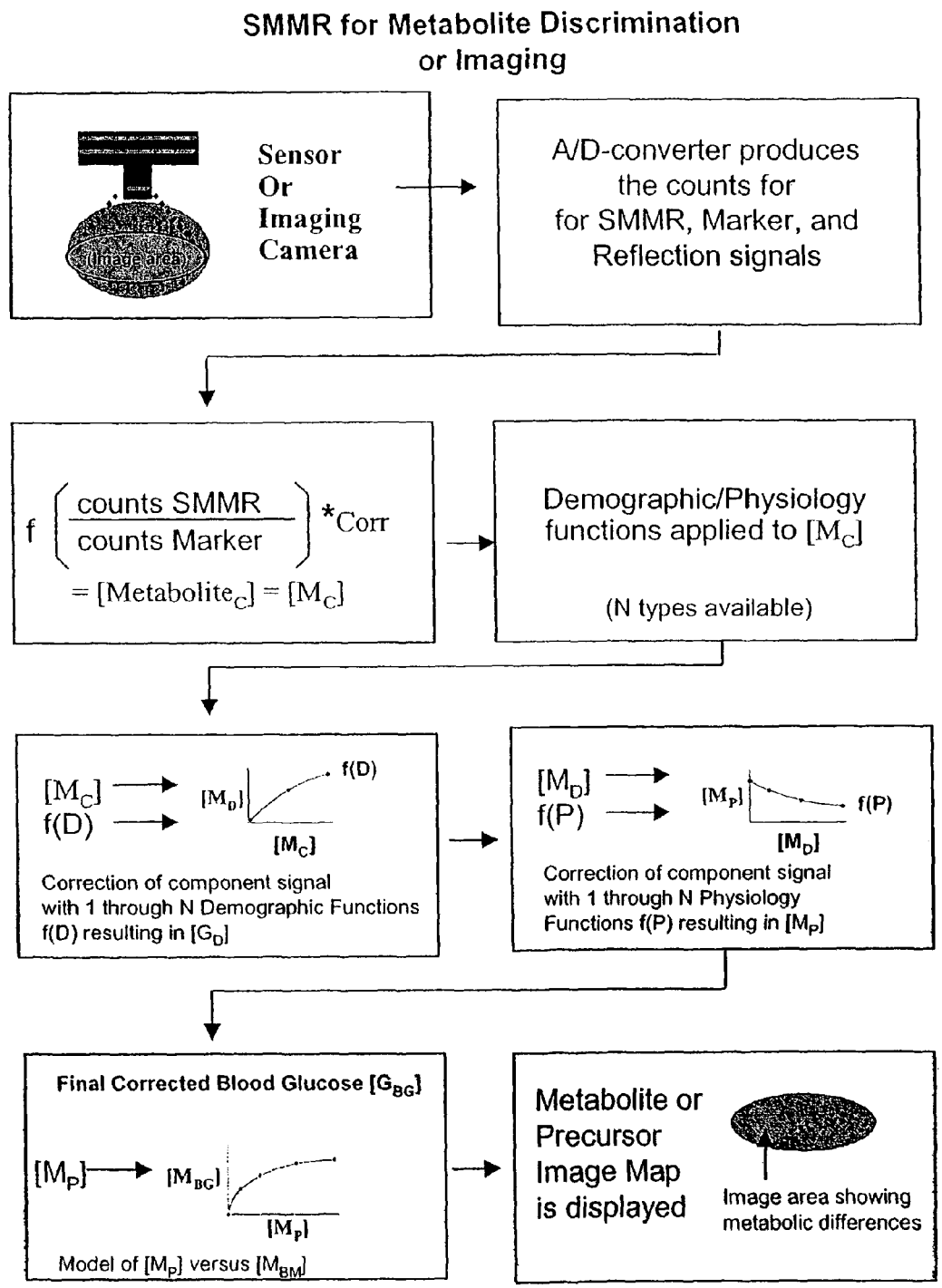
FIG. 37 is a schematic showing how to use SMMRs for metabolite or precursor discrimination or imaging (i.e., qualitative measurement)

Those skilled in the art will recognize that FAD and $FADH_2$ are formed in the citric acid cycle during aerobic (oxidative) biosynthesis and are used for electron transport in this pathway. FIG. 24 shows anaerobic glycolysis, where NAD(P)H is the major electron donor for reductive biosynthesis.

The invention also provides SMMRs that are combined with a small reagent strip in order to calibrate a sensor used for direct in vivo, non-invasive glucose measurement. This calibration strip is used for a single reaction to adjust the glucose sensor response and is then depleted. Each calibration ideally requires a new calibration strip for adjusting the sensor response. Those skilled in the art will appreciate that such a reagent strip can be used to detect glucose in fluids withdrawn from the body.

Cellular Respiration

The implications and status of cellular respiration can be determined by molecular oxygen consumption. The classic method for determining oxygen consumption in living organisms is to cut small pieces of living tissue and study respiration rate using a Fenn-Winterstein type respirometer (See Wennesland, R., Science 114: 100-103, 1951). This method has obvious drawbacks for day-to-day monitoring of human subjects. Thus, SMMRs that detect oxygen levels are also provided.

Some tissues and organisms vary widely in respiration rate. The respiration rate is also known to vary with cell size in terms of surface area-to-volume ratio. Oxygen consumption is proportional to cell surface area. When overall cell size increases, respiration rate decreases. The respiration rate of a tissue or whole organisms is the arithmetic sum of the rates of its component cells. Metabolic rate changes for some cell types may vary by a factor of 100 as a function of cell activity levels. Temperature affects respiratory rate such that a 10° C. rise in temperature increases rate by 2 to 4 times. Oxygen partial pressure and water concentration also affect respiration rate, but only when levels are abnormally high or low.

Redox Potential and Ion Pumping

Reduction potential in cells, tissues, and organisms is indicative of glycolytic activity and respiration health of cells, tissues, and whole organisms. Direct measurement of intracellular redox potential in cells indicates mitochondrial health and levels of aerobic (i.e., increased mitochondrial activity due to oxidative phosphorylation, reduction or cessation of lactate production, increased oxygen consumption) versus anaerobic respiration (i.e., cessation or decrease in mitochondrial activity due to inhibited oxidative phosphorylation, as well as increased lactate production, and decreased oxygen consumption). These indicators yield direct ability to assess the health state of cells in real-time.

Biochemical reactions for respiration, glycolysis, and other basic metabolic processes require the transfer of electrons from one molecule (or atom) to another. These are termed oxidation-reduction (redox) reactions. Oxidation is a term used to denote loss of electrons from a molecule, whereas reduction is the term used to denote a gain of electrons in a molecule. Electrons are neither created or destroyed in redox reactions and, thus, when one molecule is oxidized, another is reduced. The transfer of a single hydrogen atom is equivalent to a transfer of one proton and one electron.

Many important redox reactions that occur in living systems involve the transfer of hydrogen rather than the transfer of isolated electrons. The affinity of a molecule to accept electrons is termed its reduction potential, and when measured under standard conditions it is denoted by the symbol ($E_0'$). Reduction potential is measured in volts (V) on a scale relative to a value of 0.0 V for the half-reaction of hydrogen at standard conditions (i.e., 1 atmosphere pressure, 1 molar concentration of reactants, and 25° C.). Values for the redox potential in living cells may vary because the reactants are not normally at 1 M concentration. A positive redox potential indicates that a molecule has more affinity for electrons than the hydrogen ion ($H^+$). Furthermore, in redox reactions electrons move toward the molecule with a positive reduction potential.

In redox reactions, the total electric potential or voltage change ($\Delta E$) is equal to the arithmetic sum of the individual oxidation or reduction steps. The voltage change can also be denoted as equivalent to a change in the chemical free energy ($\Delta G$). This chemical free energy is calculated using a constant specifying the charge in 1 mole of electrons as 96,500 joules per volt, referred to as the Faraday constant ($\mathfrak{F}$). It should be noted that the oxidation potential is simply the negative value of the reduction potential. A positive $\Delta G$ indicates a reaction will not occur spontaneously, however in biochemical reactions, a positive $\Delta G$ reaction is often coupled with a negative $\Delta G$ reaction of greater magnitude, thus the reaction proceeds.

Biological reduction-oxidation (redox) potential ($E_0$) is affected by the presence of molecular oxygen ($O_2$) and by hydrogen ion concentration, which is measured as pH. Many cellular redox reactions, such as those in glycolysis, involve electron transfer and hydrogen transfer. In these reactions, $E_0$ (the reduction potential, in volts) changes with pH. An increase in pH creates a decrease in $E_0'$ (the standard reduction potential) whenever the concentration of the oxidant equals the concentration of the reductant. See, Hewitt, L. F., Oxidation-Reduction Potentials in Bacteriology and Biochemistry, $2^{nd}$ Ed. Williams & Wilkins, Baltimore, Md., USA, 1950.

Dyes have been proposed as an in vitro means for measuring redox potential in living cells. However, such dyes have not been used or specified for use to indicate in vivo metabolic pathway delineation in living organisms for the expressed purpose of assessing health and well-being of tissues or organs. Furthermore, in vitro dyes using absorption spectroscopy are typically less sensitive by two orders of magnitude to metabolic changes compared to fluorescent. Current commercial absorption and fluorescent dyes have not been optimized for molecular characteristics. Thus, they are not optimal for use in non-invasive, in vivo monitoring of metabolic conditions derived from in situ measurements made on living subjects.

Previous work with in vitro dyes and fluorophores used in cell or tissue cultures has specified that, in order to use these dyes for in vitro membrane potential measurement of cells, one must determine: (1) the reduction potential ($E_0$), (2) the standard reduction potential ($E_0'$), and (3) the titration curves for each oxidizable dye used (See, Giese, A. C., 1973, Cell Physiology, $4^{th}$ Ed. W.B. Saunders Company, Philadelphia, pp. 420429). In this invention, a specific SMMR is designed such that when the SMMR comes in contact (in vivo and in situ) with the analyte or metabolite of interest, the appropriate optical response occurs. Preferably, this optical response is fluorescence, but alternative absorption mechanisms are not excluded where signal is sufficient for measurement using low-cost instrumentation.

SMMR have the above basic properties as well as the ability to be applied locally and topically, in trace quantities (from about 10 to about 400 μL of a 1 to 50 μM mixture), using a small molecule in solvent solutions that are transparent to visible light, and that have a pre-specified temporary residence at the application site (from about 5 seconds to about 30 days).

As noted, a negative reduction potential indicates a substance has lower affinity for electrons than hydrogen ($H_2$), whereas a positive reduction potential indicates a substance has higher affinity for electrons than $H_2$. Thus, the coenzymes NADH, NAD(P)H, and $FADH_2$ are strong reducing agents and have negative reduction potentials. Molecular oxygen ($O_2$) is a strong oxidizing agent having a positive reduction potential. NAD(P)H, NADH, and $FADH_2$ are coenzymes acting as reducing agents and have electron transfer potential useful for providing electrons for biological metabolic pathways. The electron transfer potential is converted to phosphate transfer potential ($\Delta G^0$) in the form of ATP. In redox reactions, an oxidized form of a substance ($X^+$) and a reduced form ($X^-$) make up a redox couple. Therefore, NAD(P)H, NADH, and $FADH_2$ can be detected using reporters of the invention for sensing either energy transfer or redox potential. The energy transfer for these coenzymes is demonstrated in FIG. 29 and the redox potential measurement is made as illustrated in FIG. 30. The redox potential is measured at the inner mitochondrial membrane.

In energy transfer measurements using SMMR methodology, external energy from a handheld sensor is applied to target cells containing naturally occurring fluorophores such as the coenzymes NADH, NAD(P)H, or $FADH_2$. A small molecule metabolic reporter is added to the target tissue to provide an energy transfer vehicle for enhancement of fluorescent yield and efficiency. The excitation energy is absorbed by the natural fluorophore and emitted at the absorption frequency of the reporter. The reporter, in turn, emits enhanced signal at a pre-specified frequency. This emission frequency is preselected in order to be compatible and non-interfering with respect to other measurements made sequentially at the same target tissue site. Thus, the amplification factor and emission wavelength of the reporter can be optimized for the measurement regime selected.

The implications of measuring intracellular redox potential (whether or not combined with other metabolites or ions) in living cells in vivo using SMMRs include, but are not limited to, the following:

A) Research in mammals has shown that orthotopic liver transplantation is associated with significant variations over time in the redox potential of the cytosol. Postoperative mortality is related to redox state of the liver cell mitochondria. Research has suggested that abnormal tissue oxygenation can occur during liver transplantation (A. de Jaeger et al., Intensive Care Medicine, 24(3): 268-275, 1998). Thus, the physician would choose to monitor both intracellular oxygenation and mitochondrial redox state both during and after transplant surgery. SMMRs can be used to monitor both intracellular oxygenation and mitochondrial redox state using both an intracellular tissue oxygen reporter and a mitochondrial redox reporter.

B) According to the literature pertaining to emergency medicine, a variety of pathogenic mechanisms of cellular injury occur during shock in humans. See, e.g., Jeffrey A. Kline MD, Pathogenic mechanisms of cellular injury during shock, May 8, 2001, Society for Academic Emergency Medicine Annual Meeting, Atlanta, Ga., oral abstract presentation found at http://www.saem.org/download/01kline.pdf. Such cellular metabolic changes include, e.g., (1) a transformation of cells from fatty acid to carbohydrate utilization, (2) an increase in lactate production in cells due to metabolic conversion from aerobic to anaerobic glycolysis, and (3) an overall decrease in ATP production with a resultant decrease in calcium ion pumping and associated ATP driven processes. An advanced stage of injury moving to shock in humans involves a hypoxic condition occurring in mitochondria of affected cells, which creates (a) a cessation of pyruvate oxidation, (b) a cessation of calcium ion pumping and ATP production, and (c) a leaking of electrons across organelle and outer cellular membranes. Further metabolic stress leads to lactic acidosis, a drastic change in intracellular redox potential, and increased leakage of calcium ion into the cytosol. SMMRs enable direct measurement of real-time changes in the concentrations of intracellular lactate, calcium ion, and redox potentials in affected cells and tissues. This information allows real-time detection of changes at the cellular level and would provide rapid information relative to organ or whole organism health status for critical care monitoring.

C) In the case of cardiac muscle under stress, the muscle cells exhibit rapid changes in glycolysis, oxygen consumption, lactic acidosis, drastic changes in intracellular redox potentials, and changes in intracellular versus extracellular calcium ion concentrations within cardiac muscle cells. Again, SMMRs enable direct measurement of real-time changes in the concentrations of intracellular lactate, calcium ion, and the redox potentials in affected muscle cells and tissues. This information can provide immediate detection of changes at the cellular level for cardiac subject monitoring and would provide rapid information relative to health status for critical care monitoring.

D) Intracellular calcium ion ($Ca^{2+}$) performs critical functions in muscle contraction, nerve impulse transmission, ion transport, and transmission of signals across membranes. For normal cells, the concentration of extracellular and intracellular calcium is closely regulated. A perturbation in normal calcium ion balance is indicative of metabolic stress, pre-shock, cell viability concerns, and cell mortality. SMMRs provide direct concentration information regarding intracellular and extracellular calcium ion levels.

In addition, the measurement of electric oxidation-reduction potential across cell membranes in vivo is an accurate indirect indicator of glucose quantities entering the cell to fuel glycolytic processes. SMMRs reporting on changes in membrane potential are attached to cell membranes including the inner and outer cell membranes, the nuclear membranes, as well as those of organelles, such as mitochondrial membranes. Membrane potential measured in skin cells using the techniques taught herein give a complete picture of epidermal skin glycolysis.

Specific SMMRs, e.g., those acting as vital mitochondrial membrane stains, require that a fluorescence response occurs upon a change in membrane potential. Several fluorophores are know to comply with this requirement. These fluorophores behave in such a way as to change fluorescent intensity and emission spectral line shape in response to changes in mitochondrial membrane potential. In the present invention, an increase in intracellular glucose concentration increases the mitochondrial membrane potential and causes additional SMMR units to attach to the inner mitochondrial membrane. This increased SMMR binding to the inner membrane causes fluorescence quenching of the SMMR proportional to changes in glucose concentration. This response is based upon the interaction of the redox coupling of $NAD^+$ and NADH, $NAD(P)^+$ and NAD(P)H, FAD and $FADH_2$, and ion transport. Thus, optical flux changes detected by a hand-held sensor provide detailed information regarding intracellular redox potential at the mitochondrial level suitable for an assessment of cell health and well-being. Reversible interaction between the SMMR and the mitochondrial membrane allow real-time monitoring of these processes.

Traditional redox potential sensors involve electrodes and invasive procedures. Moreover, these instruments measure analytes present in solution and are not able to detect intracellular activity in a non-invasive manner. In contrast, SMMRs yield a direct, real-time measurement of intracellular activity relative to cellular metabolism, as well as a measurement of the direct state of health of tissues as compared to buffered solutions surrounding tissues. Immediate and real-time information of the intracellular metabolic state gives a more rapid and accurate indication of organism health for diagnostic-based, corrective treatment.

Diagnosis of Disease State

Many disease states in cells and organisms affect a host's/subject's metabolic condition and efficiency. Thus a non-invasive, in vivo method for directly measuring intercellular and intracellular metabolic changes in tissues and organisms is valuable in assessing health versus disease or stress state conditions of cells, tissues, and whole organisms.

Metabolic disease states may be monitored using the reporters of the invention by: (1) measuring NADH, NADPH, and FAD using energy transfer fluorescence measurements (to validate the presence of coenzyme activity as an indication of glucose metabolism) and (2) measuring cellular reduction-oxidation potentials (indicating cellular activity); lactate formation (indicating anaerobic glycolysis in the stress state); calcium ion pumping (as an indication of ATP availability); and oxygen consumption (indicating healthy cellular respiration and aerobic glycolysis). Metabolic diseases affecting cellular respiration, ion pumping, and energy production can be monitored non-invasively for cells, tissues, organs, and systems using SMMR technology, as described herein.

Cationic transport diseases include, but are not limited to, potassium-channel disease affecting heartbeat, epileptic tendencies, and deafness. Sodium-channel disease can result in, e.g. muscle spasms, or osmotic imbalance leading to hypertension.

The onset of disease states affecting metabolism of glucose, accumulation of lactate, deficiencies in ion pumping and ATP formation, and changes in oxygen consumption can be detected in real-time using SMMRs. The SMMRs are synthesized or constructed with unique and specific molecular properties, such that a known optical signal is produced when the SMMR is reacted with precisely identified metabolites or precursors. The resultant optical flux is an indication of the in vivo health, stress, disease state, or necrotic conditions of tissues and organ systems. Specifically, abnormalities in glucose utilization from anaerobic or aerobic glycolysis can be identified using SMMRs, as illustrated in FIGS. 22-27 and 34, according to the mechanisms described in FIGS. 29-33, and 10.

For example, the details for glycolytic metabolism can be identified using SMMR technology. Examples include the cellular utilization of glucose, fructose, and galactose. Metabolic disease conditions related to glycolysis include diabetes mellitus (a disease condition related to insulin regulated glucose transport or utilization/response deficiency); essential fructosuria (a deficiency in fructokinase); hereditary fructose intolerance (a deficiency in aldolase B); and hereditary fructose-1,6-biphosphate deficiency results in hypoglycemia, apnea, hyperventilation, ketosis and lactic acidosis due to impaired hepatic gluconeogenesis. These symptoms can take on a lethal course in neonates. For galactose metabolism, a deficiency in Galactose-1-phosphate uridyl transferase, galactokinase, or UDP-galactose-4-epimerase results in galactosemia.

Deficiencies of normal metabolic activity related to glucose, fructose, or galactose metabolism can be detected in vivo by applying SMMRs to the target tissue and adding the appropriate sugar substrate molecules into the immediate target area where the SMMR has entered the cells. Tracking the metabolic rates using the SMMR in this manner allows the detection of a normal versus abnormal metabolic state. Moreover, this test is rapid and can be accomplished using low cost hand held sensors specific for the type of SMMR used.

Determination of Vitality and Viability of Cells Based on Metabolic Function

The health of cells can be determined based upon their normal utilization of glucose as well as by calcium ion transport (an ATP-driven cellular ion pump), ATP formation, lactate formation, redox state, electromotive potential, $NADH^+$ or $NAD(P)H^+$ or $FADH_2$ utilization, and oxygen consumption. For example, necrotic tissue relative to surgical procedures such as bowel resection; acute appendicitis; frost bite; septicemia; leprosy; restricted circulation; burns from heat, chemical, or radiation exposure; trauma damage to tissue; or any other condition where viability and vitality are essential considerations, may need to be assessed. There are a number of reporter molecules that when placed into tissue, provide precise information on cellular respiration, metabolic rate, relative health (vitality), and viability.

Healthy tissue performs a number of specialized and general functions that may form the basis of targeted SMMR technology. Specialized functionality includes, but is not limited to, the synthesis and utilization of biochemicals unique to that tissue. General functionality includes, but is not limited to, maintaining the integrity of the cell membrane, the utilization of glucose and other metabolic substrates, the synthesis of lactate in anaerobic tissue and the consumption of oxygen in aerobic tissue.

SMMRs may be diffused directly into cells and tissues to detect viability based upon active metabolism indicated by the presence of glycolysis, ion pumping, redox potential, lactate formation and accumulation, and oxygen consumption rates. Any of these metabolic indicators can all be measured using SMMRs as described in detail above. In addition, direct SMMRs are available for viability monitoring based on other cellular mechanisms.

Critical Care Monitoring

The viability and metabolic health of cells can be determined by oxygen consumption; by lactate formation; by calcium ion transport; by glucose metabolism; by ATP production and utilization; by NADPH, NADH or $FADH_2$ utilization; by measurements of electron transfer potential; and/or by measuring changes in both intracellular and extracellular resting potential. SMMRs allow detection and real-time tracking for each metabolite (analyte) and allows intracellular tracking of metabolic conditions.

Thus, SMMRs, combined with low-cost spectroscopic techniques, can provide the next generation of critical care monitoring. Advantages to the subject and physician include: (1) obtaining information directly from within the cells instead of looking at footprints, reflections or shadows of processes that affect or predict morbidity/viability, (2) exploiting the combination of new direct information with dramatic improvements in the time constants for either degradation or improvement of subject status, (3) exploiting the ability to differentially monitor central and peripheral tissues to better characterize subject status, and (4) monitoring the real-time effect of anesthesia and/or therapeutics at the intracellular level.

Skilled deployment of the SMMR/instrument platforms of the invention, which exploit these advantages, will improve subject outcomes at lower cost to the healthcare system while providing physicians with real-time cellular and organism status.

The current state-of-the art in critical care monitoring involves assessment of the status of selected parameters in blood, e.g., glucose and oxygen supply, and parameters such as pH and lactate for evidence of dysfunction at the cellular, tissue, and organ level. Because blood is highly buffered and in large volume, it is a poor source of early warning information and does not provide the opportunity to assess the metabolic state of cells, organs, or systems in real-time. Providing real-time intracellular status using appropriate SMMR/instrument technology (including the methods and compositions of the invention) can provide life-saving information to the critical care medical staff and can give appropriate and timely diagnostic warning for life saving actions.

When injury or stress occurs to a cell the electric potential changes. The magnitude of the change on electric potential is calculated using the well-known Nernst equation and simplified derivations thereof as follows in equation M4:

$$E = 59.5 \log_{10}\left(\frac{[e_h]}{[e_l]}\right) \tag{M4}$$

where E is the electric potential in millivolts, and $e_h$ and $e_l$ represent the higher concentration and lower concentration (molar) of the electrolyte, respectively. From this relationship, it is possible to calculate the ionic diffusion coefficients from measurements of electric potential from which molar concentration of transported ions can be determined. SMMRs are useful for measuring electric potential as well as direct ion concentrations.

There are multiple methods available to evaluate the type of stress occurring to a cell using SMMR technology of the invention. For example, lack of molecular oxygen ($O_2$) reduces the resting potential and changes the intracellular versus extracellular ion concentration. A decrease in heat liberation also occurs when the cell is under metabolic stress. Inhibition of any glycolytic function also reduces the resting potential. In fact, the potential may fall toward zero as poisoning or death become imminent. Both the potential and the ion transport effects can be calculated. The energy required to move 1M of cation from inside the cell to the outside of the cell for a single and two compartment cell is also calculated using modified forms of the Nernst equation shown in equation M5 and M6. See Giese, A. C., Cell Physiology, 4$^{th}$ Ed. W.B. Saunders Company, Philadelphia, pp. 571-582, 1973). The modified Nernst equation is as follows:

For the single cell (compartment):

$$W = \frac{RT}{\mathcal{F}}\left(\ln\frac{[A^+_{out}]}{[A^+_{in}]}\right) \tag{M5}$$

For the two cell (compartment)

$$W = \frac{RT}{\mathcal{F}}\left(\ln\frac{[A^+_{out}]}{[A^+_{in}]} + \ln\frac{[B^+_{in}]}{[B^+_{out}]}\right) \quad (M6)$$

where W is the energy required, $A^+$ and $B^+$ are cations, R is the gas constant (i.e., 8.312 joules per degree per mole), T is the absolute temperature in degrees Kelvin, and $\mathcal{F}$ is the Faraday constant (i.e., 96,500 coulombs per gram equivalent), and ln is the natural logarithm ($2.3 \times \log_{10}$).

Cancer Diagnosis, Detection, and Prognosis

Tumor cells engage in anaerobic glycolysis, as do epidermal keratinocytes, and thus metabolic activity differences between metastatic cells and normal cells are quite pronounced and obvious, because tumor cells are known to 1) have higher metabolic rates than normal cells, 2) accumulate dye molecules at higher levels than normal tissue, 3) have lower pH then normal tissue, and 4) frequently undergo glycolysis at much higher rates.

Current and commercial spectroscopic characterization of cancer cells is limited to discriminant analysis of raw spectroscopic data. These data yield limited signal-to-noise differences between metastatic and normal cells when applying measurements using molecular spectroscopy, or native autofluorescence and white light reflection. These techniques provide only weak differentiating power to distinguish cancerous tissue from normal surrounding tissue due to the low signal-to-noise molecular absorption, or autofluorescence signals within the metastatic versus normal tissues.

A large number of in vitro molecular probe/limited wavelength fluorescent microscope techniques for characterizing cancer cells are available. Simultaneously, dramatic improvements in the ability to separate, capture and present cancer cells for characterization are occurring. Thus, a technique that enables the selection and measurement of specific intracellular metabolic pathway signals would be valuable for distinguishing normalcy, malignancy, or pre-malignancy as the result of non-invasive, in vivo measurements. The necessary SMMR materials could simply be "painted" or sprayed onto the targeted area to discriminate malignant cells (i.e., hypermetabolic), or pre-malignant cells (i.e., semi-hyper-metabolic), from normal cells.

Cancer screening is often an invasive process. A number of techniques are currently utilized, including physical examination, biopsy, and some fluorescence imaging. Additionally, the drugs used for photodynamic therapy have been used to delineate cancerous tissue with some success. Photodynamic therapy has been used since the late nineteen fifties as an anti-cancer treatment. Briefly, a drug that selectively binds to tumor cells is applied either topically or intravenously. A red light is then shone on the tissue, and the drug generates active oxygen species that destroy the cells. Red light is most often used for the therapy, since it has an improved penetration into tissue. The drugs most commonly used in these therapies are porphyrins and common derivatives include hematoporphyrin, benzoporphyrin and commercial preparations such as photofrin that consist of mixtures of porphyrins and oligomeric porphyrins.

Porphyrins typically generate long lived excited states with a quantum yield of about 0.6. They fluoresce in the red region of the spectrum above 620 nm with quantum yields of about 0.1. In the blue region of the spectrum, they have large molar absorption coefficients of about $10^5$ $M^{-1}$ $cm^{-1}$ and some derivatives including benzoporphyrin and chlorophylls have similarly high molar absorption coefficients in the red. The molecules are extremely sensitive to their microenvironment and lose many of their photophysical properties when aggregated.

The photophysics of these molecules have assured their use as molecules to detect oxygen concentrations, to delineate cancer cells in vivo as well as their use in photodynamic therapy (PDT). As molecules to detect cancerous tissue, advantage is taken of their selective uptake by tumors. Typical uptake ratios for the dye in cancer versus normal tissue are about four to one. Provided that the molecule is monomerized once inside the cell, it can be detected by its fluorescence. However, there are a number of disadvantages associated with using porphyrins for this technology. The molecules are photosensitive and can be destroyed by the reactive oxygen species they generate. If the molecules aggregate inside the cell, they will not fluoresce. This aggregation is dependent both on the microenvironment of the molecule and on its effective localized concentration. Hematoporphyrin, for example, starts to aggregate in water at concentrations as little as 1 µM and is predominantly aggregated at concentrations above 10 µM. There is also a disadvantage in using the same drugs for therapy as for cancer detection in that the quantum yield of fluorescence of these compounds is not particularly high, as only about 10 percent of absorbed photons are returned as fluorescence.

The wavelengths used to excite the dye depend on the purpose of the treatment. For photodynamic therapy, red light is used since this gives the best penetration of scattering tissue. For detecting cancer cells, green or blue light is often used since the drug has a higher molar absorption coefficient at these wavelengths and light penetration is not an issue. See, Photochem. Photobiol. 73: 278-282, 2001.

The rational behind these techniques is that the cancer cell preferentially takes up the dye over normal tissue. Strictly speaking, it is not accurate to say that the dye selectively binds to the cancer cell. Dye uptake is more closely related to the fact that the cells have a higher metabolic rate. Truly selective uptake or binding would involve exploitation of some chemical difference in the metabolic pathways or genetic expression that a cancer cell demonstrates. For this reason, an unfortunate side effect of porphyrin type dyes is that normal tissue that has a high metabolic rate may preferentially accumulate the dye.

Malignant changes result in modified rates of metabolic activity and in cellular proliferation. These changes result in biochemical changes, which may be monitored using changes in autofluorescence. See Cancer Res. 62: 682-687, 2002; Photochem. Photobiol. 68: 603-632, 1998; Neoplasia 2: 89-117, 2000. However, the underlying problem behind all these techniques is that the autofluorescence is extremely weak and subject to interferences from photooxidation and variability in the spectral shape of the autofluorescence.

Cancer cells exhibit hyperglycolytic activity as compared to normal cells. In addition cells moving into the cancerous state covert glycolytic activity from aerobic to anaerobic glycolysis. Hyperglycolytic cancer cells exhibit increased glucose uptake and transport; changes in ion pumping; decreased ATP production; decreased oxygen utilization; and increased lactate production due to the conversion of pyruvate to lactate in anaerobic glycolysis. Thus, a measurement technique capable of monitoring and comparing glucose utilization and transport, ion pumping rate changes and concentration gradients, oxygen utilization, and lactate production, either as individual data points or combined, can be used to detect hyperactive pre- and post-cancerous activity. The metabolic state, kinetics, and aggressiveness of these cells can be characterized and classified. Furthermore, the velocity of glycolysis, the maximum velocity, and the Michaelis-Menten constant can be calculated and compared with normal cell data.

In one embodiment of the invention, SMMR technology described herein provides an opportunity for detailed exploration and spectroscopic monitoring of cellular metabolic pathways with novel low-cost instrumentation, which may lead to substantial improvements in the identification and the characterization of cancer cells. The ability to improve diagnosis, staging, therapeutic selection/effectiveness assessment and monitoring for metastatic cell recurrence would represent a significant advancement in cancer diagnosis, and potentially for improved differentiation and classification of solid tumors for selection and optimization of treatment regimes.

Tumor Markers

Potentially the most powerful screening technique for cancer would involve a class of compounds that have been designated as tumor markers. The presence, or less optimally the absence of these species in blood or other readily accessible tissue would indicate a high probability of a cancer in a subject. The marker would be detectable preferably by the use of spectroscopy of the skin or peripheral tissues, and the monitoring of such a compound would correlate with the development of the cancer and also indicate the type of disease. Cancer staging, assessing the extent of local and distant disease, can also be accomplished using the SMMR of the invention. To date, no one marker has been identified that can definitively signal the presence of a tumor. There are however a number of biochemicals and genetic markers that together can improve the diagnosis of a cancerous condition.

The markers may be generated either by the cancer cells themselves or by the body in response to the tumor. The marker may be a normal biochemical or may be a material that is only generated when a tumor is present. A number of possible markers have been identified including, but not limited to, antigens, some antibodies, hormones and enzymes.

Antigens that indicate carcinogenesis include oncofetal antigens, which are antigens that are normally only present in an embryo or fetus. However, the presence or increased concentrations in the adult are a good indication of tumor formation. Hormone production at poorly controlled concentrations may arise from a tumor of a particular endocrine gland. Some pancreatic tumors for example cause the synthesis of high concentrations of insulin. Hormones may also be produced by the tumor cell expressing a synthetic pathway that the normal cell type would not produce. Examples of enzymes that may serve as markers for cancer growth include the over production of acid phosphatase associated with the development of prostrate cancer, as well as increased levels of galactosyl transferase II associated with colon cancer.

The in vivo, non-invasive techniques described herein, enable the selection and measurement of specific intracellular metabolic pathway signals for cells, tissues, organs, and organ systems. This technique would be valuable for distinguishing normalcy, malignancy, or pre-malignancy from non-invasive, in vivo measurements. For example, the SMMR materials delineated in this invention can simply be "painted" or sprayed onto the targeted area to discriminate malignant cells (i.e., hyper-metabolic), or pre-malignant cells (i.e., semi-hyper-metabolic), from normal cells. This discriminative-measurement can be accomplished using a low cost fluorescence detection system or devices, as described herein.

The changes that occur in cells with the onset of carcinogenesis in terms of the active biochemical pathways, the rate of metabolism and the synthesis of marker compounds all provide target mechanisms that may be exploited by the use of fluorescent monitoring compounds such as SMMR. The use of these compounds, some of which have been suggested to be used for the monitoring of blood glucose levels in diabetics, provides a level of sensitivity and selectivity that has not been possible using current technology, i.e. porphyrin dyes and UV or green light.

There are two exemplary methods by which the present technology may be used, including carrying out metabolic monitoring of the whole body by the use of fluorophores applied to the skin, and targeting these changes using fluorescent dyes that respond in a well-characterized mechanism to the altered metabolism. The fluorophores that will be used to monitor these processes include, but are not limited to, compounds described for each targeted pathway.

Metabolic Rate

Current technologies exploit the enhanced metabolic rate of tumor tissue to delineate it from normal tissue. SMMR technology presents a more selective means to monitor tissue having increased metabolic rate. By using dyes that report the activity of a specific pathway, SMMR technology registers an increased level of fluorescence for the increased uptake of the dye and the enhancement due to the activity of the metabolic pathway targeted. For example, pH sensing dyes such as 3-oxo-3H benzoxanthene derivatives undergo a wavelength shift in their emission as a function of pH. Such dyes, when used to delineate tumor tissue, show an increased level of fluorescence and a change in the ratio of their emission bands, which indicate an increased metabolic rate and a lower pH on the tumor tissue.

Glycolysis

Metabolic markers that may be targeted to monitor glycolysis include lactate and oxygen consumption. In tissue that undergoes primarily anaerobic metabolism, the products of this reaction pathway are lactate and adenosine triphosphate (ATP). ATP is synthesized from ADP, the diphosphate analog and phosphate. Lactate is generated as a waste product of the pathway. The ability to determine the relative importance of glycolysis is achieved by monitoring lactate, pH, or NAD(P)H production, as a function of oxygen concentration. It is possible to perturb the oxygen concentration by clamping or cooling the tissue. The relative change in lactate to NAD(P)H ratio then indicates the fraction of metabolism that is carried out via mitochondrial activity. The use of NMR techniques using phosphorous and proton probes would allow the measurement of phosphate, pH and lactate simultaneously.

Lactate Production

Lower pH values of tumors are associated with the synthesis and export of lactic acid by the cell and a higher rate of glycolysis. The generation of a large amount of lactate occurs, even under aerobic conditions. Such behavior is unusual, since in a typical cell the fate of pyruvate, the product of glycolysis, in the presence of oxygen is to be oxidized within the mitochondria. The reasons why the pyruvate generated in a tumor that is not anoxic is not further metabolized by the mitochondria is not clearly understood. It is known that the hexokinase responsible for the initial steps in glycolysis is found bound to the surface of the mitochondrial membrane.

Oxygen Consumption

The use of probes such as Ruthenium tris bipyridyl and related derivates provides a well-proven technique for monitoring oxygen concentration. Other dyes that have also been used to monitor oxygen concentration include porphyrin and phthalocyanine derivatives. The emission of these molecules is sensitive to oxygen concentration. It is possible to monitor the intensity or the lifetime of the emission of these dyes to determine the oxygen concentration. Technically, the simplest apparatus that may be used to monitor the emission lifetime of these dyes contains a modulated light source and a phase-sensitive detector. The phase angle shift of the dye and the degree to which the dye emission is modulated allow the lifetime of the dye to be determined. The parameters measured by the device are related to the lifetime by the expressions shown in equation M7 and M8

$$\tan\phi = \omega\tau \text{ and } m = \sqrt{\frac{1}{(1+\omega^2\tau^2)}} \quad \text{(M7; M8)}$$

where $\phi$ is the phase shift, m is the degree of modulation, $\omega$ is the circular modulation frequency and $\tau$ is the lifetime.

However, there are metabolic differences in the cancer cell that can be targeted using metabolic monitoring technology. The methods and compositions of the invention can be used to monitor those parts of metabolism that are altered when a cell becomes cancerous. For example, such a system can be used to monitor high-risk individuals or populations for particular cancers, and to determine the progress of disease in a subject undergoing treatment.

Antigens and Hormones

Antigens may be present in circulating blood at extremely low concentrations. To detect them and to monitor their concentrations requires a high degree of selectivity and sensitivity. These molecules can be targeted by the use of antibody bound SMMR fluorophores. Antibodies are large protein molecules that have a high degree of specificity for a particular antigen. They are synthesized by the immune system specifically to target an antigen of interest. The antibody provides the selectivity required to eliminate false positive detection. The binding of the antigen causes a conformational change in the antibody that results in a large fluorescent change in the dye molecule. Those skilled in the art will recognize that hormones may be monitored in a similar fashion using fluorescent modified hormone receptor molecules in the same way as one would use the antibody.

Enzymes

Common techniques for the monitoring of enzyme activity include monitoring the substrate, the cofactor or a product of the enzyme reaction. To monitor enzyme activity through the skin, SMMR technology uses fluorescent substrate analogs tethered in the epidermis. The change in fluorescence of the substrate when bound to the enzyme would be indicative of the enzyme concentration.

Thus, the metabolic differences in the cancer cell can be targeted using metabolic monitoring technology. Those parts of metabolism that are altered when a cell becomes cancerous can be monitored using the methods and compositions of the invention. Such a system can be used to monitor high-risk individuals or populations for a particular cancer and to determine the progress of the disease in a subject undergoing treatment.

Suitable Small Molecule Metabolic Reporters of the Invention

Suitable small molecule metabolic reporters of the invention include, but are not limited to: fluorophores, protein labeled fluorophores, proteins comprising a photooxidizable cofactor, and proteins comprising another intercalated fluorophore as described herein.

It is well known that specific dyes bind to cellular structures and allow imaging and anatomical/histological studies of intracellular structures. See, e.g., the information available from companies such as Molecular Probes or Sigma-Aldrich. It is also well known that some signals from these dyes can be used to characterize cellular metabolism in vitro. Fluorescent chemical sensors have been reported to play a critical role in the elucidation of cellular mechanisms by giving real-time information about the environment of a cell in a non-destructive manner, See, e.g., Glass, J. Am. Chem. Soc. 2000, 122: 4522-4523. For these applications, sensor affinity and selectivity are of utmost concern. Thus, a useful sensor must recognize its analyte with high specificity and possess an affinity that is commensurate with the average concentration of the analyte in solution. Id. However, no specific fluorophores have been named, and no fluorophore design requirements have been published for in vivo, non-invasive elucidation of metabolic pathways for any medical applications in general, and, specifically, for those described by this invention (e.g., in a preferred embodiment for measurement of blood glucose). A surprising discovery has been made that the detailed and specific absorption and emission spectral characteristics of a select set of dyes, when introduced into living cells of organisms (in vivo), change as a qualitative and quantitative indication of extracellular and intracellular metabolism. One or more dyes of the select set presented herein are specifically used to report metabolite concentration, which are then used to further define the quantity or quality of metabolic activities within living organisms, such as glycolysis.

This invention relates to SMMRs that indicate the rate and quantity of glycolysis occurring within the living cell loci. The detailed spectral changes noted as direct and indirect metabolic reporters include: variation in fluorescence emission intensity and lifetime, variation in wavelength position for absorption and emission maxima, and variation in bandwidth and spectral shapes of absorption and emission spectra. These measurable changes vary in direct proportion to the changes in concentrations of metabolite molecules within the physical proximity of associated extracellular and intracellular structures. The information provided by measuring the changes in specific reporter dye spectra following introduction into living organisms has utility as part of a low-cost method and apparatus for the detailed, real-time measurement and delineation of metabolic pathways and processes in living organisms.

In vivo small molecule metabolic reporter measurements require the in situ interaction of living cells with the reporter molecules to give an accurate and real-time indication of the metabolic state for a whole organism, an organ, a tissue type, or individual cells. The measurements of the metabolic state for living organisms can thus be made non-destructively and non-invasively using spectroscopic measurements on living tissues and cells. Furthermore, custom molecules can be synthesized based on detailed understanding of reporter interactions with in vivo metabolic processes. See, e.g., FIGS. 17A through 17D. This discovery has allowed optimization of these dye molecules in their active role as SMMR, for reduced toxicity, selective residence time in targeted tissues, cellular binding site specificity, analyte selectivity and sensitivity, photostability, and fluorescence spectral characteristics. These fluorescence spectral characteristics can be selected based on molecular structures for SMMR, and include: emission intensity and lifetime, location of excitation/absorption and emission maxima, Stokes shift, bandwidth, spectral shape changes due to the presence of metabolites, quantum yield, and quantum efficiency.

Therefore, the methods and devices disclosed herein represent an improvement over current techniques such as antibody:antigen labeling, because they relates explicitly to a unique use of small molecules capable of penetrating the stratum corneum, that when placed in living tissue allow a measurable fluorescence response proportional to metabolic changes in living cells, tissues, and whole organisms (e.g., animals and humans), without initiating an immune response. These measured metabolite signals provide delineation of metabolic pathways by measuring the spectra of certain dye molecules when the molecules are used in precise ways, under exacting conditions, and when placed in specific structures within living cells and tissues.

A dye that is classified as a reporter according to the invention must meet several minimum criteria: low toxicity; ability to be delivered precisely to target tissue; report quantitative information with respect to the concentration of specific metabolites when measured in vivo; and detectable using wavelength emission-related technology. Preferably the dyes are fluorescent. Mechanisms for identifying and/or constructing exemplary reporters of the invention are described below. Mathematical models are provided based on the metabolite or metabolic pathway to be analyzed.

Figure 15:
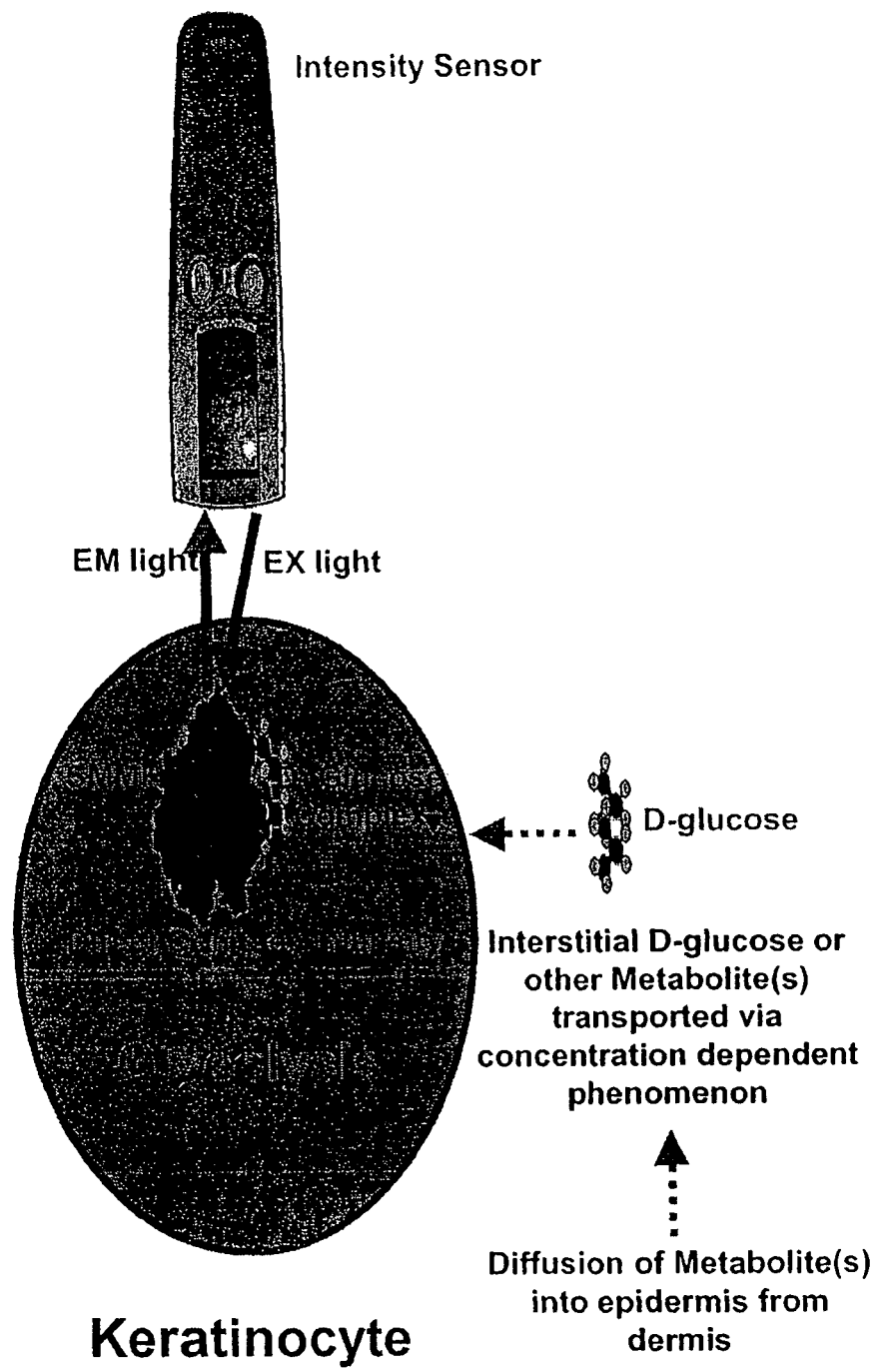
FIG. 15 is a schematic of SMMR Mechanism 4 for a direct complex intensity reporter. SMMR direct complex intensity reporter mechanism for a fluorescence signal is based upon the specific binding of a metabolite molecule (e.g., D-glucose) into a larger protein (e.g., enzyme-based) SMMR. The fluorescent protein SMMR is excited wherever the influence of the specifically bound metabolite alters the fluorescence properties of the SMMR. This altered fluorescence emission from the SMMR is detected with a sensor. Where there is a non-rate-limiting excess of SMMR, the emission intensity is proportional to the concentration of metabolite present. This mechanism is effective for intracellular, extracellular, and in vitro glucose quantitative measurements. This mechanism could also be useful for various in vitro diagnostic uses.
Figure 16:
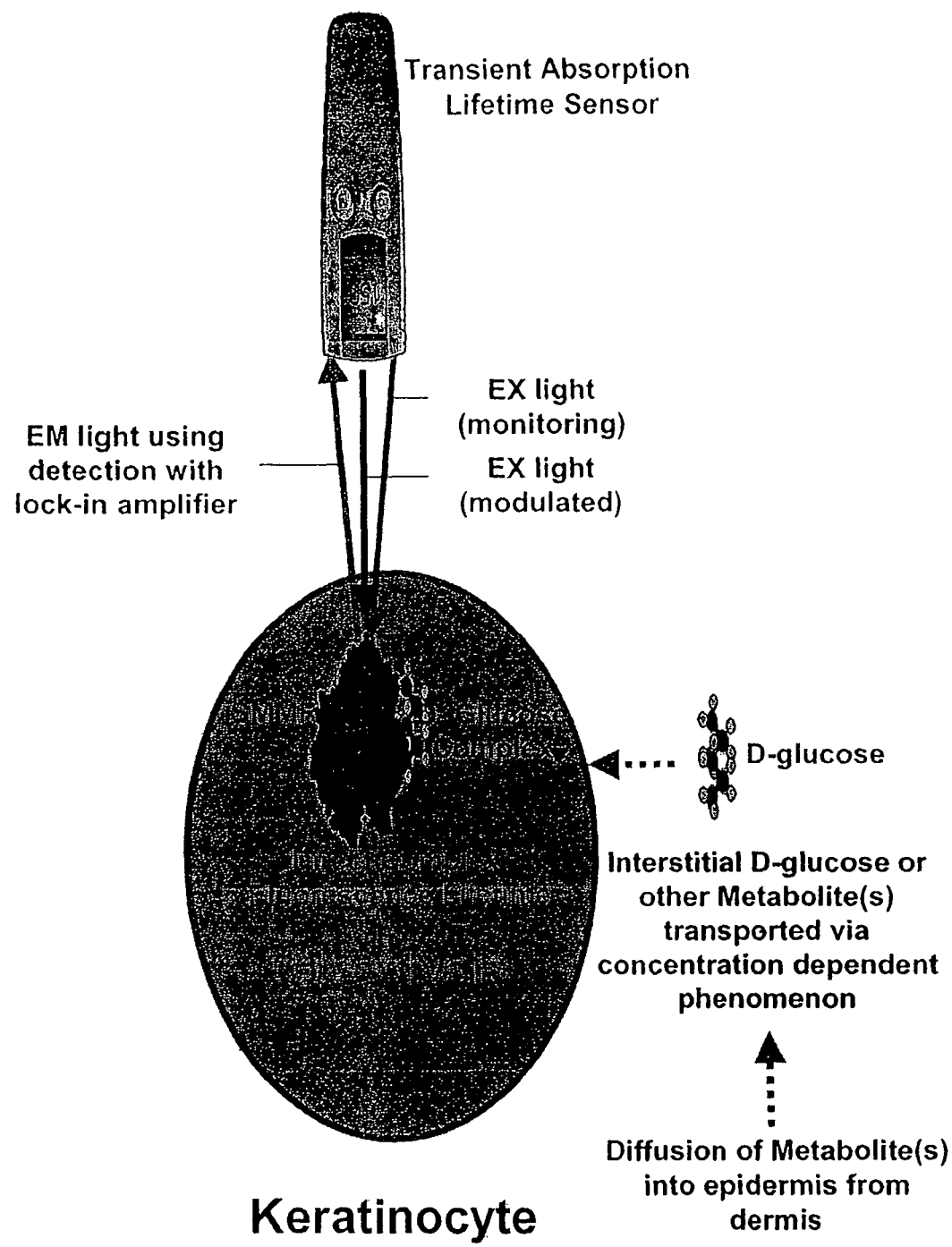
FIG. 16 is a schematic of SMMR Mechanism 5 for a direct complex lifetime reporter. SMMR direct complex lifetime reporter mechanism for an absorption signal is based upon the specific binding of a metabolite molecule (e.g., D-glucose) into a larger protein (e.g., enzyme-based) SMMR. The protein-based SMMR is excited by irradiation using modulated light, whereas irradiation with a second wavelength of light is used to monitor the transient absorption lifetime using a detection system that can include a lock-in amplifier. The influence of the specifically bound metabolite such as glucose alters the excited state lifetime properties of the SMMR. This altered lifetime from the SMMR is detected with a sensor. Under conditions where the influence of the metabolite is significant, and where there is a non-rate-limiting excess of SMMR, the fluorescence lifetime signal is proportional to the concentration of metabolite present. As in the case of Mechanism 4, this mechanism is effective for intracellular, extracellular, and in vitro glucose quantitative measurements. It would be clear to one skilled in the art that this mechanism could also be useful for in vitro diagnostic uses.

In order to qualify as a SMMR according to this invention, dyes require one or more of the following criteria:
1. Enhancement of signal-to-noise ratio of native autofluorescence measurements through the process of:
    a. ENERGY TRANSFER from NADH, NAD(P)H, or FAD$^+$ to SMMR (which boosts signal by 5 to 50 fold) that is an indirect indication of redox transfer coenzyme activity within cells and tissues due to glycolysis (see FIG. 12; Mechanism 1);
2. Enhancement of Specific Metabolite and Precursor Signals such as:
    a. Lactate SMMRs that indicate lactate/hydrogen ion formation from anaerobic glycolysis activity (measurement sites include intracellular, extracellular, and organelle loci) (see FIG. 13; Mechanism 2);
    b. Mitochondrial Membrane Potential SMMRs that indicate overall changes in mitochondrial membrane redox-potential that corresponds to changes in glucose (see FIG. 14; Mechanism 3);
    c. Calcium ion ($Ca^{2+}$) tracking SMMRs that indicate available adenosine triphosphate (ATP) and ion pump transport activity fueled by glycolytic activity (see FIG. 13; Mechanism 2);
    d. Glycogen SMMRs using glycogen-staining molecules that indicate the occurrence of glycolysis and resultant storage of glycogen molecules (see FIG. 13; Mechanism 2).
3. Direct measurement of glucose molecules in vivo using:
    a. Protein-labeled fluorophores such as proteins that are specifically bound to glucose and have enhanced fluorescence quantum efficiency. When placed into the skin, the resulting fluorescence is indicative of the amount of glucose present (see FIG. 15; Mechanism 4);
    b. Proteins comprising a photoredox active cofactor (such as flavin adenine dinucleotide, i.e., FAD) that are used to observe excited state lifetime fluorescence by monitoring the triplet state of FAD ($^3$FAD*) (see FIG. 16; Mechanism 5).

These mechanisms are referred to as Mechanisms 1-5 and are depicted schematically in FIGS. 11-16.

Some suitable reporters according to the invention are available commercially, and include, but are not limited to, the following: (1) Rh123 for measuring NAD(P)H (nicotinamide adenine dinucleotide (phosphate), reduced form) using energy transfer, or FAD$^+$ (flavin adenine dinucleotide, oxidized form) using energy transfer; (2) membrane localizing dyes such as diphenylhexatriene, xanthenes, cyanines as well as diphenyl hexatriene and its derivatives, for measurement of energy and glucose transport by membrane receptors such as GluT1; (3) pH (i.e., lactate/H$^+$) indicating dyes such as phenolphthalein, xanthene dyes such as 2',7'-bis-(2-carboxyethyl)-5-(and -6)-carboxyfluorescein, (BCECF), benzenedicarboxylic acid, 2(or 4)-[10-(dimethylamino)-3-oxo-3H-benzo[c]xanthene-7-yl]-(SNARF-1) for calculations of lactate/H+ ratios, cytosolic NAD/NADH ratios or pyruvate/lactate ratios; (4) dyes known to have altered emission properties depending on the redox potential, ATP/ADP ratio, $Ca^{2+}$-pumping rate, $Mg^{2+}$-pumping rate, $Na^+$-pumping rate, or $K^+$-pumping rate of its surroundings, as these processes are ATP regulated and ATP formation in keratinocytes is a direct result of glycolysis fueled by glucose; (5) vital mitochondrial membrane stains or mitochondrial membrane dyes, especially those that produce a fluorescence response to changes in mitochondrial membrane potential; (6) reactive molecules that directly or inversely correlate to glucose concentration, such as nitric oxide (NO); and (7) molecules that directly bind to D-glucose producing a fluorescence response. Additional exemplary SMMRs are provided throughout the disclosure. Other appropriate SMMRs of the invention will be apparent to those skilled in the art.

1. Energy Transfer Measurements

The use of energy transfer as a mechanism to measure the presence and quantity of coenzymes in the cellular environment has been demonstrated in vitro after removing cells from organisms. Singlet bimolecular electronic energy transfer reactions, which can be designated as B*+A→B+A*, where the energy is transferred from molecule B to A, proceed by at least four different mechanisms: (1) long-range resonance energy transfer ("fluorescence resonance energy transfer (FRET)" or Förster transfer), which occurs between dipole-dipole interactions over a molecule distance of up to 5 nm; (2) short-range collisional energy transfer (CET), requiring electron-exchange interactions between the donor and acceptor molecular orbitals (that is the main mechanism of transfer in the majority of SMMRs); (3) static quenching, in which the donor and acceptor molecules are in close proximity in the ground state and; (4) radiative energy transfer (RET), involving donor emission and reabsorption of the photon by the acceptor.

A number of SMMRs (e.g., Rh123) provide excellent energy transfer capacity wherein the metabolite of interest is excited. SMMRs report an enhanced signal at its characteristic emission wavelength. This energy transfer mechanism provides signal enhancement for normally very weak autofluorescence. What is normally a very weak signal with about 10 percent relative discrimination (i.e., a signal to noise of 10:1 to 50:1), can be discriminated at 0.2 to 1 percent signal (i.e., signal-to-noise of 100:1 and higher to about 500:1). This signal enhancement allows the use of low-cost diode-based instruments or sensors for making accurate measurements of fluorescence signal.

The specific application of energy transfer is for the measurement of metabolic coenzymes essential in reduction-oxidation (redox) molecular biosyntheses, wherein the molecule has a stoichiometric or highly correlated relationship with glucose concentration. Coenzymes directly involved in redox mediated reactions include NADH, NAD(P)H, and FADH$_2$. A measurement of the change in fluorescence signal brought about by using a reporter of the invention in vivo to track the formation of NAD(P)H (nicotinamide adenine dinucleotide (phosphate), reduced form) for energy transfer, FAD$^+$ (flavin adenine dinucleotide, oxidized form) for energy transfer, can be used as an indirect measurement of the quantity of glucose entering a cell. Enhancement of these signals allows accurate tracking of glucose metabolism and other biosynthetic processes within the living cell. Low-cost tracking of the activity for these specific coenzymes enables oxidative phosphorylation and anaerobic glycolysis to be monitored in real-time.

2. Enhancement of Specific Metabolite and Precursor Signals

The sensor composition used in these methods for monitoring and detecting the concentration of one or more metabolite(s) or analyte(s) can include, for example, a reporter that is a mitochondrial stain that is sensitive to membrane potential or chemical gradient. Examples of suitable mitochondrial stains include a polycyclic aromatic hydrocarbon dye, such as, for example, rhodamine 123; di-4-ANEPPS; di-8-ANEPPS; DiBAC$_4$(3); RH421; tetramethylrhodamine ethyl ester, perchlorate; tetramethylrhodamine methyl ester, perchlorate; 3,3'-dihexyloxacarbocyanine; 5,5',6,6'-tetrachloro-1,1',3,3'-tetraethyl-benzimidazolylcarbocyanine chloride; 2-(4-(dimethylamino)styryl)-N-ethylpyridinium iodide; 5,5',6,6'-tetrachloro-1,1',3,3'-tetraethyl-benzimidazolylcarbocyanine iodide; nonylacridine orange; dihydrorhodamine 123; dihydrorhodamine 123, dihydrochloride salt; xanthene; 2',7'-bis-(2-carboxyethyl)-5-(and -6)-carboxyfluorescein; benzenedicarboxylic acid, 2(or 4)-[10-(dimethylamino)-3-oxo-3-H-benzo[c]xanthene-7-yl]; or iodine dissolved in potassium iodide. The reporter dye can also be coumarin; derivatives of coumarin; anthraquinones; cyanine dyes; azo dyes; xanthene dyes; arylmethine dyes; pyrene derivatives; or ruthenium bipyridyl complexes.

Reporters useful for illustrating this mechanism include pH:lacate/H$^+$ indicating molecules where two or more wavelengths change directly in proportion to a change in pH:lacate/H$^+$ concentration. A two-photon fluorescence lifetime imaging within the dead uppermost layers of the epidermis (i.e., the stratum corneum) has been described, where the fluorophores are introduced into the tissue to measure the pH gradient across human skin. See, e.g., Hanson et al. Hanson et al., 2002, Biophysical Journal 83: 1682-1690, incorporated herein by reference. However, the skin tissue was removed from the animal prior to analysis, such that their in vitro technique was performed on dying tissue.

Proteins acting as reporters, as described herein, can be used in vivo for direct measurement of intracellular or extracellular glucose. Fluorescence emission and lifetime intensity response is proportional to the glucose concentration within the cell or external to the cell in interstitial tissue fluid or blood.

The essential characteristic in identifying a member of the class of SMMR dyes includes those compounds that report fluorescence changes in proportion to changes in glucose concentration for in vivo measurements. These dyes may be discovered empirically by screening large numbers of compounds for signal efficacy, or they may be designed using a basic understanding of photochemistry. The spectroscopic properties of SMMRs useful for routine analysis, especially when using low-cost instruments include, but are not limited to, one or more of the following: molecules that exhibit a large molar absorption coefficient (10,000 L mol$^{-1}$ cm$^{-1}$ and above), molecules that exhibit a high Stokes shift (e.g., 20 to 150 nm), long (e.g., 2 hours to 4 weeks) residence time at target site, molecules that are highly photostable (e.g., less than 5 percent signal loss at use excitation power), molecules that exhibit little or no excited state chemistry (i.e., inert or non-reactive in excited state), and molecules that exhibit large fluorescence quantum yield (e.g., Quantum Yield [$\phi_F$] greater than 0.4).

Examples of suitable SMMRs include, but are not limited to, modifications of fluorescence dyes to include molecular size attachments as: acetoxy methyl esters, chloro-methyl derivatives, alkyl chain adducts, highly charged moieties, enzyme substrate mimic, enzyme cofactor tethers, and membrane binding tethers.

Figure 17A:
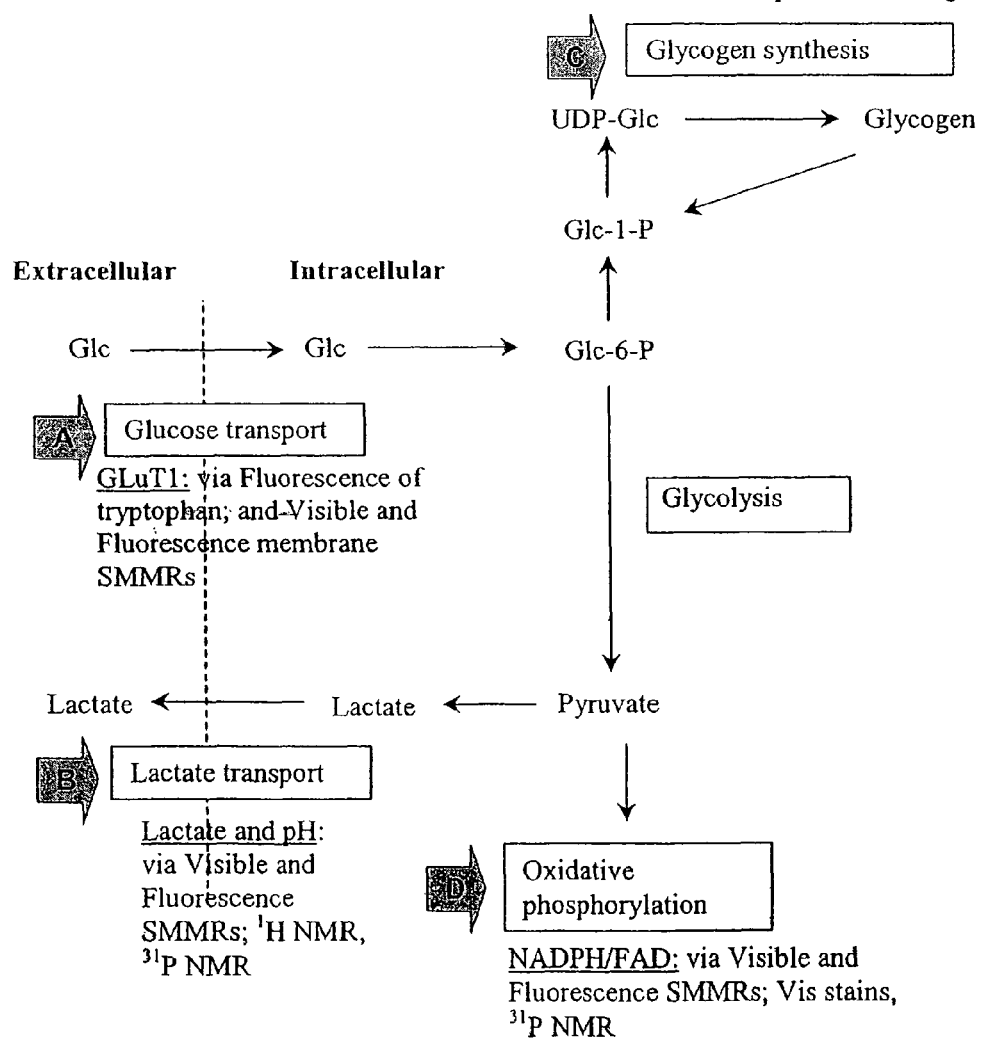
FIGS. 17A, 17B, 17C and 17D are schematics depicting mechanisms operating in skin metabolism, which are referred to herein as Scheme 1, Scheme 2, Scheme 3 and Scheme 4, respectively.
Figure 17B:
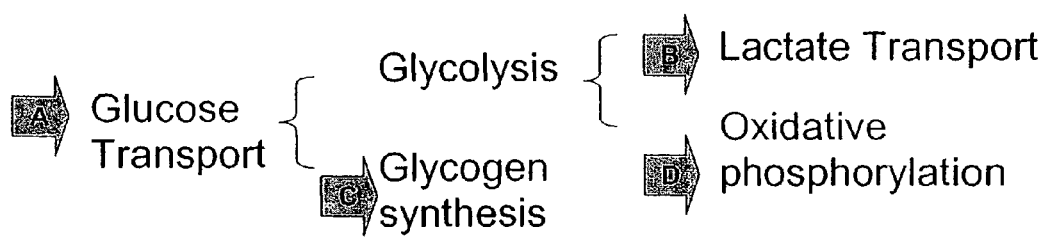
Figure 17C:
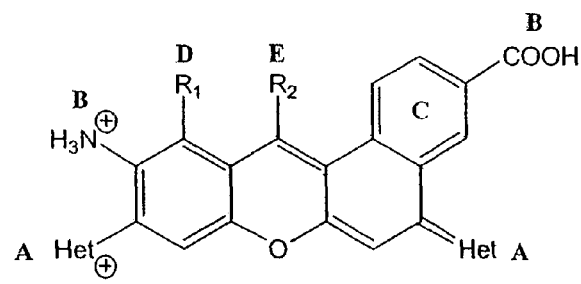
Figure 17D:
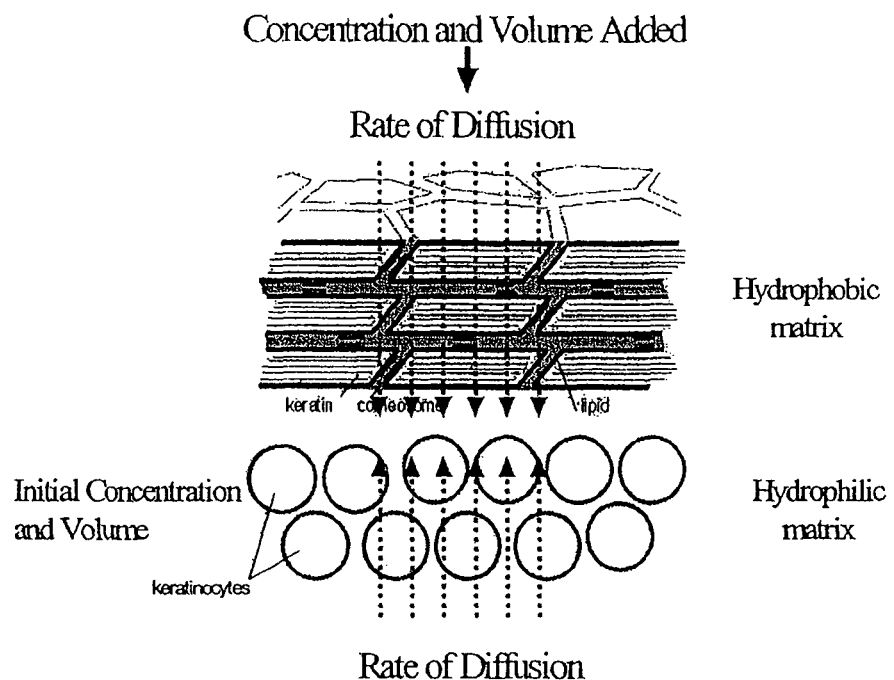
Figure 18:
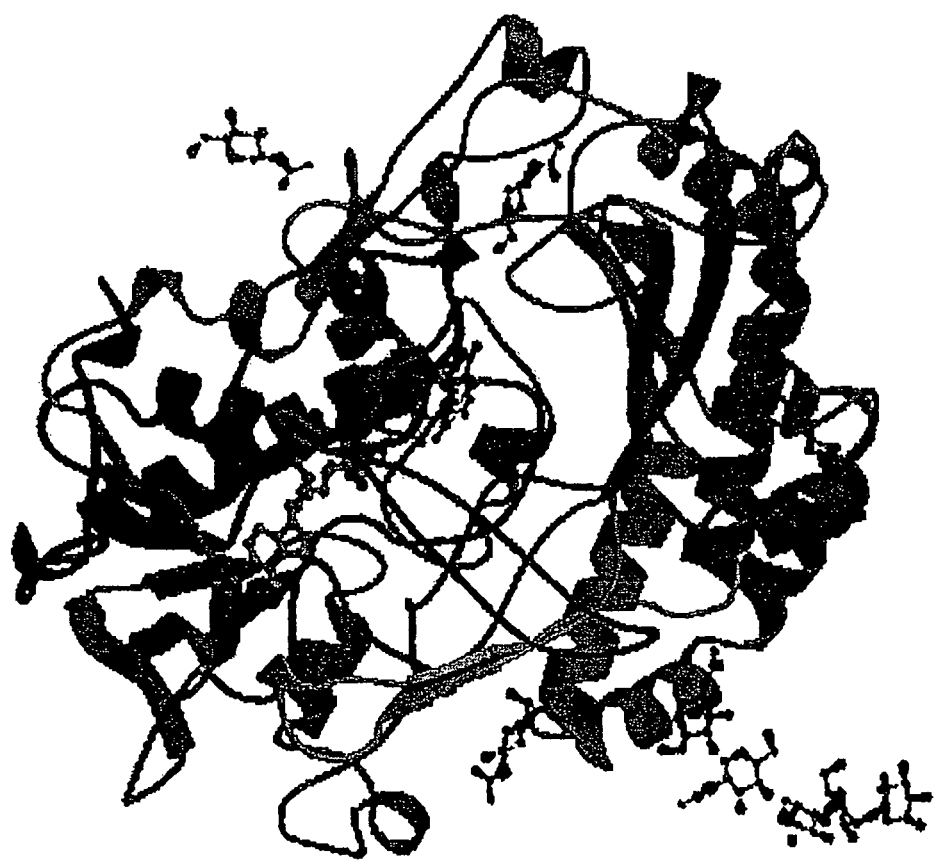
FIG. 18 illustrates the X-Ray Crystal structure of glucose oxidase from *Aspergillus niger* refined at 2.3 Angstrom resolution.
Figure 19:
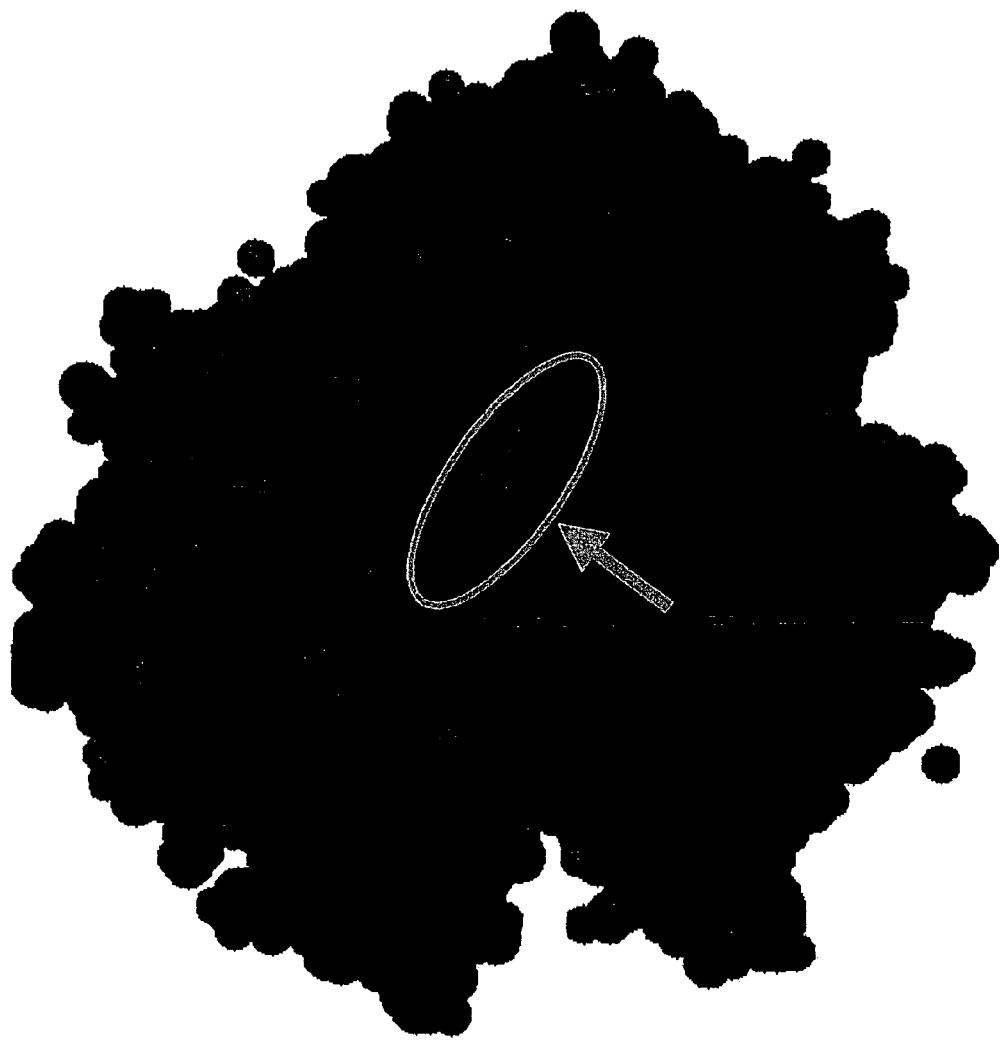
FIG. 19 illustrates the molecular structure of glucose oxidase and depicts glucose insertion.
Figure 20:
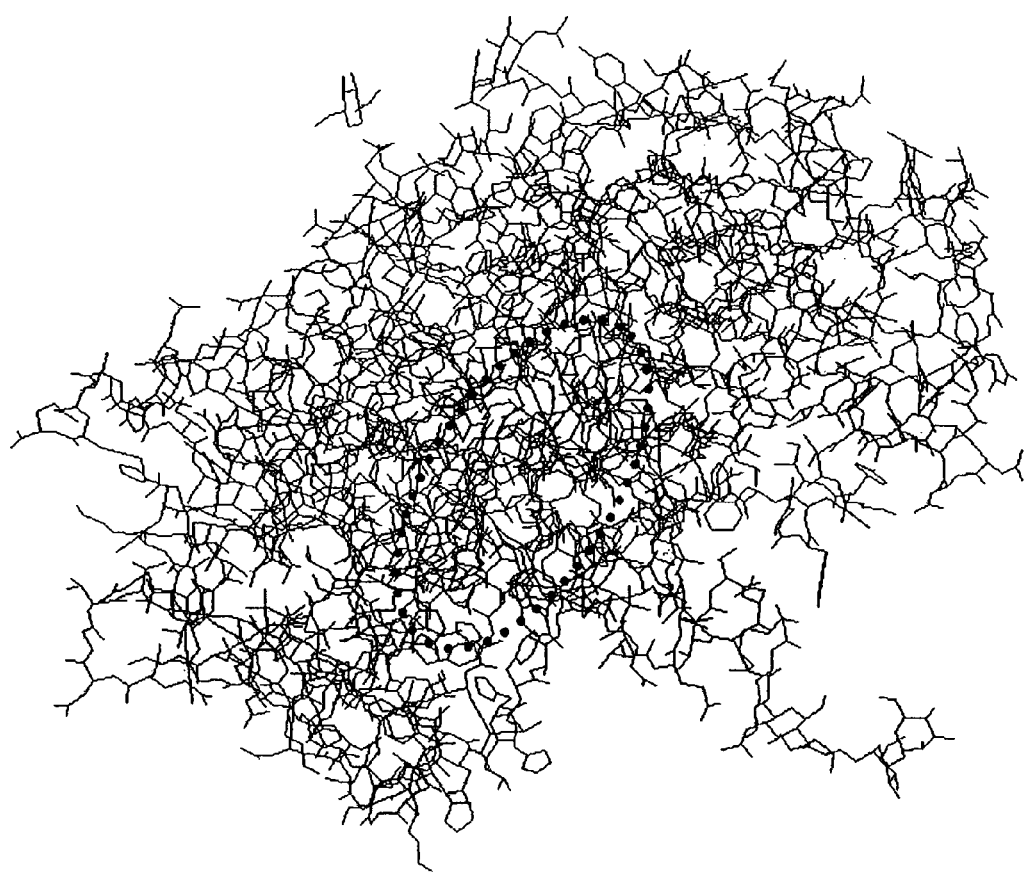
FIG. 20 illustrates the molecular structure of glucose oxidase and depicts replacement of FAD with reagent FL Sub-Mol (fluorophore labeled substituent molecule) inclusion.
Figure 21:
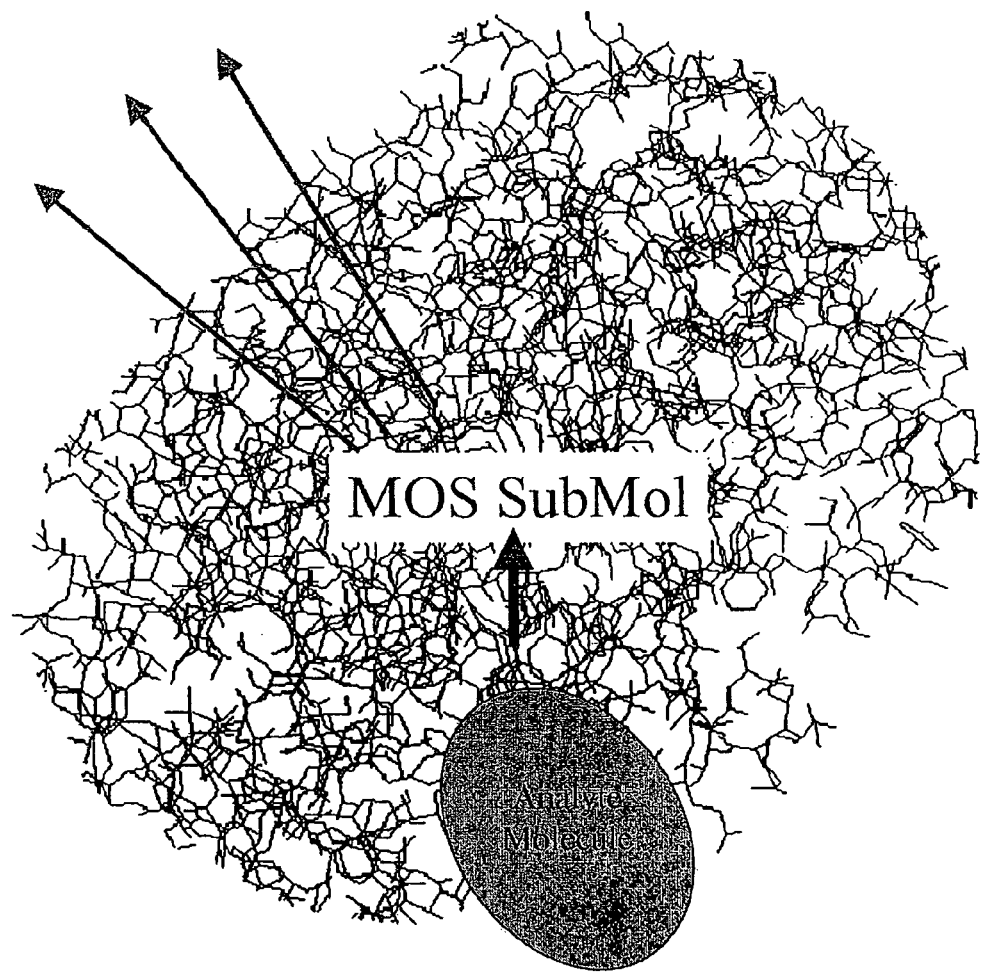
FIG. 21 illustrates a generic protein (e.g., an enzyme) with analyte molecule and SubMol intercalated into the FAD position (specific case). Note that the SubMol could also be attached to the periphery of the protein molecule to produce an optical response in the presence of an analyte molecule (e.g., glucose)
Figure 22:
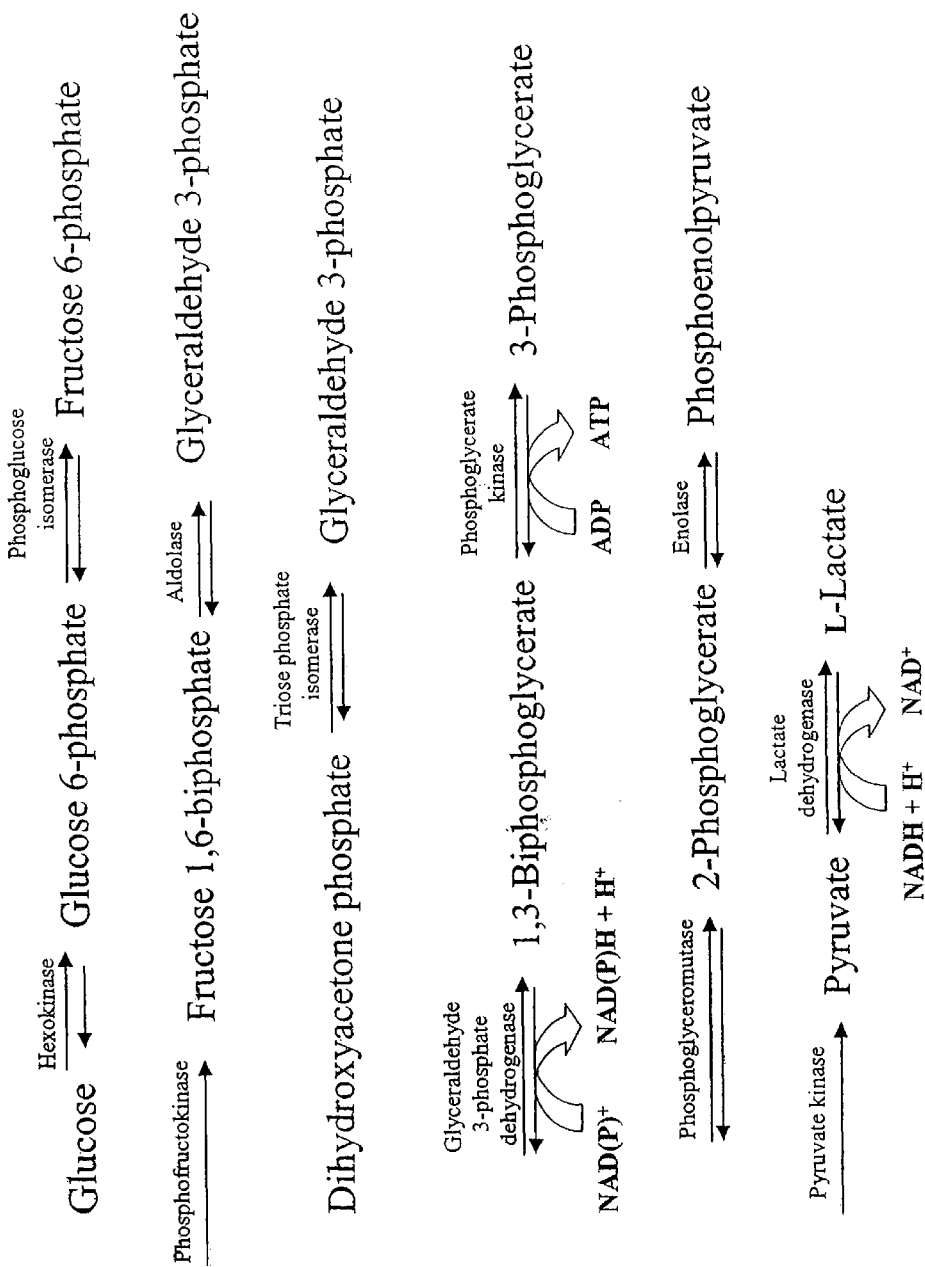
FIG. 22 is a schematic showing the steps of glucose metabolism.

The basic starting dyes used to develop these reporters are polycyclic aromatic hydrocarbon dyes, including, but not limited to: rhodamine 123; di-4-ANEPPS, di-8-ANEPPS; DiBAC$_4$(3); RH421; tetramethylrhodamine ethyl ester, perchlorate; tetramethylrhodamine methyl ester, perchlorate; 3,3'-dihexyloxacarbocyanine; 2-(4-(dimethylamino)styryl)-N-ethylpyridinium iodide; 5,5',6,6'-tetrachloro-1,1',3,3'-tetraethyl-benzimidazolylcarbocyanine chloride; 5,5',6,6'-tetrachloro-1,1',3,3'-tetraethyl-benzimidazolylcarbocyanine iodide; nonylacridine orange; xanthene dyes especially 2',7'-bis-(2-carboxyethyl)-5-(and -6)-carboxyfluorescein; dihydrorhodamine 123; dihydrorhodamine 123, dihydrochloride salt; and benzenedicarboxylic acid, 2(or 4)-[10-(dimethylamino)-3-oxo-3-H-benzo[c]xanthene-7-yl]; and iodine dissolved in potassium iodide. Other dyes or stains that are useful as SMMRs include, but are not limited to: fluorescein derivatives, modified coumarin; derivatives of coumarin, anthraquinones; cyanine dyes, azo dyes; xanthene dyes; arylmethine dyes; pyrene derivatives; and ruthenium bipyridyl complexes. An exemplary backbone of a contemplated SMMR is shown in FIG. 17C and described further in the Examples, infra.

However, the use of other dyes exhibiting similar characteristics and chemical structure for the in vivo determination of glucose is an extension of this concept, and an important aspect of this invention. Dyes that exhibit the provided characteristics and chemical structures would be known to one skilled in the art. Alternative embodiments would differ only in the dye selected and in the optimization of the techniques shown herein. This invention includes methodologies to develop optimum conditions for the use of other dyes expressly for the purpose of extending or refining this application.

Mitochondrial stains have been used in vitro for measuring glucose concentration in immortal cell lines by fluorescence. See, e.g., N. Borth, G. Kral, H. Katinger, Cytometry 14:70-73 (1993). However, no known previous work determines the glucose concentration in blood for a living organism by non-invasive, in vivo measurement of the glucose level in skin by means of fluorescence measurements of metabolic indicators/reporters (such as SMMR) of glucose metabolism.

One specific redox potential indicating dye, Rhodamine 123 (Rh123), provides an illustrated working example of the present invention. Rh123 dye has the systematic name (2-(6-Amino-3-imino-3H-xanthen-9-yl)benzoic acid methyl ester), given CAS No. 62669-70-9. Membrane reporting redox potential indicating dyes such as Rh123 have been used in concentrations of 10-150 µM for multiple applications, many related to intracellular mitochondrial activity, specifically for measurement of fluorescence response proportional to changes in transmembrane redox potential in order to research the mechanics of cell metabolism.

Rh123 is commonly known as green fluorescent mitochondrial dye and is widely applied in cytometry studies involving mitochondrial membrane potential. Its spectral properties include an excitation maximum wavelength of 485 to 505 nm with an emission wavelength of 525 to 534 nm. It exhibits an absorption maximum from 485 to 505 nm and has a molar absorption coefficient of 97,000 Lmol$^{-1}$ cm$^{-1}$. This dye is an orange-red solid that is soluble in methanol (MeOH), dimethyl sulfoxide (DMSO) and dimethylformamide (DMF). These dyes are light sensitive. Once in solution they should be kept at less than 5° C. and protected from direct illumination for long-term storage and optimum efficacy. Rh123 has a molecular formula of $C_{21}H_{17}ClN_2O_3$ and a molecular weight of 381 daltons. The molecule has low toxicity and has a reported intravenous lethal dose for animals (LD10) of approximately 20 mg/kg of body weight; and a fifty percent lethality (LD50) of 89.5 mg/kg (i.v.) in rats (Merck).

Rh123, and other dyes exhibiting similar molecular structures, have a specific set of chemical properties whereby the molecule is fluorescent, cationic (i.e., positively charged), of low molecular weight, lipophilic, and configurable as a water-soluble salt. Having these molecular properties, dyes such as Rh123 exhibit preferential binding to negatively charged mitochondrial membrane lipids. The final quantity of dye that collects within the mitochondrial membrane is dependent on the molar concentration of the dye within the surrounding medium (i.e., intercellular and cytosol concentrations) and, more importantly, the mitochondrial membrane potential. The dye is distributed into the membrane by means of general diffusion such that the molecules move into the cell and then to the mitochondrial membrane at a rate that is dependent on chemical kinetics and metabolic rate. Thus, increases in temperature and thereby metabolic rate, will increase the rate of random motion that is driving the concentration of Rh123 molecules in solution to equilibrium.

Accurate in vivo and in vitro measurements can be made over nominal temperature ranges from 75 to 105° F., or wider. Variations in the subject temperature wider than approximately ±5° F. of the target tissue require re-calibration, as noted elsewhere. The method used to recalibrate for any temperature range is provided to make certain that the temperature is measured while the calibration is performed using equations 1-5 and 13-16 of the invention. Any subsequent measurement of the test sample may be performed within ±5° F. without concern for temperature variation.

In the case of mitochondrial dyes, each cationic molecule of dye accumulates stoichiometrically as negatively charged moieties within the inner mitochondrial membrane of healthy metabolizing cells at a concentration dependent rate. The final concentration of dye uptake for each cell is dependent upon the number of mitochondria present within the treated cells as well as the changes in the mitochondrial membrane potential within each cell.

Under conditions where glucose is the major metabolic substrate for the cell, oxidative phosphorylation is fueled by the products of glycolysis. See, e.g., Johnson, L. V., et al. *J. Cell Biol.* 83, 526 (1981). Additional discussions describing research applications of membrane potential-indicating dyes are found in, e.g., R. C. Scaduto, and L. W. Grotyohann, *Biophysical Journal* 76, 469 (1999) and related references. For most of the reducing reactions that occur in cells, the reducing power is provided by NAD(P)H. The pH gradient that generates the mitochondrial membrane potential is fueled by NADH. This NADH may be derived from the Krebs citric acid cycle as well as from glycolysis.

Figure 14:
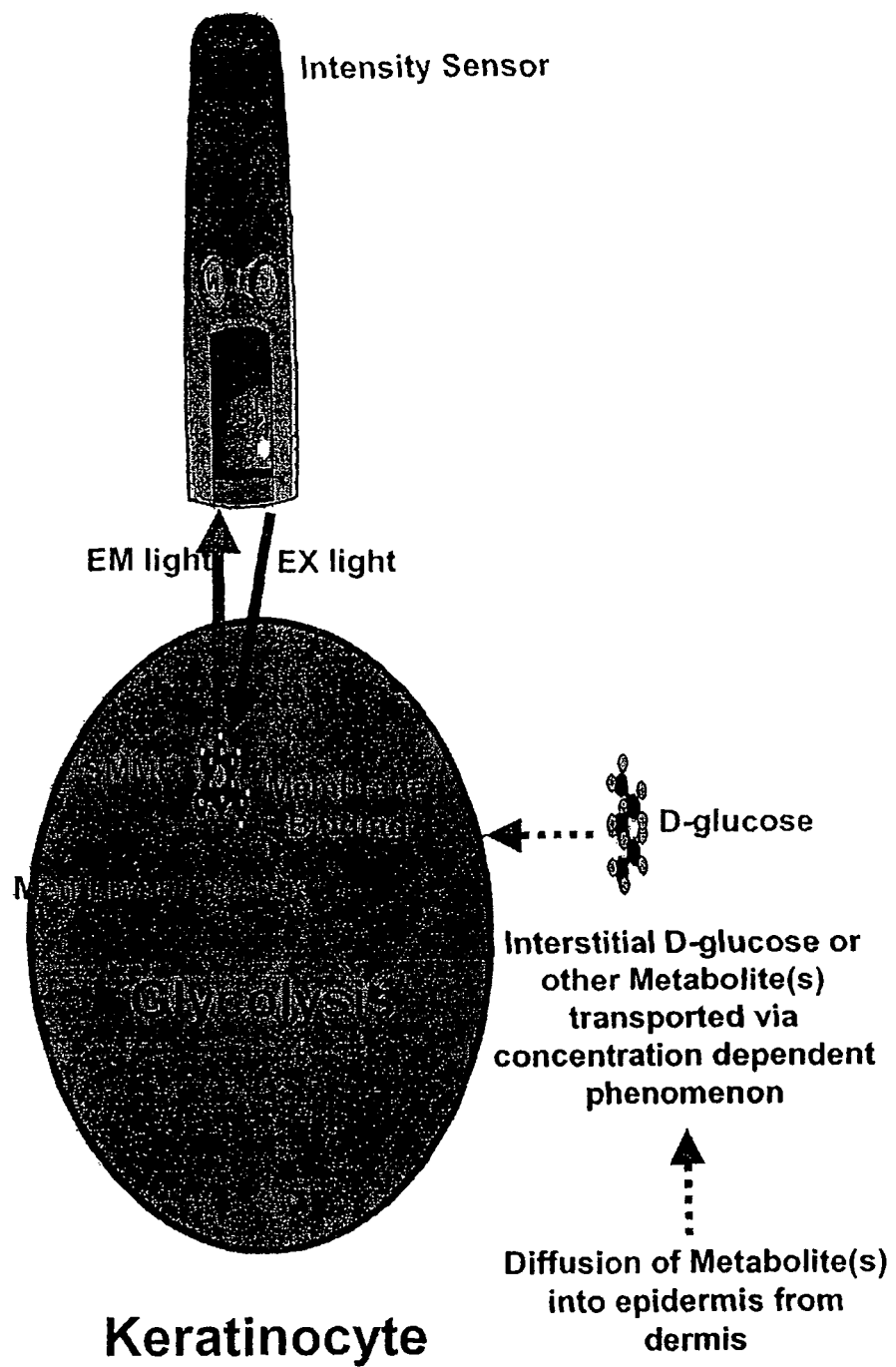
FIG. 14 is a schematic of SMMR Mechanism 3 for an indirect membrane potential reporter. SMMR membrane potential reporter mechanism for a fluorescence signal is based upon the fluorescence properties of an SMMR when bound to a cellular membrane, such as the inner membrane of mitochondria. A fluorescent SMMR is excited wherever the influence of the membrane potential at the membrane-binding site alters the fluorescence properties of the SMMR. This altered fluorescence emission from the SMMR is detected with a sensor. Where there is a non-rate-limiting excess of SMMR, the emission intensity is proportional to the concentration of metabolite present.

Illumination using energy at approximately 490 nm excites Rh123 directly and its fluorescence emission can be detected at approximately 530 nm. The final baseline intensity of the dye is proportional to the concentration of dye present at the mitochondria, and to the mitochondrial density. The changes in the net fluorescence intensity of Rh123-like dyes are directly proportional to the changes in the membrane potential of the cell. Molecules behaving in this manner are referred to as transmembrane redox potential indicating SMMRs (FIG. 14). Metabolic activity fueled by glucose is indicated by Rh123-like dye fluorescence intensity.

Specific chemical agents are known to disrupt oxidative phosphorylation and glucose metabolism. Any such agent causing decreased cellular respiration, cellular energy balance, and cell viability will affect the fluorescence intensity of the dye bound to the mitochondria. A decrease in the glucose concentration available to the cell causes a reduction in ATP production due to depletion in metabolism from lowered oxidative phosphorylation. Such a decrease in glucose concentration is indicated by a corresponding decrease in fluorescent intensity. The demonstration of a linear increase in mitochondrial-bound Rh123 fluorescence with changes in respective glucose concentration for immortal cell lines has been shown. See, e.g. Borth, et al. Cytochemistry 14, 70 (1993), incorporated herein by reference. Borth demonstrated that for isolated 3D6-LC4 human-mouse heterohybridoma cells in suspension the mean fluorescence intensity was dependent upon glucose availability (i.e., concentration) rather than to either increased growth rate or metabolic rate.

Figure 4A:
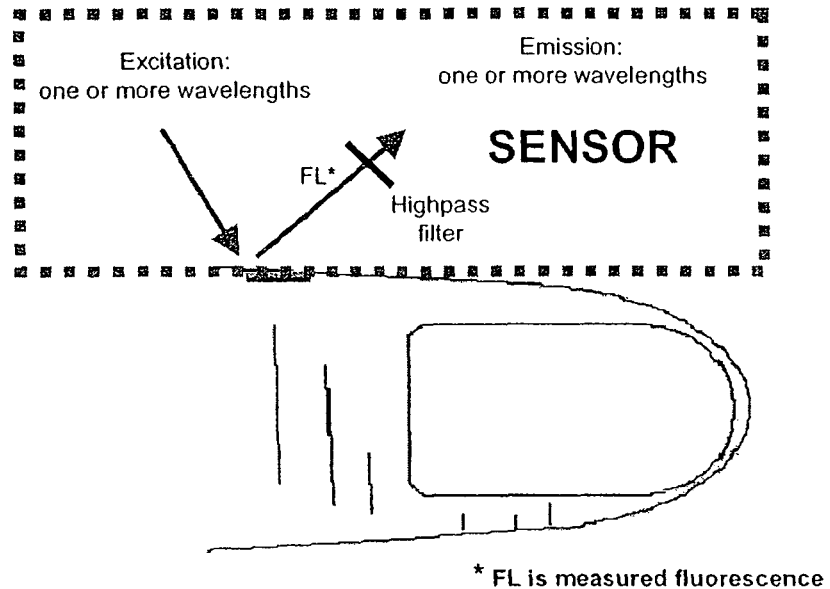
FIG. 4A and FIG. 4B are schematics showing a measurement technique for determining D-glucose concentrations utilizing one or more wavelengths.
Figure 4B:
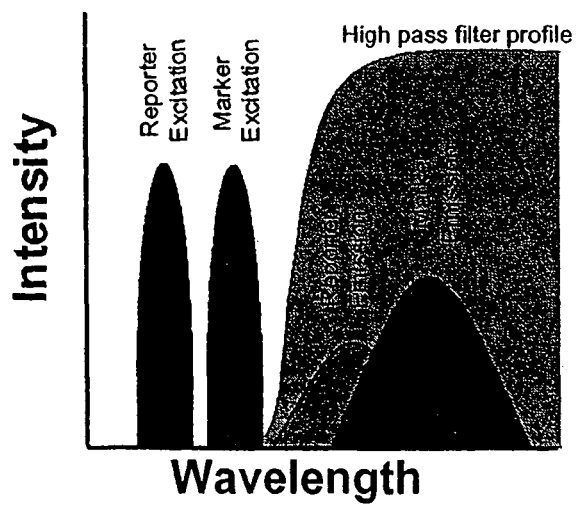
Figure 5A:
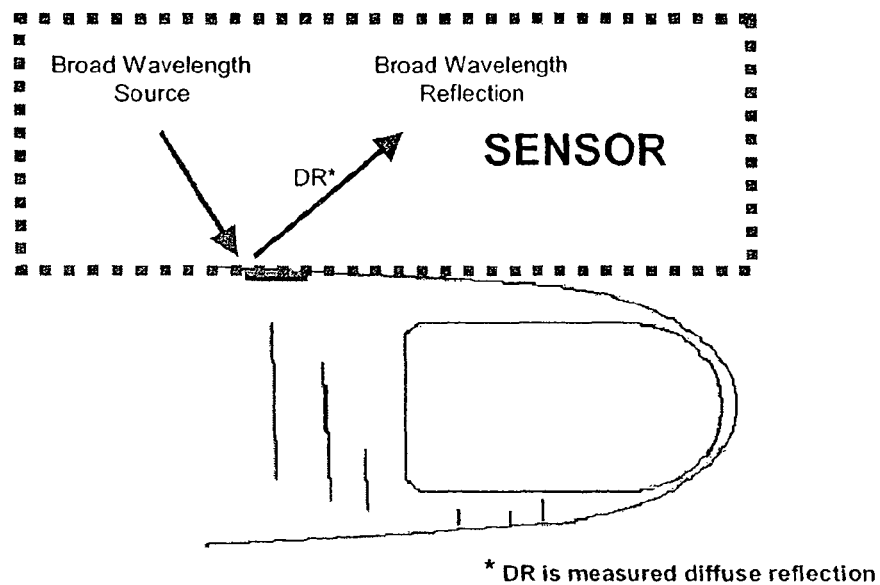
FIG. 5A and FIG. 5B are schematics showing a broad wavelength correction technique for correcting the fluorescence ratio. Corrected signal for Glucose concentration [Glucose$_C$] is a function of the ratio of reporter to marker signal corrected for variation in reflection (i.e., broad wavelength reflection) unique for each individual, such that [Glucose$_C$]= f(Reporter/Marker)×(Broad Wavelength Reflection Correction).
Figure 5B:
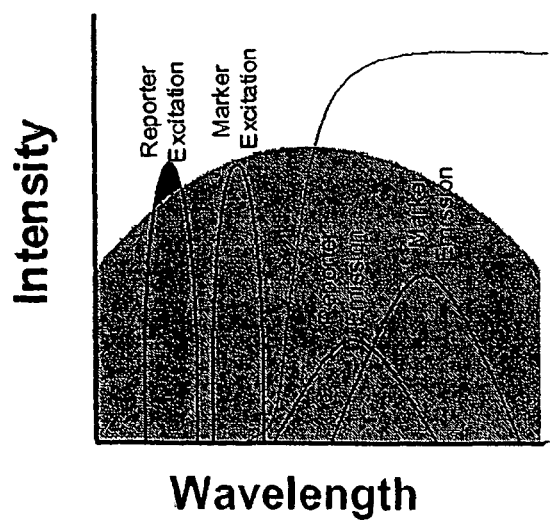
Figure 6:
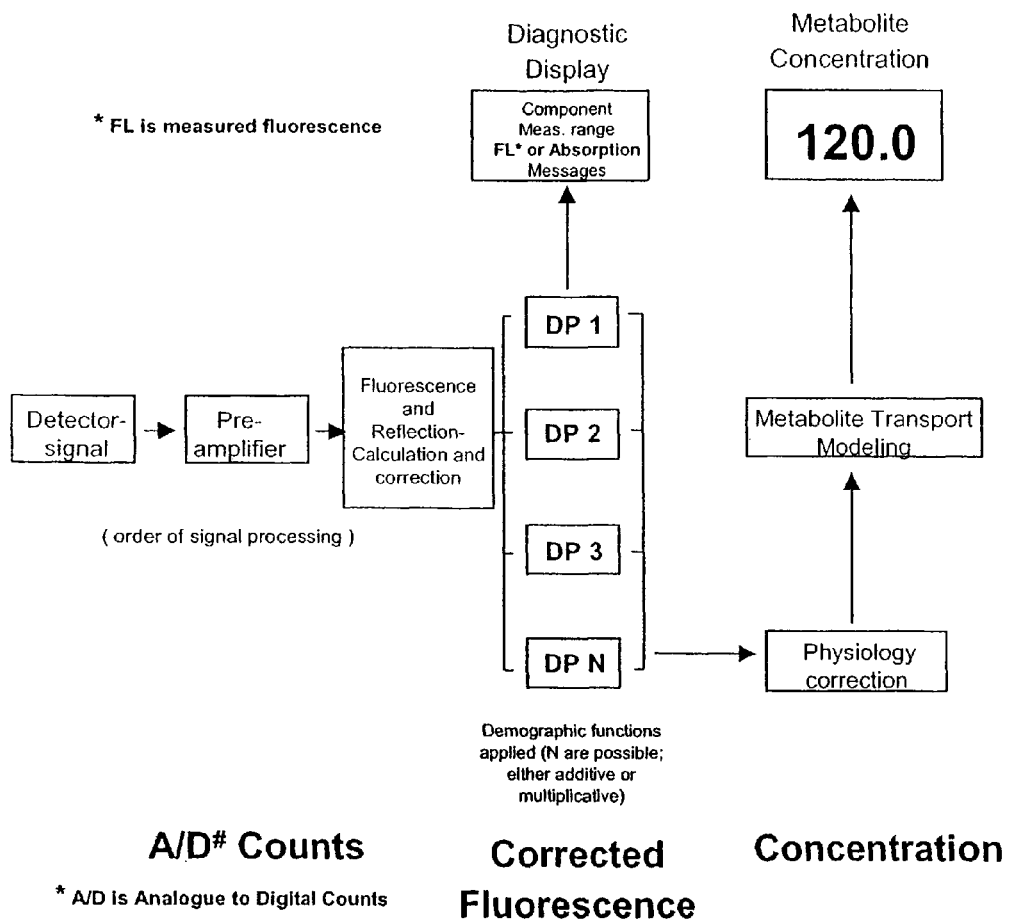
FIG. 6 is a flow chart showing signal processing logic for determining metabolite levels. The Detector signal (as fluorescence or diffuse reflectance) is pre-amplified and the initial calculation is made. One or more of a series of demographic functions (e.g., empirical modeling of different demographic clusters of the population, as shown in the figure) are applied to the initial calculation. A physiological correction is then further applied, as well as a metabolite model to derive the corrected metabolite computation (i.e., in a preferred embodiment, glucose concentration is determined)
Figure 12:
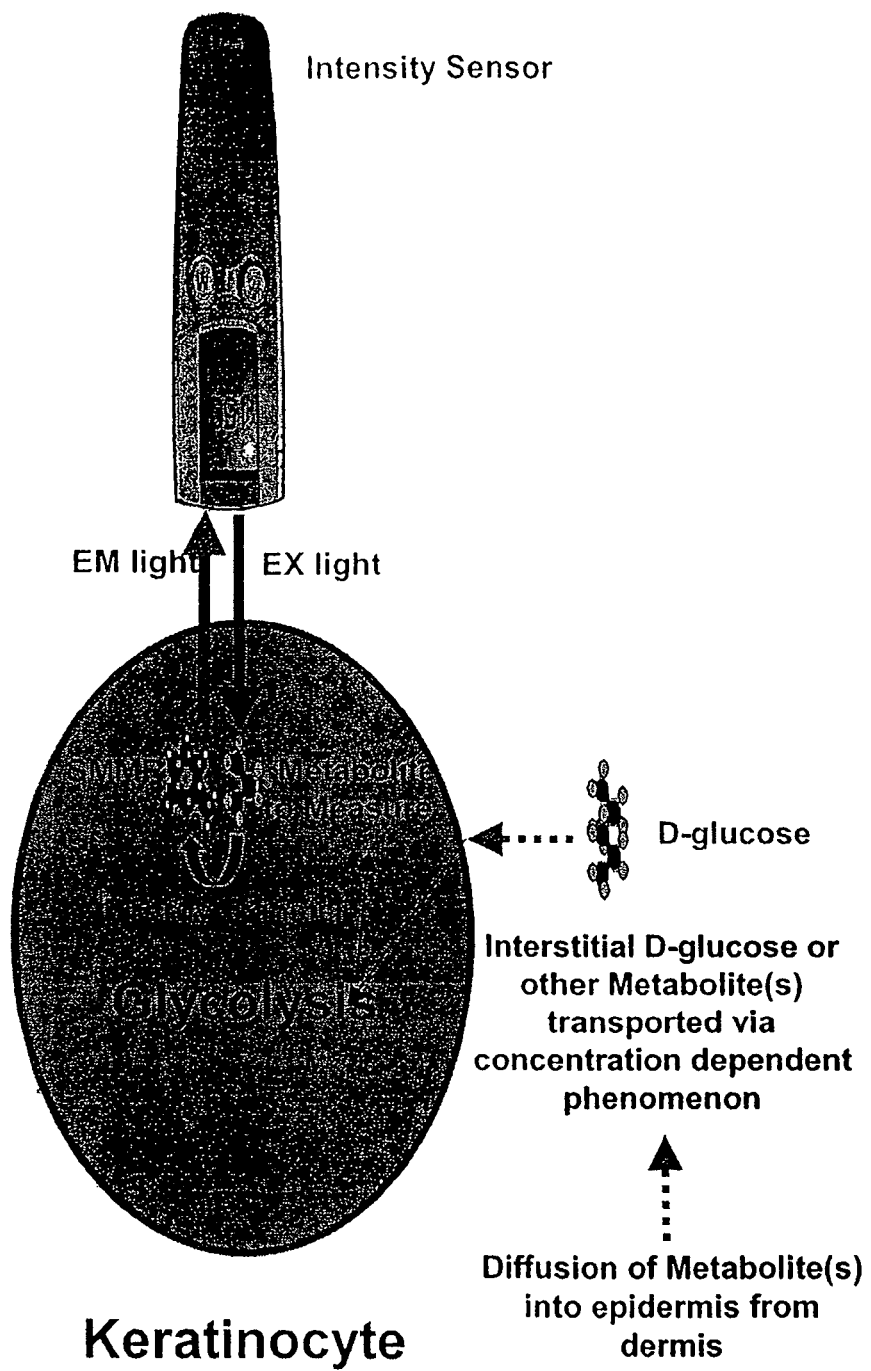
FIG. 12 is a schematic of SMMR Mechanism 1 for an indirect energy transfer reporter. SMMR energy transfer reporter mechanism for fluorescence signal detection is based upon energy transfer from a metabolite molecule to the SMMR. The metabolite molecule is excited and transfers energy to the SMMR. Then, the emission from the SMMR is detected with a sensor. Under conditions where energy transfer is a significant route for the decay of the excited metabolite, and where there is present a non-rate-limiting excess of SMMR, the emission intensity is then proportional to the concentration of metabolite present.
Figure 13:
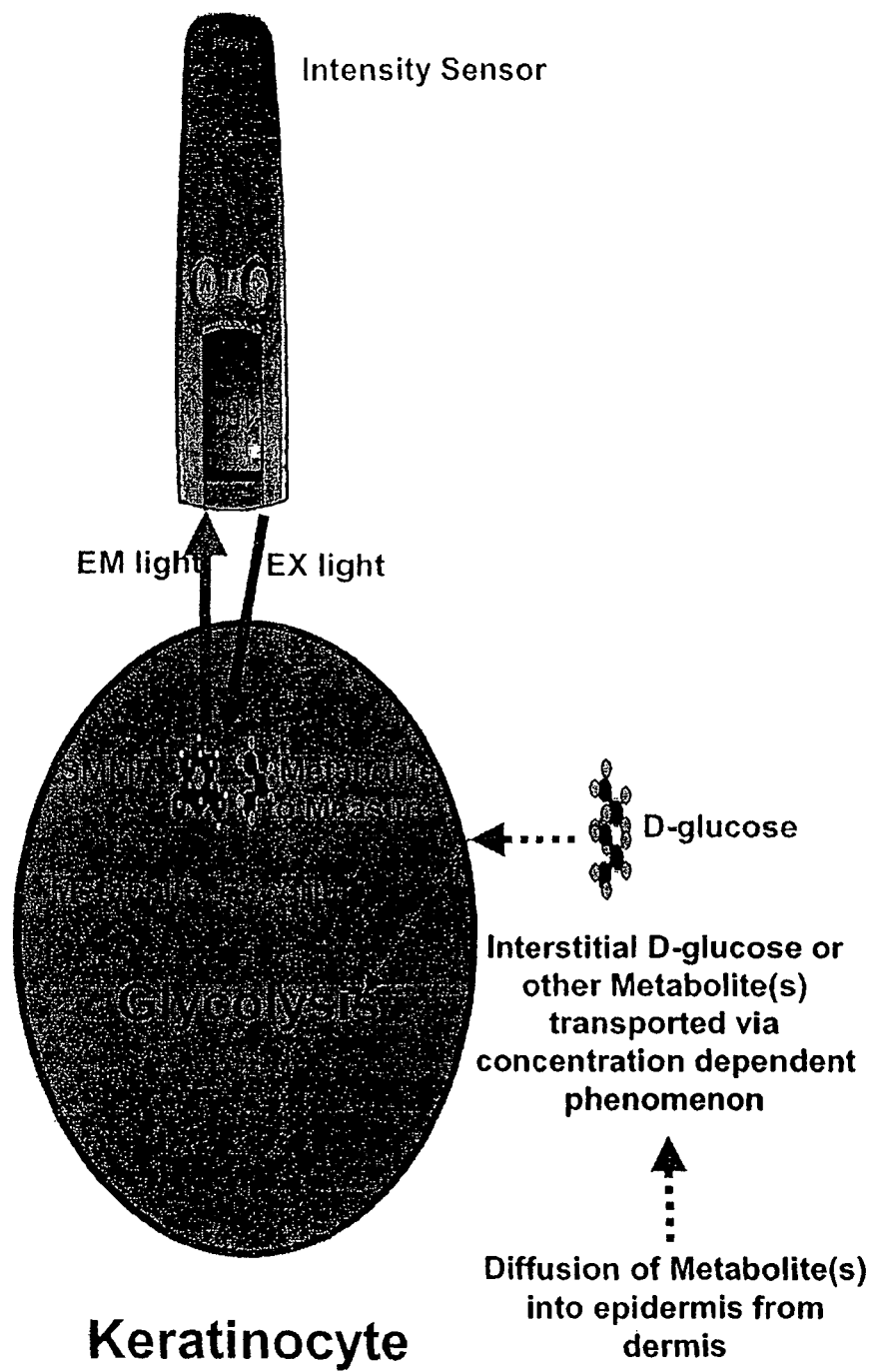
FIG. 13 is a schematic of SMMR Mechanism 2 for an indirect metabolite reporter. SMMR metabolite reporter mechanism for a fluorescence signal is based upon the influence of a metabolite molecule on the SMMR. The fluorescent SMMR is excited wherever the influence of the metabolite alters the fluorescence properties of the SMMR. This altered fluorescence emission from the SMMR is detected with a sensor. Where there is a non-rate-limiting excess of SMMR, the emission intensity is proportional to the concentration of metabolite present.

One embodiment of the invention utilizing a sensor that acts as a reporter and marker channel detector is provided in FIG. 4. The signal detected by the sensor is derived from the relaxation of a metastable excited state generated by the absorption of energy from a lamp, light-emitting diode, or laser source. The fluorescence process is repetitive, meaning the fluorescence response to glucose can be measured repetitively or continuously, as long as the molecular tag molecules are not destroyed or removed. The same molecular tag can be repeatedly excited and its emitted energy detected. In the methods and compositions of this invention, the emission intensity, given from a known concentration of at least one molecular tag, is proportional to the number of energy transfer events from NAD(P)H to Rh-123 where Rh-123 acts as the SMMR. Compounds exhibiting such a mechanism of action are representative of a family of compounds referred to as "energy transfer from reducing equivalents indicating SMMRs" (FIG. 12). The number of these energy transfer events is proportional to the rate of glycolysis modulated by the glucose concentration of the intercellular environment and ultimately to the blood glucose concentration.

The chemical structure of Rh123 is shown below as Structure A. This dye belongs to a broad range of compounds referred to as xanthene dyes. The general structure of xanthene dyes is shown in Structure B. Substitution of these dyes at any of the positions marked "R" on the xanthene moiety influences the wavelengths of absorption and emission while substitution of the phenyl ring at position 9, shown in Structure B, influences the solubility of the molecule. As drawn, the molecule absorbs light in the ultraviolet region of the spectrum. Substitution at the positions marked R with a heteroatom that readily exchanges hydrogen causes extended conjugation across the ring, wherein the molecule absorbs in the visible region of the spectrum. In the case of Rh123, the heteroatom is nitrogen and the R group may exist as an amino group or an imino group. Many xanthene dyes are amphipathic, that is, they have both polar and non-polar regions on the molecule. This property gives the molecule a high affinity for binding to the surface of biological membranes.

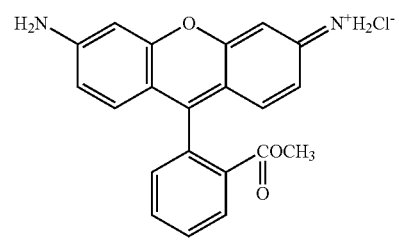

Structure A: Rhodamine 123 (Rh-123)

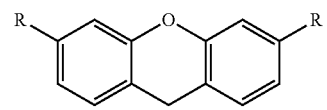

Structure B: Basic Xanthene Structure

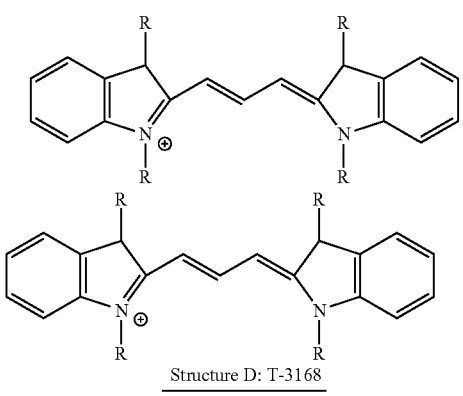

Structure C: Cyanine Dye Structure

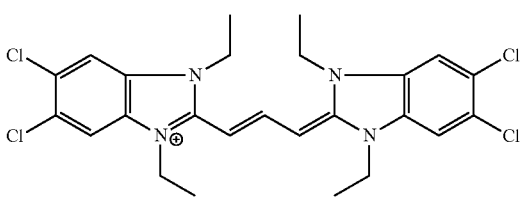 [SMILES: CCN1C(=C/C=C/c2n(CC)c3cc(Cl)c(Cl)cc3[n+]2CC)N(CC)c2cc(Cl)c(Cl)cc21]

Structure D: T-3168

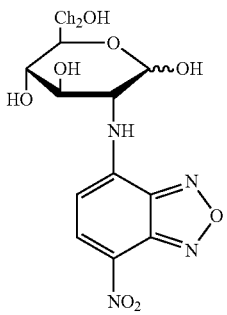

Structure E: 2-(N-(7-nitrobenz-2-oxa-1,3-diazol-4-yl) amino)-2-deoxyglucose (2-NBDG)

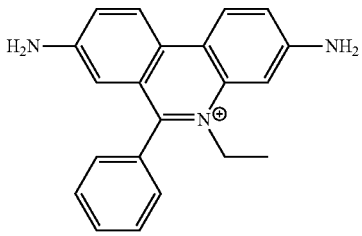 [SMILES: CC[n+]1c(-c2ccccc2)c2cc(N)ccc2c2ccc(N)cc21]

Structure F: Ethidium Bromide, Shown without the Counter Ion

Molecular structures of some of the SMMRs of the invention include those shown as Structures A-F. Other mitochondrial or membrane potential dyes useful for this invention include any molecules exhibiting properties as defined for Rh123 above (Structure A) including those mentioned here, and general compounds falling within these molecular structures, activity, solubility, toxicity, and overall action as described. Specific dyes meeting some or all of these requirements include, but are not limited to, the following.

Xanthene Type Dyes (Structure B):

Examples of Xanthene type dyes include: TMRE as tetramethylrhodamine ethyl ester, perchlorate ($C_{26}H_{27}ClIN_2O_7$. Molecular Weight 515), TMRM as tetramethylrhodamine methyl ester, perchlorate ($C_{25}H_{25}ClIN_2O_7$. Molecular Weight 501), Dihydrorhodamine 123 ($C_{20}H_{18}N_2O_3$. Mwt: 346), Dihydrorhodamine 123, dihydrochloride salt ($C_{20}H_{20}Cl_2N_2O_3$. Mwt: 419).

Cyanine Type Dyes (Structure C):

Examples of cyanine type dyes include: 5,5',6,6'-tetrachloro-1,1',3,3'-tetraethyl-benzimidazolylcarbocyanine both the chloride and the iodide salts.

Bis-oxonol Dyes

Examples of bis-oxonol type dyes include: DiBAC4(3) as bis-(1,3-dibarbituric acid)-trimethine oxanol ($C_{27}H_{39}N_4O_6$, Molecular Weight 519).

Styryl Pyridinium Dyes:

Examples of styryl pyridinium type dyes include: RH421, N-(4-sulfobutyl)-4-(4-(p-(dipentylamino)phenyl)butadienyl)-pyridinium ($C_{29}H_{42}N_2O_3S$, Molecular Weight 498.72), DASPEI as 2-(4-(dimethylamino)styryl)-N-ethylpyridinium iodide) with a molecular formula of $C_{17}H_{21}IN_2$ and molecular weight of 380 daltons, Pyridinium, 4-(2-(6-(dibutylamino)-2-naphthalenyl) ethenyl)-1-(3-sulfopropyl)-, hydroxide Di-4-ANEPPS ($C_{28}H_{36}N_2O_3S$; Molecular Weight 481).

Carbocyanine Dyes (Structure D):

T-3168 is a cationic carbocyanine dye that yields green fluorescence. It accumulates in mitochondria and is a sensitive marker for mitochondrial membrane potential. It exists as a monomer at low concentrations and forms J-aggregates at higher concentrations that exhibit a broad excitation spectrum and an emission maximum at ~590 nm.

Glucose Analog (Structure E):

2-(N-(7-nitrobenz-2-oxa-1,3-diazol-4-yl)amino)-2-deoxyglucose (2-NBDG). The 2-NBDG fluorophore typically displays excitation and emission maxima at around 465 nm and around 540 nm, respectively. It is visualizable using optical filters designed for fluorescein and is sensitive to its environment. A fluorescent nonhydrolyzable glucose analog 6-NBD-deoxyglucose (6-NBDG) is also available commercially to track glucose diffusion rates in cells. (Molecular Probes cat. no. N-23106).

Viability and Toxicity dyes (Structure F):

The cell-impermeant Ethidium Bromide is excited by an argon-ion laser and is useful for detecting and sorting dead cells by flow cytometry. It is also used in combination with fluorescein-based probes (such as calcein, CellTracker Green CMFDA or BCECF) for two-color applications, and as a marker when a reporter dye responds at only one emission wavelength.

The dyes mentioned above are available commercially in relatively pure forms from suppliers of custom molecules as well as from Biotium, Inc., 3423 Investment Blvd. Suite 8, Hayward, Calif. 94545. The preceding dyes are commonly described in the scientific literature as molecules "that stain mitochondria in living cells in a membrane potential-dependent fashion [with varying excitation and emission wavelengths]." See the Merck Index (*The Merck Index: An Encyclopedia of Chemicals, Drugs, and Biologicals*, Thirteenth Edition, Maryadele J. O'Neil, Ann Smith, Patricia E. Heckelman, John R. Obenchain Jr., Eds., Merck & Co., Inc., Whitehouse Station, N.J., USA, 2001), and other comprehensive collections of properties for organic compounds. Such references provide information regarding details of chemical and physical properties of molecules, including availability, solubility, and synthesis for each class of molecule described herein. Additional information is available from commercial suppliers, e.g., Aldrich Chemical Company, Inc., 1001 West St. Paul Avenue, Milwaukee, Wis. 53233; Sigma Chemical Co., Inc., 3050 Spruce Street, St. Louis, Mo. 63103; Fluka-RdH, P.O. Box 2060, Milwaukee, Wis. 53201 USA; Molecular Probes, Inc., 29851 Willow Creek Rd., Eugene, Oreg. 97402 USA; and other manufacturers.

Preferred dyes, acting as SMMRs according to the invention, emit fluorescence signals at wavelengths above 350 nm.

The design of specific SMMRs for particular locations and mechanisms within tissue takes into consideration the specific molecular properties of the SMMRs. Under conditions where intracellular and extracellular pH measurements are to be made simultaneously using redox potential measurements, for example, it is important that the dyes emit in different wavelength regions of the electromagnetic spectrum. The spectral regions that are preferentially selected for emission bands are bands at or about 100 nm wide and centered at or about 600 nm, 700 nm and 800 nm. These regions contain little or no autofluorescence and a relatively small and stable absorption background. These properties allow a relatively interference-free measurement of the SMMR fluorescence.

The use of known mitochondrial specific redox potential fluorescing dyes, or energy transfer fluorescing dyes for the purpose of sensing live human keratinocyte glucose metabolism in situ has not been previously described. The fluorescence intensity of mitochondrial-bound redox potential sensing dyes, as well as dyes reporting on reducing equivalents via energy transfer, are indicative of the reduction potential for the sum of oxidative phosphorylation, fatty acid metabolism, and NADH shuttling. The use of redox potential fluorescing dyes has not previously been applied in situ for direct determination of in vivo skin glucose concentration. The ability to use these dyes for such an application is based upon an understanding of skin glucose metabolism, the mechanism and importance of reducing equivalents in glycolytic metabolism of skin, an understanding of the fluorescent properties of the selected dyes, and an understanding of the optical properties of skin. In addition, these methods and compositions require a detailed understanding and optimization of dye introduction to the human keratinocyte cells; of the derivation of the appropriate conditions for temperature, pH, concentration, purity, lag times, reaction times, response times, quantum yields, optical properties of the various skin layers for the appropriate excitation and emission wavelengths, of the concentration/fluorescence response model, metabolic models for skin; and of the lag time between blood glucose and skin glucose concentrations.

One skilled in the art will recognize that the SMMR compositions and methods of the invention have both in vitro and in vivo applications. However, a unique advantage of using SMMR in clinical diagnostic and treatment applications is that their spectral response measurements are made in vivo, a distinct improvement over current in vitro analysis techniques.

Measurement of these specific analytes and metabolites, individually or combined with ancillary measurements, provides detailed information describing glucose metabolism in living tissue. The specific invention delineated here relates to the determination of blood glucose levels based upon skin glucose levels for use in the monitoring and control of diseases related to, but not limited to, diabetes mellitus, heart disease, autoimmune disease, kidney disease, memory dysfunction, cancer, stress and organ transplantation. A description of the metabolic pathways for glucose in dermis and epidermis is helpful to provide a basis for this present invention. Mechanisms operating in skin metabolism are shown in Scheme 1 of FIG. 17A. An additional overview scheme is provided in FIG. 17B. This present invention models systemic blood glucose levels based upon the application of specific first principle mathematical models to direct non-invasive fluorescence measurements made using SMMR placed within the skin.

This invention targets in vivo measurement of analyte/metabolites that provide detailed information for epidermal glycolytic pathways that are driven specifically by D-glucose, fructose, galactose and other simple sugars, but are unaffected by molecules similar to D-glucose that are not metabolically active. Such non-active metabolites include L-glucose and other levorotatory optical isomers, or enantiomeric forms of simple or complex sugars. This in fact is used as an efficacy test for the action of glycolytic reporting SMMRs. For complex glycolytic processes such as the biosynthesis of NAD(P)H, or for glycolytic processes that are distinctly non-linear, more than one pathway can be combined to enhance analytical information content to model glucose concentration. The additional information provided by monitoring more than one metabolite is used to improve analytical performance for monitoring glucose. In this way, a final measurement system provides for a wide dynamic range for glucose and is less prone to measurement errors caused by potential interferences.

Although Scheme 1 (FIG. 17A) shows that the substrate for oxidative phosphorylation is glucose-derived, this pathway may also be fueled by lipid metabolism. This is not a concern when monitoring glycolysis fueled by glucose for human or mammalian epidermal keratinocytes, since this metabolic pathway is not relevant to glucose measurement in keratinocytes, as only two percent of skin metabolism comprises this alternative lipid pathway, whereas 70% of assimilated glucose is metabolized by glycolysis, which is a metabolic process that derives energy for the cell exclusively from the metabolism of glucose. This and other details of skin metabolism can be found, e.g., in Johnson and Fusaro. *The Role of the Skin in Carbohydrate Metabolism* in: Advances in Metabolic Disorders, R. Levine (Ed.), Academic Press, 1972, 60, 1-55.

The supply of glucose in the blood both diffuses and is actively transported into the cytosol of epidermal cells. The rate of transport into the epidermis is indicative of the differential concentration of skin glucose levels and blood glucose levels. The rate of transport into skin allows for an accurate first principles mathematical extrapolation of blood glucose levels.

Once modeled, the kinetics of blood glucose transport to the skin from the blood supply of subcutaneous blood vessels enables the determination of the precise first principles mathematical relationship between the rate of change of skin glucose and the rate of change of blood glucose. Thus, rapid up or down changes in blood glucose concentration can be accurately tracked by knowing the skin glucose mean concentration levels and the rate of change of skin glucose levels. First principles mathematical models can be developed, preferably for individual patients, more preferably for small local populations, and most preferably for the universal patient case.

The invention provides at least one sensor composition that includes endogenous chromophores and exogenous fluorophore/reporters (i.e., SMMR as molecules that fluoresce as an indication of metabolic rate or by an increase in metabolite levels). By convention, factors routinely affecting the glycolytic velocity assumption set for quantitative analysis of metabolites, including lactate/W, are as follows: (1) pH generally has a small effect at less than 5% relative change between pH 7 and 8; (2) temperature has a small metabolic effect at semi-controlled temperatures (e.g., 25° C. to 27° C.); (3) enzyme/coenzyme concentration is normally in excess to allow glycolysis over all physiological ranges of glucose; (4) cellular substrate concentrations are normally in excess to allow glycolysis over all physiological ranges of glucose; (5) anaerobic/aerobic ratio for target cells of interest (e.g., epidermal keratinocytes) is assumed constant per individual; and (6) cell maturity is relatively constant and assumed to be constant over the gradient of the epidermis.

For human keratinocytes in situ, a specific layer of the epidermis (above the dermal papillae and within or above the stratum basale) is in a comparatively homeostatic condition and the major metabolic biosynthetic process is anaerobic glycolysis. This layer of cells is referred to as the stratum germinativum. Therefore, cells in the stratum germinativum make an ideal location for the introduction of SMMR into the skin. See FIGS. 1-3 and 10. Other tissues favorable for use in the methods and compositions of the invention include all those having predominantly anaerobic glycolysis as the main biosynthetic process for glucose utilization. Thus, the epidermis throughout the human skin and at all locations becomes a prospective target site for the invention. Other epithelial tissues lining cavities within the body are also target cells for the invention. These tissues include: simple epithelium, e.g., squamous, cuboidal, and columnar; stratified epithelium, e.g., squamous, cuboidal, columnar, and transitional; and pseudostratified epithelium. Preferred sites for measurement application include, but are not limited to, the fingertip, the volar forearm, the upper arm, the foot, or any location where easy access to the skin is obtained without the need to disrobe.

The transport of glucose into the cell is non-insulin regulated, and the stoichiometry of anaerobic glycolysis provides two lactate/H+ molecules per one glucose molecule. Thus, intracellular lactate/H+ measurement provides the basis for inferring interstitial fluid glucose concentration in normal keratinocytes. The direct in vivo intracellular measurements of intermediate or end-product metabolites (analytes) resulting from glycolysis within keratinocytes are thus used to infer glucose substrate concentrations within the cell in real-time without the use of invasive techniques. Endogenous, native fluorophores are not considered useful reporters of metabolic state due to low signal-to-noise and to background interferences, but they do provide information about the optical properties of the tissue and the integrated history of premature tissue glycosylation that occurs over time due to the diabetic condition.

In contrast, the exogenous molecules described herein that are added as SMMRs to the skin result in fluorescent signals that directly report on the type and level of metabolite present in the cell. The SMMRs described herein provide unique fluorescence signals that are of sufficient magnitude to be measured using standard, low-cost, commercial photonic components. By using SMMRs, the extracellular, intracellular, and organelle microenvironments can be accurately and specifically assessed for glycolytic function within a tissue or for an organism. The exogenous fluorophore/reporters are added to the skin and are used to locate and measure metabolites located within the epidermal layer of the living skin in situ, thereby indicating the metabolic state of the organism. In alternative embodiments, these dyes are applied through oral ingestion, or more preferably by passive or active topical administration.

Effective concentrations of SMMRs to be applied are in the range of at least 1 to 500 µg/ml, e.g. 5 to 150 µg/ml or 10 to 100 µg/ml. The concentration of SMMRs used is preferably from 10 to 500 µM, more preferably from 100 to 300 µM, and most preferably from 150 to 250 µM.

The methods and compositions of the invention employ the measurement of the fluorescence of SMMRs added to the skin to monitor glycolytic metabolic processes in the skin. These processes respond to blood analyte levels and to disease states affected by glycolytic activity. Autofluorescence by itself is insufficient to monitor many analytes, particularly glucose, because it does not have the necessary signal-to-noise ratio and dynamic range to be useful (i.e., accurately measured at low cost). Instead, the instant methods and compositions replace or supplement autofluorescence measurements with measurements of exogenous molecules that act as metabolite reporters localized within the epidermis.

Each of the following aspects of the SMMR system was optimized in order to derive the methods for utilizing exogenous molecule fluorescent signals in the keratinocytes for deriving blood glucose levels. The key informational requirements and assumptions include:

1. Diffusion following the laws of mass transport is the main mechanism of transport for small molecules (including D-glucose) from blood in the dermis to the keratinocytes of the epidermal layers;
2. Human keratinocytes utilize GluT1 (GenBank Accession Number: K03195) at the cell membrane (i.e., glucose transport is not insulin or GluT4 (GenBank Accession Number: M91463) regulated);
3. Glucose transport at the keratinocytes is constant relative to the maximum velocity of molecular transport and the number of active transporters within the keratinocyte cell membrane. If these are not constant, they must be modeled based upon a first principles understanding of the events that bring about changes in the transport rate. The overall effect must allow modeling of extracellular glucose levels based upon intracellular glucose levels. Thus, the intracellular glucose concentration must be based upon a known relationship to the concentration of glucose within the interstitial fluid;
4. Keratinocytes are relatively simple cells utilizing as much D-glucose as is available at any time without changing metabolic mechanisms (they remain essentially glycolytic); and they process glucose in real-time into metabolites that are directly measurable using SMMRs;
5. There is a net NAD(P)H production via the pentose shunt from glycolysis, thereby providing a mechanism for glucose measurement by using an amplified NAD(P)H signal;
6. SMMR compounds can be synthesized to demonstrate desired performance properties based upon known characteristics of molecular structure;
7. All proposed techniques using the SMMR compounds described in this invention are adaptable to small, inexpensive measurements, such as using a handheld device;
8. pH (as lactate/H$^+$), NAD(P)H, Ca$^{2+}$, FAD$^+$, ATP/ADP ratio, and redox potential can be used to directly track D-glucose concentration present in the fluid surrounding human skin keratinocyte cells;
9. For anaerobic glycolysis (i.e., the metabolism of target human skin cells or keratinocytes), pH (as lactate/H$^+$), NAD(P)H energy transfer, and redox potential provide the most rapid and trackable responses to glucose. The shortest response times are from 15 seconds to 2 minutes. SMMRs utilize three separate reporting mechanisms to report for these three glycolytic metabolites, including direct reporting, energy transfer, and redox potential, respectively;

10. There is a lag time for diffusion of glucose from the capillary fields of the dermis to the cells of the epidermis of no more than approximately 5-10 minutes for highly vascularized regions of the body, such as the fingertip;
11. Intracellular, extracellular and organelle lactate/$H^+$ is measured as a direct indication of D-glucose concentration of surrounding fluid, where lactate/$H^+$ is an indicator of keratinocyte glycolysis;
12. Measurable D-Glucose response range for these parameters is 5 to 500-plus mg/dL;
13. Human skin cells are scavenger cells, which utilize as much D-glucose as is available at any time without changing glycolytic or transport mechanisms;
14. Commercially available dye probes are useful but not optimal. Thus, strategies for independent new molecules in this regard have been developed;
15. Reporters passively transported to the skin can last up to 4 days of more using currently known methods;
16. Direct glucose measurements are possible for small treated areas of the skin but require the use of larger SMMR compounds (i.e., 100-160 kDa or more), indicating the possible requirement for electroporation schemes;
17. Small quantities of larger SMMR compounds can be optimized for signal intensity and, thus, are useful for making glucose measurements without toxicity or irritation issues in mammals, including humans;
18. A very small reaction site (i.e., 200 to 300 microns in diameter) can be used, thereby minimizing toxicity issues;
19. SMMRs as proteins, reporters and markers are placed at desired locations at the skin surface or below, namely from 10 to 500 microns in depth from the tissue surface;
20. Reporters are easy to get into the skin using passive mechanisms, but electroporation gives enhanced signal magnitudes by factor of 2 to 3 times. Electroporation is inexpensive, but adds a degree of complexity to the method;
21. None of the tested mechanisms respond to L-glucose, thereby making the tests specific for D-glucose only. (This is the 'gold standard' for testing the efficacy and veracity of any glycolytic and physiologically active glucose-concentration measuring technique);
22. Simple sugars, such as D-glucose, fructose, and galactose, are the sugars of interest relative to fueling glycolysis, and all cause glycolytic activity in keratinocytes.

Techniques for Placement of SMMRs into the Epidermis

For any of the embodiments described herein, a series of techniques exist that allow the placement of specialized fluorescent or absorptive molecules (SMMRs) into the epidermis, epithelial cells, or peripheral cells (for organs or muscle tissue during invasive surgery). Penetration of the sensor composition can be accomplished using an active transport technique, such as, for example, electroporation, laser poration, sonic poration, ultrasonic poration, iontophoresis, mechanical poration, solvent transport, direct application by painting, tattooing methods involving application by needle, an equivalent electrical tattooing technique; or most preferably by using passive transport using special solvent and reporter molecule mixtures. Passive transport may be used to allow small molecules of typically 100 Daltons (Da) to 1000 Da to enter tissues and cells.

Exemplary methods for passive transport are pressurized delivery and wicking. The method is comprised of a direct measurement of the fluorescence of SMMRs placed within epidermal cells, i.e., keratinocytes. This fluorescence is measured using molecules with specific properties for defining glucose metabolism in epidermis and for inferring the magnitude of the change in fluorescence signal to blood glucose concentrations.

Incorporation of a reporter into the tissue without use of an external device is preferred, due to the reduced cost, convenience, and ease of use. Such a passive transdermal delivery solvent system must be accurate and safe. Thus, a more elaborate solvent regime must be applied than that used for the active mechanisms such as tattooing, electroporation, and ultrasonic poration. Suitable solvent systems useful for passive transdermal delivery include creams, emulsions, and oils. These solvent systems provide passive transdermal stain delivery into the tissue at a depth of less than 50 microns. The following additives aid the process of tissue penetration for SMMR and create a diffusion rate enhancing solvent system: Soybean Oil, Hazelnut Oil, Jojoba Oil, Sweet Almond Oil, Olive Oil, Calendula Oil, Apricot Kernel Oil, Grapeseed Oil, Wheat Germ Oil, refined Light Mineral Oil, Triundecanoin (Akomed C), Undecanoic acid, Caprylic/Capric Glycerides (Akoline MCM), Caprylic/Capric Triglycerides, Propylene glycoldiester of caprylic-/capric acid, Emu oil, all as low viscosity mixtures, preferably less than 35 cSt at 35° C. In addition, mixtures of one or more of the above oils in combination with a non-polar dilution solvent can also be used. The solvent system is allowed to passively penetrate the tissue for from about 1 minute, about 5 minutes, about 10 minutes, about 30 minutes to about 2 hours to allow diffusion of the SMMR into the appropriate tissue layer(s).

In addition, penetration of the sensor composition to the desired depth can be accomplished by combining the composition with various molecular size attachments.

After the reporters are injected into, or applied to the surface of the tissue, they are allowed to penetrate in proximity to superficial cells of tissues and organs at a depth from the surface of the cells of from about 10 µm to about 1500 µm. For measurement of specific metabolites, the preferred placement of the reporters should be near the surface of the tissue (i.e., about 10 to about 175 µm) yet be representative of the overall metabolic state of the tissue in which the reporters are placed. The reporters may also be placed at a greater depth into the tissue. The precise placement of the reporters is controlled by the combination of its molecular properties, including: specific molecular size (i.e., 100 daltons to 100 kilodaltons), polarity, charge, structure, pKa, solubility, the size and type of molecular attachments or anchors, the solvent system used, as well as the specific conditions used for poration (if required). A combination of these factors provides the ability to control the location, diffusion rate, and duration or lifetime of the SMMR within the tissue or organ layers.

The dyes may be introduced into the skin by passive diffusion over a period of 24-48 hours, more preferably over a period of 2-6 hours, and most preferably in 10 seconds to 5 minutes. Contemplated diffusion times include periods less than 48 hrs, 24 hrs, 10 hrs, 6 hrs, 2 hrs, 1 hr, 30 min, 15 min, 10 min, 5 min, 1 min, 30 sec, 10 sec, or 1 sec. With passive absorption, a molecule is placed on the surface of the skin and allowed to penetrate in proximity to the epidermal cells (keratinocytes) directly above the basal layer (stratum basale) at a depth from the surface of skin from 10 µm to 50 µm and up to 175 µm in the pits of the stratum basale extending into the dermis between the dermal papillae. For measurement of glucose, the placement of the SMMR is below the stratum corneum yet above the dermis, more specifically in the stratum spinosum or stratum basale immediately above the upward extensions of the dermal papillae. This SMMR placement is accomplished by varying the combination of the polarity and charge on the SMMR, the size of molecular attachments or anchors, as well as by the polarity and hydrophilicity characteristics of the solvent system. The specific conditions for poration or passive diffusion for placement of the SMMR in the skin are controllable factors. Using any combination of these factors, it is possible to control the localization of the dye within the skin layers and target cells.

Another embodiment of the reporter application involves the use of a reservoir containing reporter, which is used to automatically or manually dispense a dose of the reporter mixture topically prior to poration or passive transport. For measurement of metabolites and precursors the reporter is placed in the tissue at a depth of up to 300 µm. A solution of 10-400 µL volume made from 1-50 µM SMMR in a solvent system penetrates into the tissue for some period of time to allow activation following passive diffusion kinetics. Once activated the change in fluorescence or absorption response of the tissue cells to changes in extracellular and intracellular metabolite or precursor concentrations is monitored directly using an optical reader. Irritant chemicals such as salicylic acid can be used to facilitate the penetration of reporters into skin or peripheral tissue.

In another embodiment, a small disposable film patch composed of polyolefin, polyester, or polyacrylate and having an SMMR dispersed into a transfer gel applied to the transfer side of the film patch, is used for SMMR application. The patch is applied with the gel side toward the skin and the gel contacts the external surface of the skin. Following the gel application, a poration or passive transfer technique is used to introduce the mixture into the appropriate skin layer(s) (as described above). Another embodiment of the SMMR application involves the use of a reservoir containing molecular tag or SMMR. This reservoir is used to either automatically or manually dispense a dose of the SMMR mixture topically prior to poration or passive transport. A non-limiting example of a topical dose is a small dot or spot from 100 µm to 5 mm. A smaller area is preferred in most embodiments, but a larger area is also contemplated. For measurement of glucose, the SMMR is placed in the keratinocytes at 30 µm to 50 µm and up to 175 µm so that placement is precisely in the specific layer of the epidermis (e.g., above the dermal papillae and within or above the stratum basale), within a comparatively homeostatic keratinocyte stratum. The molecular tag or SMMR penetrates into the skin for some period of time (depending upon molecular size and solvent mixture used) to allow activation following passive diffusion kinetics (i.e., mass transport). Once activated, the change in fluorescence response of the skin cells to changes of extracellular and intracellular glucose is monitored directly using an optical reader.

An active mechanism utilizing tissue permeation, electroporation, laser poration, or ultrasonic poration is another procedure for introducing SMMRs into the skin. Pulse lengths for poration technologies are provided below. An example of an ultrasonic poration device includes those manufactured by Sontra Medical Corporation, Cambridge Mass. Sontra and other commercial manufacturers of devices useful for this application have previously described a method for sensing glucose directly in the interstitial fluid surrounding the skin cells by removing fluid or gaining access to removed fluid for analysis. See e.g., J A Tamada, M Lesho and M J Tierney, "Weekly Feature: Keeping Watch on Glucose—new monitors help fight the long-term complications of diabetes." IEEE Spectrum Online, Jun. 10, 2003 at website: <http://www.spectrum.ieee.org/WEBONLY/publicfeature/apr02/glu.html> (last visited Jun. 26, 2003). The methods and compositions of the invention do not remove fluid but, rather, place small quantities of solution containing low concentrations of SMMRs into the skin for direct reading of the SMMR fluorescence spectral characteristics as an indication of both epidermal skin and blood glucose levels.

For some reporters above 1,000 daltons in size, electroporation may be used to introduce reporter into tissue. Electroporation has been utilized for introducing chemotherapy treatments, for introduction of DNA into living cells and tissues, and broadly recommended for introducing materials into tissues for cosmetic or medical treatment applications. If poration schemes are used, the optimized settings for an electroporation device are achieved by commercially available or by a customizable device having settings that provide conditions as described within this invention. Commercial systems utilizing a square wave voltage pulse have been described within the literature, such as those available from Genetronics Biomedical Corporation, 11199 Sorrento Valley Road, San Diego, Calif. 92121. Such a small device can be inexpensively made to have one or more constant settings for the optimized conditions disclosed for this invention.

Electroporation uses a short pulse electrical field to alter cell membrane permeability. Micro-pores form in the membrane of skin cells allowing the introduction of various molecular size mixtures into the cells at an appropriate depth of penetration for this specific inventive application. When the electric field is discontinued, the cells return to normal and one or more SMMRs introduced into the cell using the technique remains at the cellular site specifically within the epidermal cell until either the dye is chemically degraded and disposed of within the tissue or is sloughed off in a normal desquamating cycle. The process of sloughing off (or desquamation) follows a normal ten-day to twenty-day (typically fourteen-day) cycle as the residence time of epidermal keratinocytes moving from the basal layer (stratum basale) to the desquamating layer of the stratum corneum.

When employed, electroporation is optimized for use in this invention by selection of voltage range (from about 40 to 90 Volts), gap distance (from about 0 to 2 mm), pulse length (from about 150 to 250 ms), number or pulses (from about 1-10), pulse interval (from about 5 to 60 s), specific electrode design, and desired field strength (from about 40 to 60 V/cm). In addition, the selection of molecular tag molecules, solvent molecules, concentration, and lag times relative to measurement onset is determined as precisely as possible. In certain embodiments, specific parameters are determined empirically using specific solvent and SMMR selection. For example, optimization of electroporation involves the following specifications:
 1. Output voltage range: 0 to +200 VDC;
 2. Discharge capacitor (Cdis) values in microfarads are on or about: 200, 500, 700, 1000, 1200, 1500, 1700 µF;
 3. Pulse type: exponential decay;
 4. Pulse RtCdis decay time constant where Rt (total)=5+Rskin in parallel with 50 ohms. If Rskin>>50 ohms then Rt=55 ohms and Rt×Cdis=11, 27.5, 38.5, 55, 66, 82.5, 93.5 milliseconds (ms).

Electroporation also facilitates the delivery of dyes bound to large molecules that serve as anchors such as polymer beads, large polysaccharides, or colloidal particles. These approaches are contemplated as being within the invention, but are less advantageous in that the particles are often too massive to pass through the stratum corneum without active poration or mechanical injection. Once in the skin, they do not readily dissolve or organically reabsorb into the body. Such less desirable approaches would create undesirable particles that would either remain in place indefinitely or accumulate in lymph nodes, in other circulatory cavities and/or in other organ sites.

Reporters of the invention can be made with specific properties such that they are retained only within skin cells (keratinocytes) where they report on glycolytic activity and do not harm or affect cellular metabolism. These reporter compounds are sloughed off after a few days, even when permanently integrated into, or attached to, keratinocyte cells. The small quantity of reporter(s) that diffuse away from the epidermis are rapidly degraded within the body and are completely eliminated within a few days. In preferred embodiments, reapplication of the reporter(s) is relatively easy to perform. The process of sloughing off (or desquamating) follows a normal ten-day to twenty-day (typically fourteen-day) cycle as the residence time of epidermal keratinocytes moves from the basal layer (stratum basale) to the desquamating layer of the stratum corneum. Thus, reporters are developed to be applied once every 2 to 3 days, preferably every 3 to 4 days, and more preferably every 5 or more days.

The present invention introduces one or more SMMRs into the skin and then measures the fluorescence of the SMMR as an indicator of the skin glucose concentration. Electroporation can be used to introduce SMMRs into a specific skin site for measurement of SMMRs to report glucose concentration. Specifically, electroporation or passive transport via diffusion and wicking is used explicitly to introduce one or more specific molecular compounds (SMMR) and a solvent system into the appropriate skin layer in order to more rapidly introduce the SMMR for subsequent fluorometric analysis.

In another preferred embodiment, the passive transdermal delivery solvent system employed is efficacious and safe. A more elaborate solvent regime may be applied than for the active mechanisms of traditional tattooing procedures, where dyes and inks are placed into the dermis for permanent marking; or poration schemes such as electroporation, laser-poration, iontophoresis, mechanical-poration, pressurized delivery and ultrasonic poration.

The more advanced solvent systems useful for passive transdermal delivery include, but are not limited to, e.g., creams, emulsions (both oil-in-water and water-in-oil), oils (ointments), gel film patches, a reservoir device, paints, polar solvents and non-polar solvents. Non-polar solvents are preferred, as these are most miscible with the SMMRs of the invention and the stratum corneum lipids cementing the keratinocyte lamellae in place. "Lipid solvent systems" have been reported in the literature for use in transdermal drug delivery, and are composed to resemble the chemistry of stratum corneum lipids. Such a mixture may also be used to place the SMMRs into the appropriate point within the epidermis. Such a suggested mixture includes: (w/w): ceramide (50%), cholesterol (28%), palmitic acid (17%) and cholesteryl sulfate (5%). See, e.g., Downing et al.: Partition of dodecyl sulfate into stratum corneum lipid liposomes. *Arch. Dermatol. Res.* 1993, 285:151-157.

The objective of each of these solvent systems is to provide passive transdermal SMMR delivery into the skin at a preferred depth of from about 10 to 175 μM (microns), more preferred from about 20 to 100 microns, and most preferred from about 20 to 50 microns. For example, the following solvents as additives to the final SMMR mixtures are added to the skin to initiate passive transport of the SMMR to the target cellular site. The materials listed aid the process of skin penetration for SMMRs and create a diffusion rate enhancing solvent system for transdermal delivery: dimethyl sulfoxide, ethanol, isopropanol, chloroform, acetic acid, saturated hydrocarbon solvent (with from 10 to 40 carbons as linear or branched chained molecules), soybean oil, hazelnut oil, jojoba oil, sweet almond oil, olive oil, calendula oil, apricot kernel oil, grapeseed oil, wheat germ oil, refined light mineral oil and mineral oil spirits, triundecanoin (akomed C), undecanoic acid, caprylic/capric glycerides (akoline MCM), caprylic/capric triglycerides, propylene glycoldiester of caprylic-/capric acid, and emu oil. All are low viscosity mixtures, preferably less than 35 cSt at 35° C. In certain embodiments, mixtures of one or more of the above oils are used in combination with a non-polar dilution solvent.

Factors that control the depth of penetration of the SMMR and its compartmentalization into the cells and domains of the epidermis include the polarity and partition coefficient of the SMMR as well as the solvent and the molecular size. The SMMR compound may also be derivatized so that it is readily taken up by the cell and then acted upon by enzymes that chemically alter the SMMR to prevent it from leaking out of the cell. One advantage of this type of approach is that the SMMR is only taken up in its active form by viable cells. Predictive schemes for determining appropriate derivatization of SMMR compounds are provided below. Alternative methods of derivatization well known to those skilled in the art are also contemplated as part of the invention.

The physical properties of the solvent system that strongly influence permeability in the skin include the molecular size, the vapor pressure, the water solubility, and the octanol water coefficient. Smaller molecular size increases the diffusion coefficient. The vapor pressure controls the balance between diffusion into the skin and evaporation from the surface. The water solubility and the octanol water partition coefficient determine the miscibility of the SMMR solution between aqueous interstitial fluid and hydrophobic core of the cell membrane.

For a passive solvent delivery system, the depth of penetration of the SMMR is strongly dependent on the volume of solvent added. Typically, the volume of SMMR used is from 10 μL to less than about 100 μL. Preferably, the concentration of SMMR is from 10 to 500 μM, more preferably from 100 to 300 μM, and most preferably from 150 to 250 μM. Target cells are exposed to extracellular concentrations in the range of 1 to 10 μM. Dilution of the SMMR concentration arises because of the diffusion properties from the surface of the tissue to the target cell site.

The proposed volume range added to the skin or other tissue is preferably from 1 to 50 μL, more preferably from 5 to 20 μL, and most preferably from 5 to 15 μL. Alternatively, a gel patch is used containing an SMMR coated surface of approximately 6 mm in diameter consisting of a concentration of SMMR preferably from 10 to 500 μM, more preferably from 100 to 300 μM, and most preferably from 150 to 250 μM.

Solvent systems used for SMMRs may be adjusted depending upon their molecular properties and compatibility with the specific SMMR being delivered. For example, solvent hydrophobicity and polarity are noted along with the solubility properties of the SMMR, which will all have an effect on the movement of the SMMR into the tissue. Each SMMR has a certain affinity for the solvent and the tissue. The solvent's activity for delivering the SMMR directly to target tissue is a matter for empirical testing. One preferred embodiment of the invention uses an SMMR dissolved in DMSO (dimethyl sulfoxide) and further diluted in a saturated hydrocarbon solvent (with from 10 to 40 carbons as linear or branched chained molecules), or an alcohol (with from 2 to 4 carbons) at a volume ratio of 5:95 to 20:80, respectively. The optimum volume of DMSO in the delivery solvent is less than 20 percent, as the DMSO is used to facilitate dissolution of the SMMR into the carrier hydrocarbon mixture. The mixture is added to the tissue in the concentrations and volumes described above.

A gel patch may be used to apply the SMMR. In one embodiment, a gel contains the SMMR in a volatile hydrocarbon solvent in suspension with a polymer such as PVA (polyvinyl alcohol). When placed against the skin or other living tissue, the heat of the skin causes the SMMR (dissolved in the PVA-hydrocarbon solvent) to diffuse into the skin. The final diffusion depth is controlled by length of application time. Volumes below 100 µL minimize extraneous transdermal delivery and maximize delivery into the epidermis target area. Optimum passive solvent delivery is attained by using a solvent mixture or emulsion that facilitates the movement of SMMR across the stratum corneum into the epidermis, but then dissipates rapidly to limit movement of the SMMR away from the target area. Solvent systems that have the lowest toxicity include water, saturated hydrocarbon oils, polyethylene glycols and glycerol. Solvents systems that include alcohols and dimethyl sulfoxide are less favored in this application since these solvents are less biologically inert.

The SMMRs are applied directly to the surface of the skin and then passively allowed to penetrate the skin for a period of 1 minute to 5 hours, more preferably less than 4 hours, and most preferably less than 1 hour. Ideally, a solvent delivery system would be developed to provide SMMR delivery to the target tissue in less than 1 hour, more preferably less than 30 minutes, and most preferably in less than 5 minutes. This time period allows the passive diffusion of the SMMRs into the appropriate epidermal cells.

Once the one or more SMMRs are activated as a result of placement within the skin, measuring fluorescence monitors the response of the skin cells to glucose. As described herein, the fluorescence mechanism used is either a direct or indirect indication of the glucose concentration in the target cell environment. Fluorescence is typically measured using an optical reader. The optical reader calculates the skin response to glucose, applies first principles mathematical models to the response (as described below and shown in FIG. 7), and provides a determination of the blood glucose levels (See FIGS. 3, 8-9). The choice of the particular commercially available or custom designed optical reader that is compatible for use with the methods and compositions of this invention is within the ability of one skilled in the art of the invention.

The application of reporters to the glucose glycolytic pathway is illustrated in FIGS. 22 and 23. FIG. 22 illustrates the glycolytic pathway and FIG. 23 highlights the positions within this metabolic pathway that are measured using reporters (e.g., the bold, underlined, italicized molecules*). In corresponding pathways for fructose metabolism (FIGS. 24 and 25), and galactose metabolism (FIGS. 26 and 27), the reporters technique measures portions of each metabolic pathway that are highlighted similarly.

FIG. 7 is a flow chart showing signal processing logic for determining final corrected blood glucose levels from a fluorescence measurement of an SMMR in the skin or other tissue. The Detector signal (as fluorescence or diffuse reflectance) is pre-amplified and the initial fluorescence ratio calculation is made. The signal is corrected using a diffuse reflection or empirical correction scheme (*Corr.) to produce $G_C$. Next, one or more of a series of Demographic functions are applied to the initial glucose ($G_C$) calculation to obtain a demographically corrected glucose level ($G_D$). This correction takes into account optical and minor physiological differences derived for demographic groups. The $G_D$ value is then corrected for physiological differences such as exercise level, diabetes state, and health conditions resulting in a glucose value corrected for unique physiological conditions ($G_P$). The $G_P$ value is subjected to a final correction for the lag component of translating diffusion of blood glucose to skin glucose levels resulting in the final blood glucose estimation ($G_{BG}$). This result is reported as the physiological blood glucose for an individual and is considered the analytical result.

Simultaneously, a quality value is calculated telling the user the quality of the measurement taken and of the resultant glucose value reported. Based on this quality value, the user may be instructed to make one or more additional measurements until the quality value is indicative of an accurately reported glucose result.

An extension of this embodiment is the addition of SMMR molecules that are allowed to penetrate more deeply into the skin. In some embodiments, SMMR penetrate as far as the papillary layer of the dermis (upper corium), and into the reticular layer of the dermis (lower corium), up to about 300 μm. In other embodiments, SMMR are applied into the subcutaneous layers of the skin. In further embodiments, injection or ingestion of reporter molecules into the bloodstream, or into specific organs or tissues, is utilized. The resultant fluorescence response is measured at the site of application, e.g., by using an optical reader with remote optics (i.e., optical waveguides).

In alternative embodiments, the tissue being monitored is exposed, as in surgery or injury, or viewed remotely using invasive fiber optics, light pipes, or camera-based remote optics.

The SMMRs may be applied directly to the tissue of a subject or is integrated into paint or gel. The paint or gel containing the SMMR is placed directly on the stratum corneum (outer skin) at one or more of several recommended sites. These sites include, but are not restricted to, e.g., the fingertip, the volar forearm, the upper arm, the foot, or any location where easy access to the skin is obtained without the need to disrobe. An added advantage for such a choice of location is to not induce embarrassment when in public display. A preferable location is on the side of the finger, where SMMR are tagged just above the first knuckle. This avoids both inconvenience to the user and contamination brought about by prevalent use of the fingertip for routine activities. The volar forearm may also be used but is less preferred due to a decrease in vascularization at this skin site. The fingertip area is most preferred due to its increased relative vascularization as compared to the volar forearm and due to its convenience as a personal monitor site for both public and private use.

Specialized methods using painless jet injection for placement of reporter into the tissue are also encompassed by the invention. However, such techniques are not preferred, due to the high initial cost of the device. Multiple versions of jet injectors are commercially available (e.g., the INJEX™ developed and made available to the European market by RÖSCH AG Medizintechnik i.G.)

SMMR may be packaged and sold in any clinically appropriate manner known to those skilled in the art, including in individual containers or in kits, and with or without disposable or non-disposable applicators. A disposable applicator containing a solvent mixture, including but not limited, e.g., to a liquid or gel, and containing one or more SMMR, can be placed directly onto the outer skin and allowed to remain in place for a period of time. The time required for the SMMR to become activated is typically from 1 sec to 3 hrs, preferably less than 2 hrs, less than 1 hr, less than 30 min, less than 10 min or less than 5 minutes.

The mechanism of action of the SMMR is to act as an in vivo fluorescence reporter for metabolites that are stoichiometrically proportional to other non-fluorescent metabolites that are part of well characterized metabolic pathways (such as glycolysis). These stoichiometric relationships are most applicable when operative in living systems. These mechanisms and the techniques used to target these pathways are summarized in Scheme 1, FIGS. 10-17.

Mitochondrial Membrane Redox Potential

Once introduced to the epidermal intercellular fluid and keratinocytes, the SMMRs will migrate preferentially to the target cells and cellular structures of the live epidermal cells (keratinocytes), which are directly above the basal layer (stratum basale). For effective measurement of glucose, the placement of the SMMR is preferably below the stratum corneum yet above the dermis, more specifically above the dermal papillae, because the device measures the glycolytic/metabolic activity of living cells, and the cells in the stratum corneum are essentially dead. The use of dyes that require activation by metabolic processes within the cell limits background interferences from a SMMR that has penetrated into dead tissue. Therefore, the methods and compositions of this invention are also useful for distinguishing between live and dead tissue using the principle of activation by metabolic processes. For example, SMMRs used as metabolic reporters will report the level of metabolic activity in target cells whether dead, normal, hypo-metabolic, or hyper-metabolic. This is due to the surprising discovery that SMMR-treated tissue provides unique spectral responses for metabolically active living tissue that are significantly different from the spectral responses from dead tissue. SMMRs that provide the most useful spectral responses include, but are not limited to, molecules providing fluorescence reporting of reducing equivalents, reduction-oxidation potential, and the presence of metabolites actively produced during biosynthetic processes such as glycolysis.

The SMMRs selected for use in the methods and compositions of the invention should have an affinity for the keratinocyte target cells and cellular structures located within the stratum spinosum. In some embodiments, the SMMR remains in place for several hours and/or throughout the life cycle of the epidermal keratinocyte cells and is eventually sloughed off as part of the desquamating layer of the stratum corneum. Epidermal keratinocytes have an average lifespan of 14 days, ranging from 4 to 20 days, and even up to 30 days, depending upon the individual subject skin health conditions, physical abrasion, or unprotected use of caustic or acidic chemicals on the skin. In most embodiments, the SMMR is introduced in low concentration, typically from 10 µM to 500 µM, at nominal volumes from 200 µL to 5 µL, respectively. The insertion of the SMMR within the epidermis provides an added safety feature, such that only short-term exposure to the SMMR occurs at any potential measurement site. In certain embodiments, the final interstitial fluid concentration of SMMR used is from 0.01 to 500 µg·ml$^{-1}$, more preferably 1 to 100 µg·ml$^{-1}$, and most preferably 5 to 20 µg·ml$^{-1}$, based upon a molecular weight of approximately 380 Daltons for the SMMR. These concentrations apply irrespective of the molecular weights of the SMMR, which range from approximately 100 Da to approximately 250 kDa. For the invention, the SMMR for these molecular weight ranges can be placed into target tissues for reporting of glycolytic activity or other metabolic processes. Dosage of the SMMR solution involves adding 1 to 100 µL to a spot that is 0.1-5 mm in diameter, preferably less than 2 mm in diameter. One skilled in the art will be able to modify these dosage requirements based on empirical test results for specific metabolic reporting applications and signal intensity requirements.

Direct Measurement of Glucose using the Sensor Compositions of the Invention

In another embodiment of the invention, glucose levels are measured using a direct mechanism for in vivo fluorescence measurement of glucose. Direct measurement technologies utilize a mechanism for fluorescent spectra that responds directly to the glucose molecule itself, rather than ones that respond to changes in a related metabolite or analyte. The methods involve applying the sensor composition of the invention to a surface of the skin for a predetermined period of time, causing penetration of the sensor composition to a depth of about 10 µm to about 175 µm, monitoring a change in glucose concentration in the skin by detecting changes in the fluorescence or absorption, and correlating the glucose concentration within the skin with blood glucose levels, thereby determining the concentration of glucose in the blood. However, depths up to about 300 µm are also contemplated as part of the invention.

Accordingly, the present invention provides materials, apparatuses, and methods for several non-invasive techniques for determining in vivo blood glucose levels based upon the direct measurement of glucose levels present in the skin. These methods use reporters of the invention to determine glucose levels in the skin, which may then be correlated to blood glucose levels as described herein.

Sensor compositions are disclosed, wherein one or more reporters are deposited at a depth from the surface of the skin of from about 10 µm to about 175 µm in the epidermis at an effective concentration. However, depths up to about 300 µm are also contemplated as part of the invention. When the reporter contacts a molecule of glucose, a change in fluorescence or absorption of the one or more reporters occurs, thereby allowing quantification of the change in fluorescence. The measured change in fluorescence is indicative of the total glucose concentration within the skin. The quantification of the change in fluorescence is performed using fluorescence or absorption spectroscopy, or an equivalent wavelength emission detection technology.

As one or more reporters are deposited at the epidermis, the fluorescence response is measured using a handheld sensor, preferable a low cost handheld sensor. Reporters are preferably relatively small entities of specific molecular size, polarity, charge, and structure, which undergo a change in fluorescence or absorption when brought in contact with an analyte molecule.

These methods utilize glucose oxidase or modified glucose oxidase to measure skin glucose in vivo by reacting SMMRs directly with glucose within the skin to form a colored or fluorescent product. The quantity of color change or fluorescence is indicative of the total glucose concentration within the skin. The skin glucose thus determined is used to infer blood glucose levels as calibrated and described herein. A SMMR fluorophore can be intercalated into glucose oxidase at the FAD site or secondarily attached to the periphery of the molecule where it fluoresces when brought in contact with a specific analyte molecule or a byproduct of a reaction of the fluorophore-attached enzyme with the analyte molecule.

The one or more SMMRs used in this aspect of the invention include, for example, Glucose Oxidase-Labeled Fluorophore (GO-LF) and Glucose Oxidase-having FAD in the triplet state (GOx-$^3$FAD*).

The use of a Glucose Oxidase-Labeled Fluorophore (GO-LF) or Glucose Oxidase—with a photooxidizable cofactor (such as FAD), or another intercalated fluorophore, provides detailed information regarding in vivo glucose levels in the picomolar through millimolar range in living skin tissue, interstitial fluid, or blood. Measurement and determination of blood glucose levels, based upon skin glucose levels, is a valuable tool in the monitoring and control of diabetes mellitus. According to the present invention, specific first principle mathematical models are applied to the direct noninvasive determination of skin glucose levels in order to model the blood glucose levels.

In another embodiment of this invention, methods for monitoring blood glucose levels using photo-induced electron transfer are described. These methods, as an exemplary fluorescence-labeled protein SMMR is used, such that the reaction of glucose with the triplet excited state of the FAD moiety contained with the glucose oxidase protein (GOx-$^3$FAD*) may be monitored kinetically by a reduction in the lifetime of the triplet state and under steady state conditions by a decrease in the triplet absorption. This measurement of the triplet state of FAD for glucose monitoring is provided. The skin glucose thus determined is used to infer blood glucose levels.

Figure 7:
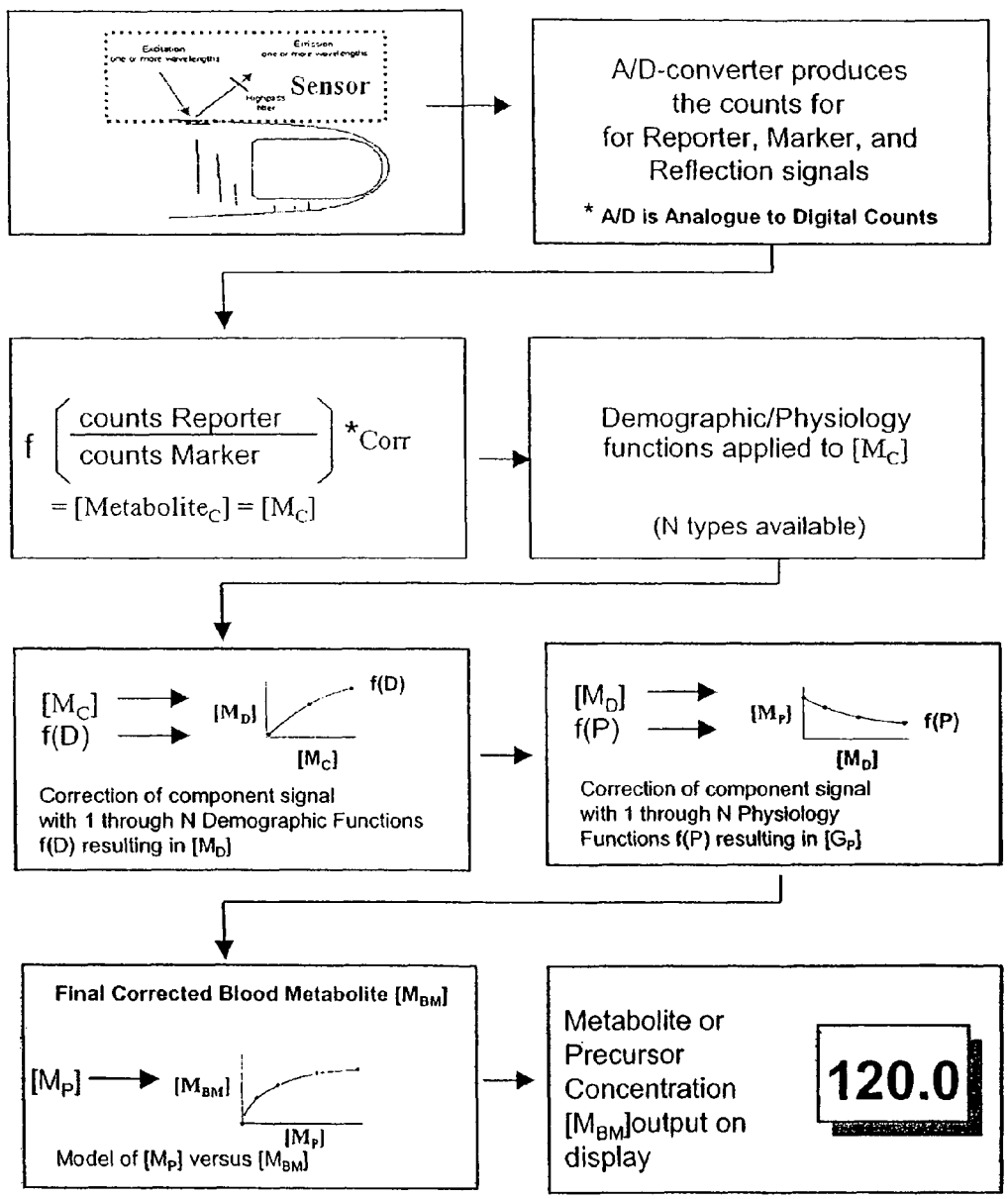
FIG. 7 is a flow chart showing determination of metabolite concentration. The Detector signal (as fluorescence or diffuse reflectance) is pre-amplified and the total fluorescence counts are determined. The initial calculation is made and is corrected using the diffuse reflection information as per FIGS. 5A and 5B. Demographic and physiology functions (e.g., empirical modeling of different Physiological clusters of the population, as shown in the figure) are then applied to correct for individual skin optical properties and unique physiology. The corrected metabolite levels are then subjected to a final correction model relating measured skin metabolite levels to blood metabolite levels (lag correction). The result is a blood metabolite computation derived from a measurement of skin fluorescence (i.e., in a preferred embodiment, glucose concentration is determined)
Figure 8:
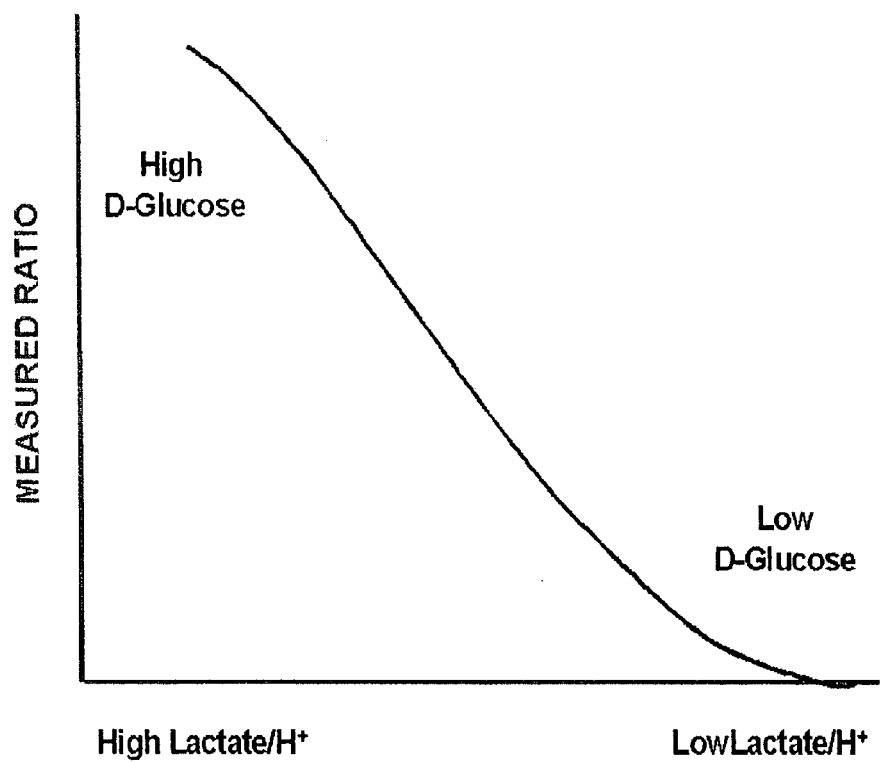
FIG. 8 is a schematic showing blood glucose concentration determination using measured fluorescence ratio versus D-glucose. The measured ratio response versus D-glucose changes as a function of changing blood glucose concentration. Also shown is the corresponding relative lactate/H$^+$ concentration.

In yet another embodiment, protein-labeled fluorophores and proteins comprising a photooxidizable cofactor (such as FAD), or proteins comprising another intercalated fluorophore are provided as direct reporters of glucose or glucose metabolic products throughout the anaerobic or aerobic glycolytic pathways. Preferably, these reporters would indicate quantitative levels of D-glucose (FIG. 7).

The supply of glucose at the epidermis is provided by mass transport from the blood vessels and capillary fields located within the dermis, immediately beneath the epidermis. The movement of glucose from the blood stream to the epidermis is concentration-dependent, rather than insulin-regulated, thereby allowing the skin glucose levels to provide the basis for measurement of blood glucose as a direct inference from skin glucose measurement. The rate of glucose transport into the epidermis is indicative of the differential between skin glucose and blood glucose levels. Thus, the rate of transport into skin allows an accurate extrapolation of blood glucose levels using first principles mathematical extrapolation techniques. Once modeled, the kinetics of blood glucose transport to the skin from the blood enables the determination of the precise first principles mathematical relationship between the rate of change of skin glucose concentration and the rate of change of blood glucose concentration. Thus, rapid blood glucose concentration changes up or down are accurately tracked by determining the skin glucose mean concentration levels and the rate of change of skin glucose levels. First principles mathematical models can be developed for the individual case, preferably for small local populations, and most preferably for a universal patient case.

The use of fluorescence and absorption of endogenous and exogenous chromophores and fluorophores is directed by known metabolic pathways that operate in living tissue. The interpretation of these data and the application of the invention to the monitoring of in vivo analytes, particularly glucose, is simplified by the use of mathematical models of these metabolic processes. A number of computer models of these processes which vary in complexity and include: glucose transport, glycogen synthesis, lactate formation and transport, oxidative phosphorylation and the generation of reducing equivalents in tissue have been reported. These models are used to identify the optimum experimental conditions to measure an analyte concentration in particular the blood glucose concentration.

The glucose oxidase is reacted with glucose containing flavin adenine dinucleotide (FAD) to generate the triplet state of FAD denoted as $^3$FAD*. The $^3$FAD* reacts with molecular oxygen (O$_2$) and glucose. The reaction of the $^3$FAD* with glucose may be monitored kinetically using low-cost instrumentation by measuring a reduction in the lifetime of the triplet state. Under steady-state conditions the reaction of glucose and $^3$FAD* can be monitored by a decrease in $^3$FAD* absorption.

It has been shown that fluorophores, or colored dyes utilizing absorption spectroscopy, can be used to measure glucose in solution or serum by using a series of separate reagents. These generic reagents include glucose oxidase (which oxidizes glucose forming hydrogen peroxide); peroxidase (generally horseradish peroxidase: HRP) used to create an oxidizing reaction in the presence of hydrogen peroxide with the dye or fluorophore and a dye reagent or fluorophore, which changes its color or fluorescence spectrum when brought in contact with hydrogen peroxide, and peroxidase. The resultant colored or fluorescent species is measured with a calorimeter or fluorometer, and the amount of glucose in solution is calculated. In addition, other analytical techniques have been shown to be commercially useful for measuring hydrogen peroxide generated from the reaction of glucose oxidase and glucose.

In one embodiment, a small molecule metabolic reporter (i.e., Glucose Oxidase-Labeled Fluorophore: GO-LF), when brought in contact with glucose, forms a fluorescent species. The GO-LF molecule is in the form of glucose oxidase protein whereby a fluorescent cofactor analog is incorporated as a substituent molecule (SubMol) to the enzyme cofactor flavin adenine dinucleotide (FAD). One advantage of the present invention is the increased sensitivity of 10-100 times the former visible color reaction, smaller analyte concentration requirements (pM vs. μM or mM of glucose), and greater simplicity of the chemical strip system (i.e., a single reagent versus multiple reagents as described in detail herein). This sensor or reader measuring the strip response requires less sample volume, less sensitivity, and less power than previous strips while yielding improved accuracy.

The basic science required to add dyes to protein molecules has been previously described and are well known to those skilled in the art. See, E. Katz et al. Glutathione reductase was transformed into a 'photoenzyme' by tethering to the protein photoactive eosin dye units (Eo$^{-2}$) with the resulting mechanism of the enzyme photoactivation summarized.

One embodiment of this invention employs a specific enzyme (i.e., glucose oxidase), whereby a specific fluorescent cofactor analog is incorporated as a substituent to the enzyme cofactor flavin adenine dinucleotide (FAD). This molecule is then deposited into the skin of a living individual, and is used for the purpose of detecting glucose in the skin fork predicting blood glucose levels. The concept of creating this specific molecule for incorporation into a living organism for routine monitoring of glucose levels is unique.

The reaction between glucose and the excited triplet state of the cofactor within the protein is detected in a method for in vivo, non-invasive glucose or glucose-pathway derived metabolite detection in living organisms.

Glucose Monitoring Using Glucose Oxidase-Labeled Fluorophore (GO-LF)

Many current commercially available blood glucose test strip products utilize a well-known color reaction caused by the presence of glucose in a body fluid sample drawn from interstitial tissue fluid or from blood. This reaction is described as the formation of hydrogen peroxide from the reaction of dissolved or suspended serum glucose with a test strip containing glucose oxidase. Glucose oxidase, a flavoenzyme, catalyzes the following reactions as shown in M9, M10 and M11 below:

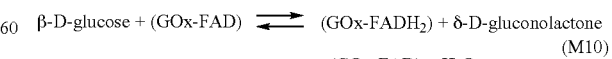
(M9)
β-D-glucose + (GOx-FAD) ⇌ (GOx-FADH$_2$) + δ-D-gluconolactone

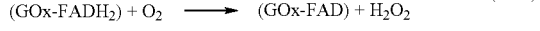
(M10)
(GOx-FADH$_2$) + O$_2$ ⟶ (GOx-FAD) + H$_2$O$_2$

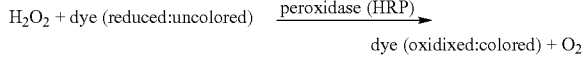
(M11)
H$_2$O$_2$ + dye (reduced:uncolored) $\xrightarrow{\text{peroxidase (HRP)}}$ dye (oxidixed:colored) + O$_2$ The stoichiometric formation of hydrogen peroxide in proportion with molar serum glucose concentration is detected by the addition of peroxidase (generally horseradish peroxidase: HRP) to form a colored component when further reacted with an indicator (i.e., an oxidizable dye). The additional extraneous oxidation of the colored dye is inhibited using a color stabilizing reaction. Thus, the peroxidase catalyzes the oxidation of an indicator in the presence of hydrogen peroxide while the final color-changing reaction is stabilized.

The present invention eliminates the color reaction step by reacting a Glucose Oxidase-Labeled Fluorophore (GO-LF) directly with glucose yielding a fluorescence response. One advantage of the present invention is the increased sensitivity of 10-100 times the former visible color reaction, smaller analyte concentration requirements pM versus μM or mM of glucose, and greater simplicity of the chemical strip system (i.e., a single reagent versus multiple reagents). The sensor or reader measuring the strip response requires less sample volume, less sensitivity, and less power than previous strips, while yielding improved accuracy. The invention is described using descriptive text equation form as: 1 Glucose plus 1 Glucose oxidase labeled fluorophore (GO-LF) yields 1 Hydrogen peroxide; 1 Hydrogen peroxide plus 1 GO-LF yields 1 GO-LF* (Fluorescence signal); and by using the more detailed chemical symbols as reactions M12, M13 and M14:

  (M12)

  (M13)

  (M14)

Hydrogen peroxide is measured using the enzyme catalase combined with an oxygen sensing fluorophore (FL) such that a fluorescence signal, molecular oxygen, and water are generated from the reaction shown as M15:

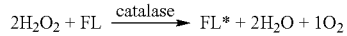  (M15)

Multiple fluorescence sensors or molecules can be used for detection of hydrogen peroxide or oxygen once formed from the reactions of glucose and GO or hydrogen peroxide and catalase, respectively. Addition of glucose to a solution of glucose oxidase causes an increase in fluorescence after a lag time. The lag period can be related to the concentration of the glucose oxidase, the oxygen concentration and the glucose concentration. Assuming that the rate constant for the reoxidation of the reduced enzyme is significantly greater than the binding and oxidation of glucose, and that the concentration of the free oxidized enzyme is higher than that of other forms before the time at which the fluorescence changes, then the following expression shown as M16 has been derived. See for example, Q. H. Gibson et al., Biol. Chem. 239:3927, 1964; and J. F. Sierra et al., Anal. Chem. 69:1471, 1997. It should be noted that the measurement of oxygen within the tissue is required for optimum utilization of equation M16 for determination of glucose concentration.

$$t_m - t_0 = \frac{1}{k_1 [GO_x]_0} \ln\left(\frac{[G]_0}{[G]_0 - 2[O_2]_0}\right)$$  (M16)

where $t_m$ Time between the change in glucose and the time at which the fluorescence changes;

$t_0$ Time at which glucose changes;

$k_1$ Rate constant for the reduction of $GO_x$ by glucose;

$[GO_x]_0$ Initial concentration of glucose oxidase;

$[G]_0$ Initial concentration of glucose; and $2[O_2]_0$ Initial concentration of oxygen.

Figure 38:
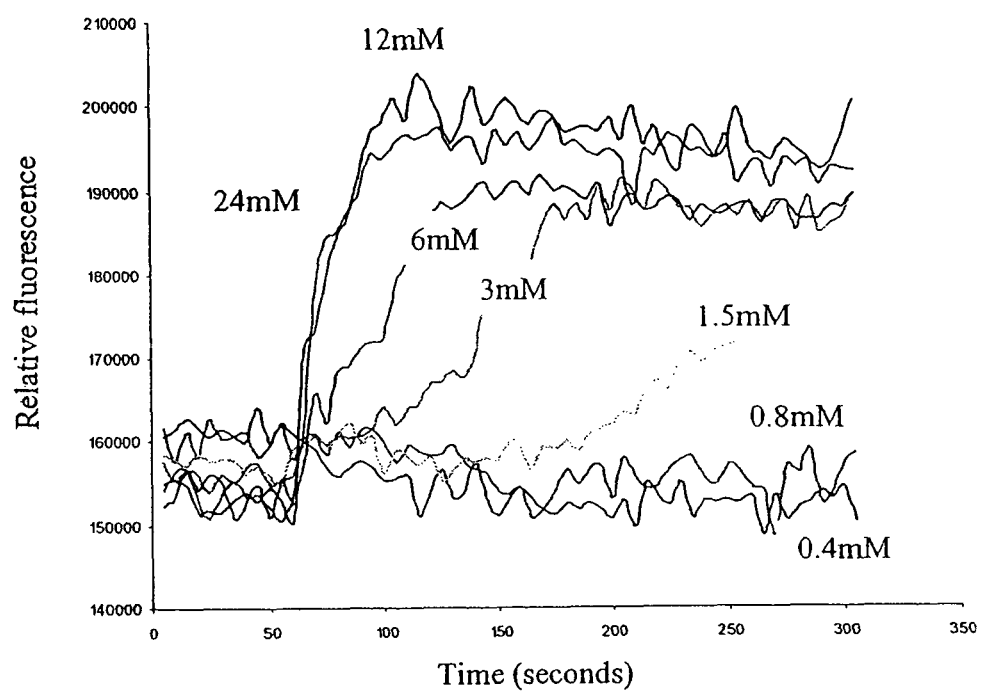
FIG. 38 is a graph showing how the intensity of fluorescence is indicative of the glucose concentration and this measurement may be combined with the dynamic measurements to determine glucose concentration.

The application of this analysis to the in vitro measurement of glucose is shown in FIG. 38

With the concentration of glucose oxidase and oxygen used in this experiment, the experiment is most sensitive over a glucose concentration range of about 18-216 mg/dL, i.e., about 1 mM-12 mM. This range can be adjusted by changing the glucose oxidase concentration. The actual concentration of glucose oxidase is determined from diffuse reflectance. It can be seen from this data that the intensity of the fluorescence is also indicative of the glucose concentration and this measurement may be combined with the dynamic measurements to determine glucose concentration.

Energy transfer within the GO-LF molecule mediates the GO-LF fluorescence intensity. Because of this, it is proposed that the fluorescence of GO-LF reports the in vivo reaction of glucose with glucose oxidase in the presence of molecular oxygen (occurring within skin tissue or the surrounding tissue fluid).

The specific fluorophores useful in the methods and compositions of this aspect of the invention include any number of a group of fluorophores having a three-ring structure similar to that demonstrated by the fluorescent moiety of FAD as an enzyme cofactor substituent molecule. This fluorophore is inserted into the FAD location within the glucose oxidase molecule (protein) structure and is here termed the substituent molecule (SubMol). These principles for glucose determination are described herein and are illustrated in FIGS. 18 through 21.

Examples of SMMR suitable for direct glucose measurement include Glucose Oxidase-Labeled Fluorophore (GO-LF), Glucose Oxidase-Intercalated Fluorophore (GO-IF), Glucose Oxidase-having FAD in the triplet state (GOx-$^3$FAD*), or another protein designed to act as a molecular sensor by substitution of a fluorophore into the protein so as to produce and optimize an optical signal when an analyte molecule is inserted into a protein specific binding site.

The types and groups of molecules useful as fluorescent SubMols are illustrated in structures G through J. It should be noted that one skilled in the art could employ these methods to similar biomolecules and protein variants to achieve similar results.

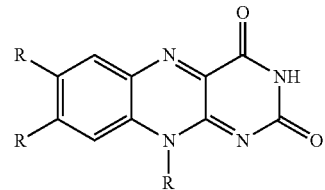

Structure G: Structure of FAD FL SubMol Moiety

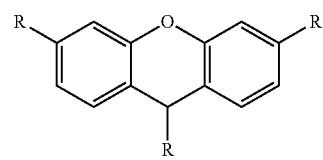

Structure H: Structure of Basic Xanthene Molecule Useful as a Core SubMol Structure

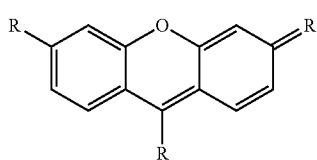

Structure I: Generic Fluorophore Structure I for SubMol Candidate

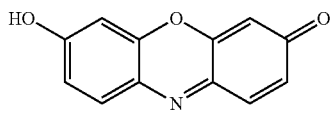 [SMILES: O=c1ccc2nc3ccc(O)cc3oc-2c1]

Structure J: Generic Fluorophore Structure II for SubMol Candidate

It should also be noted that a variety of proteins could be used to create small molecule metabolic reporters for many other analytes, including, but not limited to the following examples. Thus, one skilled in the art could utilize anyone of these molecular sensors to create in vivo, low-cost, non-invasive metabolite sensors.

Reporters designed for fluorescence detection of reactive species (RS) such as hydrogen peroxide ($H_2O_2$), molecular oxygen ($O_2$), hydroxyl radical (HO*), peroxyl radical (HOO*) singlet oxygen ($^1O_2$) and superoxide anion ($*O_2^-$) can all be used to measure glucose concentration based on stoichiometric formation of colored or fluorescent species. The colored or fluorescent compounds result from the reaction of the fluorophore or colored compound with hydrogen peroxide, which is formed from the reaction of glucose with the glucose oxidase portion of the GO-LF molecule. The reporter will yield a fluorescence signal when placed in near proximity to the reactive species. Molecular structures useful for SubMol insertion for specific detection of the reactive species described herein can be obtained commercially from suppliers such as Molecular Probes, Inc., 29851 Willow Creek Rd., Eugene, Oreg. 97402 USA. Other suppliers may provide similar molecules also useful for detection of RS.

Electrochemical sensors can also be used to detect this hydrogen peroxide after a reaction of glucose with glucose oxidase in ex vivo body fluids that were removed from the skin. See, e.g., S. Gebhart et al., Glucose Sensing in Transdermal Body Fluid Collected under continuous vacuum pressure via Micropores in the Stratum Corneum.

Many enzymes, especially redox active enzymes, utilize cofactors to facilitate their catalytic activity. These factors are not amino acids but are often redox active species. Common cofactors and the enzymes they are found in include, but are not limited to:

1. NADH
   Alcohol dehydrogenase, Lactate dehydrogenase
2. FAD
   Glucose oxidase, Malate dehydrogenase, Cholesterol oxidase
3. Thiamine pyrophosphate
   Pyruvate dehydrogenase
4. Heme
   Cytochrome c peroxidase, Chloride peroxidase, Hemoglobin (Oxygen).
5. Metals [metals given after the enzyme]
   Glutathione peroxidase [selenium], L-Ascorbate oxidase [Copper], Superoxide dismutase [copper, zinc].

The potential analytes are denoted with italics. The cofactors listed here may be replaced with a number of fluorescent analogs that report the activity of the enzyme by their fluorescence or absorption properties. For example, NADH may be replaced by substituted benzoquinones, which are highly colored molecules in the oxidized form and fluoresce in the visible part of the spectrum. They are also redox active. A range of xanthene dyes or analogs of methylene blue may replace FAD. Xanthene dyes are redox active and highly fluorescent. Heme cofactors may be replaced by porphyrins. Porphyrins are fluorescent, have very high molar absorption coefficients and generate excited triplet states in high yield when photoexcited. They are commonly used to determine oxygen concentrations from the lifetime of the triplet state. Metal ions are not easily replaced with a fluorescent species, however the oxidation state of the metal ion may be determined by electron transfer with dyes bound to other parts of the enzyme. Metal ions are readily oxidized and reduced and the oxidation state may be determined from their reactivity with an exogenous photoexcited dye. The oxidation state of the metal reports the reactivity of the enzyme with the relevant substrate.

Those skilled in the art will recognize that there are specific commercially available molecules useful for detecting the RS listed within this invention. For example, for hydrogen peroxide detection, commercial reagents available from Molecular Probes, Inc. include: Carbioxyl-$H_2$DCFDA, CM-$H_2$DCFDA, Dihydrocalcein AM, Dihydrorhodamine 123, Dihydrorhodamine 6G, $H_2$DCFDA, Lucigenin, Luminol, and RedoxSensor Red CC-1. Reagents, which respond to peroxidase introduction or which undergo fluorescence change when oxidized, are also useful for this detection.

Molecular oxygen can be detected using one of several regimes. However, these techniques use a region of the ultraviolet spectrum that is not practical for living organisms, and this mechanism is described here to note that the method could be used for ex vivo analysis. However, multiple dyes used as reagents can be applied for determination of molecular oxygen as shown in M17 and M18 below:

$$O_2 + h\nu \longrightarrow O + O \text{ and} \quad (M17)$$

$$O_2 + h\nu \longrightarrow O_2^+ + e^- \quad (M18)$$

The free electron is then sensed via reduction-induced-fluorescence (REF) detection. In RIF detection, fluorophores such as fluorescein, rhodamine, and others are reduced from a highly colored fluorescent state to a colorless, nonfluorescent leuco dye state. These dyes are available commercially and their actions are described in various literature sources and in commercial fluorophore and reagent catalogs. See for example, Arch Toxicol 68:582, 1994; Brain Res 635:113, 1994; Chem Res Toxicol 5, 227, 1992.

The hydroxyl radical can be measured using CM-H2DCFFDA, Proxyl fluorescamine, and TEMPO-9-AC. Peroxyl radical detection is performed using BODIPY FL EDA, BODIPY 665/676, $H_2$DCFDA, Carboxyl-$H_2$DCFDA, CM-$H_2$DCFDA, DPPP, Luminol, cis-Parinariuc Acid, RedoxSensor Red CC-1. Singlet oxygen is detected using commercial reagents as trans-1-(2'-methoxyvinyl) pyrene. One skilled in the art of synthetic organic chemistry and photochemistry could synthesize additional molecules with similar structures, which would also respond in a likewise manner.

Glucose Monitoring Using Flavin Adenine Dinucleotide Triplet State ($^3FAD^*$)

One embodiment of this invention describes a method for monitoring blood glucose levels in live tissue, such as skin, solid tissue, tissue fluids, and plasma, using photo-induced electron transfer as described herein. The direct oxidation of glucose in vivo is facilitated by the enzyme glucose oxidase, which catalyses the oxidation of glucose to gluconolactone. Gluconolactone spontaneously hydrolyzes to gluconic acid. The cofactor in this reaction is flavin adenine dinucleotide (FAD) and the reaction involves the reduction of the FAD moiety within the glucose oxidase. FAD is eventually re-oxidized by molecular oxygen with the resultant production of hydrogen peroxide.

The reduction of FAD to $FADH_2$ is a two-electron reduction process. In vivo the kinetics of this reaction are facilitated by the enzyme matrix, which orients the reactants in an optimum conformation. One electron transfer to generate the semi-reduced FAD radical and the semi-oxidized glucose radical may be induced by the absorption of a photon. Electron transfer then proceeds from the first excited singlet state or, more likely from the longer-lived first excited triplet state. FAD or another specific photo-oxidant may be used to generate this reaction The reaction scheme as written for FAD may be summarized as shown in M19;

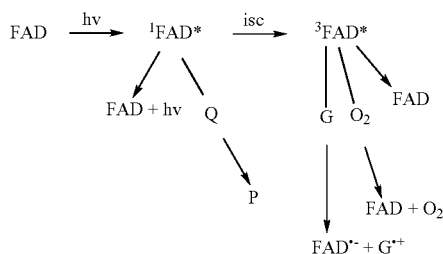

FAD absorbs a quantum of light, represented by hv to form the first excited singlet state, designated as $^1FAD^*$. The most likely fate of this species is decay to the ground state with concomitant fluorescence emission. The singlet state may also react with some quencher, Q, which may be molecular oxygen, glucose or some other reactive species. The fraction of species that decay by this route is relatively small since the intrinsic lifetime of this species is short (i.e., nanoseconds). Approximately thirty percent of $^1FAD^*$ may also form the triplet state, designated as $^3FAD^*$. This $^3FAD^*$ species has an intrinsic lifetime of about 30 µs and may decay in a radiationless transition to the ground state. In vivo, $^3FAD^*$ may react with molecular oxygen and glucose. The reaction of the glucose with the triplet-excited state of FAD may be monitored kinetically by a reduction in the lifetime of the triplet state and under steady state conditions by a decrease in the triplet absorption.

For measurement of glucose, the reporter protein is placed in the keratinocyte layer at 30 µm to 50 µm and up to 175 µm in the pits of the papillae. The reporter protein penetrates into the skin for some period of time to allow activation following passive diffusion kinetics. Once activated, the change in fluorescence or absorption response of the skin cells to changes in inter- and intra-cellular glucose is monitored directly using an optical reader. Chemicals such as salicylic acid can be used to facilitate the penetration of reporter into the skin.

The reporter protein may be introduced into the skin by passive diffusion over 24-48 hours, more preferably within 2-6 hours, and most preferably within about 30 seconds to 5 minutes. An active mechanism utilizing skin permeation, electroporation, or ultrasonic poration (see for example Sontra Medical Corporation, Cambridge, Mass.) is another procedure for introducing reporter protein into the skin. Devices useful for this application sense glucose directly in the interstitial fluid surrounding the skin cells by removing fluid or gaining access to fluid for analysis. This present invention can be used for introducing a small quantity of low concentration reporter protein solution into the skin for direct reading of the reporter protein as an indication of both skin and inferred blood glucose levels.

Instrumentation Required for Reporter Monitoring

The instrumentation required to detect changes in reporter signal may consist of simple light emitting diode sources combined with low-cost solid-state detectors. The mechanism of signal extraction relating to a biochemical or physiological process is derived from the elucidation and measurement of key metabolic pathways. The reporters are excited, and the remitted energy detected over the wavelength region of 190 nm to 850 nm (See FIG. 38). The three mechanisms of measurement for metabolites or precursors using the reporters of the invention include (1) using reporters to increase the signal-to-noise of native autofluorescence signals indicative of human reductive metabolism [$FADH_2$, NADH, and NAD(P)H], (2) using reporters for selection and enhancement of specific metabolite and precursor signals in tissue that are indicative of metabolic state and allow determination of changes in metabolism [$Ca^{2+}$, lactate, oxygen], and (3) using reporters to directly measure the presence of intracellular or extracellular molecular metabolites [protein-FL, and protein-$^3FAD^*$].

All three mechanisms of signal identification and enhancement allow utilization of low-cost, hand held spectrophotometric equipment (e.g., LED excitation and diode detectors) that is simple in design and does not require advanced or complicated computational algorithms. Such equipment is not harmful to subjects and requires just an additional disposable component (other than a calibration strip) to prepare the subject for metabolite monitoring. A measurement device approximately the size of a personal cell phone having quality features, such as those which allow the user to determine whether a specific measurement is valid, or whether a repeat measurement is required, can be used. Such a hand-held, battery powered device is intended to be used either occasionally, or on a continuous, real-time monitoring basis for subjects requiring serious health management regimes. A single calibration allows continuous monitoring for up to several hours. A calibration technology that utilizes a calibration strip, which mimics the optical response of the subject and allows freedom from continuous correction using primary analysis devices, can be used. Other calibration technologies contemplated by the invention will be readily discerned by those skilled in the art.

As an example, to use the device, the subject or physician prepares the area to be measured using the enhancement technology, which is painless and requires a patch (similar in appearance to a Band-Aid®), paint, or spray to be applied to the targeted tissue area. This treatment conditions the tissue area for from a few minutes up to 30 days, depending upon the SMMR properties selected and the depth at which it has been deposited in the subject tissue. The device is then calibrated using a calibration strip and is ready to make measurements for up to 2 hours or more, without requiring additional calibration. The subject or physician examines the conditioned area with the sensor and makes a measurement. Typically, the measurement takes less than about 5 seconds, and the sensor provides the appropriate metabolite concentration or reports that a repeat measurement is required.

In another embodiment, if the photophysics of fluorescent dyes are considered, the fluorescence changes associated with the SMMR and the analyte may also be monitored using fluorescence lifetime technology. One preferred embodiment for such a hand held device capable of measuring lifetime changes is to use a phase and modulation spectrometer, which is a device constructed from a radio frequency modulated light emitting diode and a miniature photomultiplier or photodiode, whose signal is amplified by a phase sensitive amplifier. Such devices have been well characterized in the literature and are commercially available in a variety of forms. Manufacturers of such devices include: Photon Technology International, Inc., 1009 Lenox Drive, Lawrenceville, N.J. 08648; PicoQuant GmbH, Rudower Chaussee 29 (IGZ) 12489 Berlin, Germany; Tecan Systems Inc., 2450 Zanker Road, San Jose, Calif. 95131; Thermo Oriel, 150 Long Beach Blvd., Stratford, Conn. 06615. These devices measure both the degree of modulation of the fluorophore and the phase shift of the emission relative to the excitation light, and these two parameters are then related to the lifetime of the dye. Determination of these parameters at a number of frequencies increases the accuracy of the device.

The instrumentation suitable for monitoring glucose via $^3$FAD* determination includes a device that is capable of monitoring transient absorption changes induced by an excitation source. Two examples of such instrumentation are described here.

First, an excitation wavelength is chosen to match an absorption band of the electron acceptor. For FAD this wavelength is either 380 nm or 450 nm. It is also an option to use both wavelengths. The excitation source is modulated at a frequency that is different from any sources of electrical or optical interference. Any harmonic of 60 Hz in the United States would not be used because this is the frequency of the AC electric supply. The triplet state absorption is monitored from its absorption at 650 nm. A suitable 650 nm source (e.g., a laser diode) irradiates the sample volume irradiated by the excitation source and the light backscattered from the sample is detected with a suitable detector (e.g., photodiode). Triplet state generation results in a fraction of the 650 nm light being absorbed, and provided the modulation frequency is sufficiently short compared to the lifetime of the triplet state (typically 30 µs in oxygen free solution) then the backscattered light will be modulated at the same frequency. The signal seen by the detector appears as a modulated signal superimposed on a constant background. AC coupling of this signal to a lock-in amplifier allows rejection of interfering light sources. In the presence of glucose, the triplet state reacts with the electron acceptor (FAD) and the triplet state absorption is reduced. The amount of FAD in the skin is quantified by a ground state absorption measurement at the excitation wavelength.

Second, an instrument that operates in the time domain may also quantify the triplet state. The apparatus is similar to that described above, with some important differences. The excitation source is intensity modulated. If the frequency of this modulation is chosen so the lifetime of the triplet state is relatively long compared to one cycle of the excitation source oscillation then a phase shift is introduced between the excitation and the detected modulated monitoring beam. The magnitude of the phase shift is given by the expression shown in M20:

$$\tan \phi = \omega \tau \quad (M20)$$

where φ is the phase shift, ω is the circular modulation frequency and τ is the lifetime of the transient species. The phase shift as a function of transient lifetime at a modulation frequency of 20 kHz is shown in FIG. 39.

Figure 39:
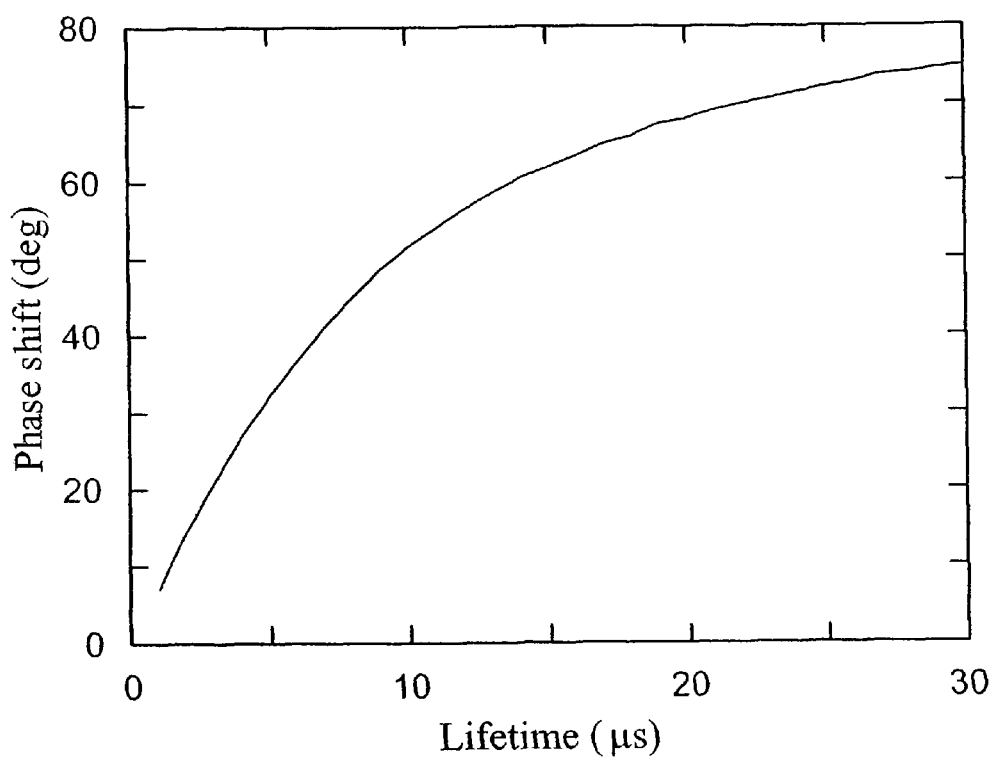
FIG. 39 is a graph showing phase shift as a function of transient lifetime at a modulation frequency of 20 kHz using an instrument that operates in the time domain for quantifying the triplet state.

As shown in FIG. 39, at the designated frequency, the phase shift is most sensitive to changes of lifetime in the 2-10 µs timescale. The monitoring source is a laser diode or LED operating at a wavelength where the electron acceptor triplet state absorbs. The detector is a photodetector, AC-coupled to a lock-in amplifier that returns the magnitude and the phase shift of the signal. The phase shift is related to the lifetime of the acceptor by the expression given above and the lifetime is related to the glucose concentration by the expression in M21:

$$\frac{1}{\tau} = k_d + k_{ox}[O_2] + k_q[G] \quad (M21)$$

where $k_d$ is rate constant for decay by all means other than reaction with oxygen or reaction with glucose, $k_{ox}$ is the rate constant for reaction with oxygen, $[O_2]$ is the oxygen concentration, $k_q$ is the rate constant for reaction with glucose and [G] is the glucose concentration.

The specificity of the instrumentation used for the measurement of glucose concentration is brought about by attaching the electron acceptor (SubMol) to a protein that has a high affinity for glucose. One example of such a protein is glucose oxidase, which already contains the electron acceptor FAD. FAD may be exchanged for other xanthene dyes that have similar size and charge. For specific determination of glucose concentration, selectivity to glucose is improved by linking the electron acceptor to a glucose specific binding protein such as glucose oxidase Calibration of Instrumentation Using Solutions or Strips with Known Metabolite Concentrations One advantage of the present invention is the use of small reagent strips for calibrating the instrumentation required for measuring metabolites (i.e., glucose). The reagent strips are polymer strips with wicking capacity that contain an exact molar concentration of SMMR and metabolite to elicit a specific optical response corresponding to the known metabolite (i.e., glucose) levels for human tissue, tissue fluid, and blood. This technique allows precise optical calibration of metabolite measuring instruments from 0 to 2000 mg/dL in fluids (i.e., approximately 0 to 100 mM for molecules of approximately 350 to 400 daltons); or from 0 to 10 percent by weight or volume of metabolite comprising the range found in human tissue. This technique allows precise optical calibration of glucose measuring instruments from 0 to 650 mg/dL (i.e., approximately 0 to 35 mM) glucose comprising the range of glucose found in human tissue.

Instruments may also be designed to image specific tissue areas where an enhanced signal for metabolites and precursors could allow easy tissue discrimination for damages, circulation poor, necrotic or cancerous tissue versus normal. This tissue having enhanced signal content can be used for physiological studies related to genome, pharmacogenomic, and proteomic studies where genetic code is related to metabolic factors.

To calibrate an instrument, the calibration strip is activated by mixing a known concentration of metabolite into a known concentration of reporter protein. The resultant optical response is used to set the reported metabolite measurement or reading levels on the measuring instrument. This calibration procedure can be conducted for any level of metabolite and is most often completed for two levels to bracket the normal concentration levels. Calibration strips can be made at any metabolite level, however it is preferred that metabolite concentrations of from 0 to 150 percent of the highest expected or theoretical levels be used for calibration, most preferably from 50 to 150 percent of expected levels be used for calibration.

For example, for glucose, it is preferred that glucose concentrations of from about 0 mg/dL to about 500 mg/dL be used for calibration, and most preferred from about 50 mg/dL to about 350 mg/dL be used for calibration. The combined SMMR and detection system can also be used for qualitative analysis of metabolites wherein the purpose of the technique is to identify the presence of a metabolite or precursor (analyte) or to discriminate tissues having high and low levels of a metabolite or precursor, rather than to quantify it. These methods and compositions are useful for identifying the condition of tissue metabolic health during injury, surgery, or cancer detection.

The invention will be further described in the following examples, which do not limit the scope of the invention described in the claims.

Example 1

Relating Fluorescence of Mitochondrial Membrane Probes to D-Glucose Concentration Described herein is a technique for establishing the dose-response relationship for tracking skin and blood glucose concentrations using mitochondrial membrane potential. The SMMR used in this embodiment have the demonstrated property of being mitochondrial-specific vital stains that respond in a direct relationship to the rate of glycolysis, which is directly related to intracellular glucose concentration. The fluorescence response of one specific embodiment of this invention uses SMMR exhibiting an excitation wavelength of from 290 to 790 nm, more preferably 400 to 550 nm, and most preferably from 440 to 490 nm, i.e., the wavelengths used to excite a fluorescence response of the SMMR. The fluorescence is monitored at above 480 nm, preferably above 490 nm and most preferably at 501 nm. The upper range for monitoring is at or below 790 nm. Excitation and emission wavelengths are selected to minimize absorption and fluorescence by endogenous chromophores and fluorophores.

Figure 23:
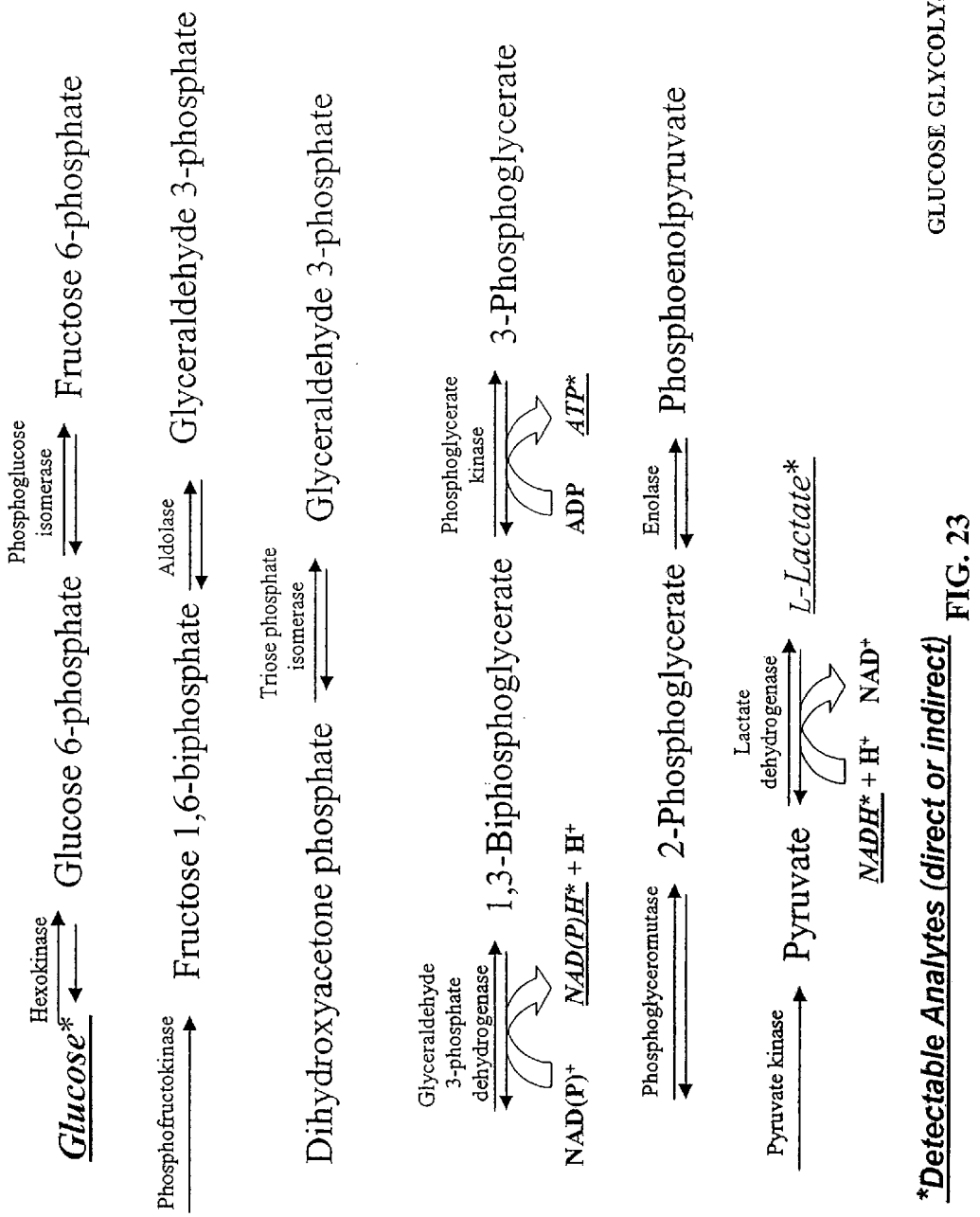
FIG. 23 is a schematic of glucose metabolism showing the specific analytes where glucose measurements are made for the invention, shown as bold, underlined and italicized*. SMMR are used by measuring glucose directly, or by measuring metabolites as indirect indicators of the quantity of glucose entering the cellular glycolytic pathway. Such metabolites are described in detail for the invention and examples are given here as: reducing equivalents molecules (e.g., NAD(P)H, NADH, FAD, $FADH_2$); changes in ATP-driven processes (e.g., cation pumping, transport at membranes, membrane reduction-oxidation electric potential, and pH gradient); and stoichiometric products of glucose utilization in glycolysis (e.g., lactate, hydrogen ion, pH, and pyruvate)

Mitochondrial activity as monitored by oxidative phosphorylation is directly correlated to the number of reducing equivalents derived from NADH, which is generated by aerobic glycolysis or from the conversion of pyruvate to $CO_2$ within the mitochondrial organelles. For aerobic metabolism the number of reducing equivalents is directly and quantitatively (i.e., stoichiometrically) equal to ten times the number of glucose molecules entering the metabolizing cell. The glucose glycolysis pathway is depicted in FIG. 23.

For anaerobic glycolysis, the metabolism of glucose to pyruvate generates two NADH molecules in the cytoplasm of the cell per glucose molecule. NADH is available to the mitochondria by a NADH shuttle system in the mitochondrial membrane. The stoichiometry of this process is such that for every glucose molecule metabolized, two pyruvate molecules are generated. The conversion of pyruvate to acetyl CoA and subsequently to carbon dioxide in the Krebs citric acid cycle is accompanied by the generation of an additional four NADH molecules per pyruvate metabolized. Therefore, the overall yield of NADH per glucose metabolized is ten molecules. The final product of glucose metabolism is carbon dioxide and water.

Under conditions where the most important metabolic substrate is glucose to drive glycolysis, as occurs in the skin, the fluorescence response is linear and in direct proportion to the intracellular glucose concentration. Once the SIy is introduced to the appropriate cell layers (specifically live epidermal cells (keratinocytes) directly above the basal layer (stratum basale)), the SMMR enters the keratinocyte cell membrane and accumulates in the cell mitochondria. When the SMMR is in place for living cells, the fluorescence response may be fully sufficient for in vivo noninvasive determination of the rate of oxidative phosphorylation (i.e., the Kreb's cycle) for living human epidermal cells.

The fluorescence response of these dyes is then related to blood glucose level by the relationships shown in equations 1 and 2. The action of any SMMR or other dye meeting the requirements outlined above include those molecules that are mitochondrion-selective vital SMMRs, which act to indicate the NAD(P)H activity within the mitochondria and, in some cases, the cytosol. The dyes, when used singly or in combination, have an affinity for the mitochondria and accumulate within this organelle in a quantity that is directly proportional to the living cell membrane potential. Changes in membrane potential are reflected in changes in dye levels, thus providing real time monitoring of metabolic state. In other preferred embodiments, all such dyes useful for this invention are non-toxic, non-carcinogenic, non-teratogenic, and do not deleteriously affect the skin when exposed to ultraviolet light or natural sunlight. In preferred embodiments, such dyes included in the present invention are highly fluorescent, are evenly dispersible in the cell and interstitial cell fluid, cannot aggregate or agglomerate, and do not exhibit binding-dependent fluorescent efficiency and quantum yields. In most embodiments, these dyes do not inhibit or restrict normal cell metabolism nor adversely affect cell viability or health in the concentrations and manner used.

Indirect measurement of blood glucose concentration is made as follows. A two-dye measurement regime is provided wherein a non redox indicating dye, which exhibits stable fluorescence with a change in glucose or other metabolites (i.e., the marker dye); and a dye that exhibits direct changes in fluorescence intensity with a change in glucose (i.e., the reporter dye) are measured individually. Optimized dyes are safe, relatively permanent, and non-absorbing into the dermal tissue. The individual dye fluorescence intensity measurements are made using an ultraviolet or visible light emitting diode (LED) or laser diode for an excitation source. The emission detector (i.e., the sensor) collects the light from the emission of the dye signal within the skin. In most embodiments, the sensor device also calculates the ratio of reporter dye fluorescent (following a predetermined lag time as lagt) to the marker dye fluorescence (following the same lag period lagt). A linear univariate computational formula for calibrating such an analyzer for blood glucose is given in equation (1) as:

$$[Glucose_{Blood}] = k_1 \times \frac{\text{Reporter } Fluorescence_{lagt}}{\text{Marker } Fluorescence_{lagt}} + k_o \quad (1)$$

where $k_1$ is the regression coefficient (slope for the line) describing a change in fluorescence for the Reporter to Marker ratio versus glucose concentration in the blood, and $k_0$ is the calibration line intercept. Additionally, a change in glucose concentration over a time interval from $T_1$ to $T_2$ involves the relationship given in equation (2) as:

$$\Delta[Glucose_{Blood}] = k_1 \times \frac{\text{Reporter } Fluorescence_{tagt}(T_2 - T_1)}{\text{Marker } Fluorescence_{tagt}(T_2 - T1)} + k_o \quad (2)$$

where $\Delta[Glucose_{Blood}]$ represents the change in blood glucose concentration and the terms ($T_2$–$T_1$) represent the change in reporter or marker dye fluorescence over the time interval.

The dyes described within this invention may also exhibit an exponential, logarithmic, power, or other non-linear relationship between fluorescence intensity and glucose concentration such that the computational formula for calibrating such an analyzer for blood glucose using an exponential relationship is given in equation (3) as:

$$[Glucose_{blood}] = k_0 e^{k_1 R} \quad (3)$$

where R is the ratio of Reporter Fluorescence$_{lagt}$ to Marker Fluorescence$_{lagt}$.

The computational formula for calibrating such an analyzer for blood glucose using a logarithmic relationship is given in equation (4) as:

$$[Glucose_{blood}] = k_0 + k_1 \ln R \quad (4)$$

where R is the ratio of Reporter Fluorescence$_{lagt}$ to Marker Fluorescence$_{lagt}$.

The computational formula for calibrating such an analyzer for blood glucose using a power relationship is given in equation (5) as:

$$[Glucose_{blood}] = k_0 x^{k_1} \quad (5)$$

where R is the ratio of Reporter Fluorescence$_{lagt}$ to Marker Fluorescence$_{lagt}$.

R can represent the intensity at either a measure wavelength referenced to a baseline wavelength, or as described above as the ratio of Reporter Fluorescence$_{lagt}$ to Marker Fluorescence$_{lagt}$.

Specific methods and compositions of the invention relate to the measurement of glucose using the mitochondrial membrane potential as the metabolic marker. However, as described in Scheme 1 (FIG. 17A), other pathways may also be used to make this measurement and/or to give additional or validation information about the measurement. As noted above, the invention also provides compositions and methods for monitoring and calibrating concentrations of metabolites and small molecules other than glucose.

Example 2

Relating Fluorescence of Energy Transfer to a Reporter Dye to D-Glucose Concentration SMMRs can also be used to report the metabolic state of cells, by using such dyes to monitor NAD(P)H concentration. NAD(P)H can be excited at wavelengths of 340 to 360 nm. Over this wavelength range, the molar absorption coefficient of SMMRs such as Rh123 is low (Rh123 $\in$ <500 L·M$^{-1}$ cm$^{-1}$ from 345 nm to 425 nm compared with 6.3×10$^3$ L·M$^{-1}$ cm$^{-1}$ for NADH. (NADH and NAD(P)H are indistinguishable by their absorption or emission spectra.) Excitation at 350 nm of tissue that has been incubated with Rh123 shows a distinct fluorescence signal at 530 nm. This fluorescence arises because of collisional energy transfer from NAD(P)H to the Rh123. Under conditions where the energy transfer is efficient this process leads to an enhancement of the sensitivity with which NAD(P)H can be detected, shown in equation (6) as:

$$NAD(P)H^* + Rh\text{-}123 \xrightarrow{\text{energy transfer}} Rh\text{-}123^* + NAD(P)H \quad (6)$$

The excited state of Rh123 (Rh-123*) relaxes to the ground state by fluorescence with almost unit efficiency. As a result, the sensitivity of the fluorescence technique to monitor NAD(P)H is increased by at least an order of magnitude or more over autofluorescence. One skilled in the art of photochemistry can easily identify similar conjugated molecules to be used for collisional energy transfer reporting for reducing equivalent molecules, including predominantly NAD(P)H and FADH.

Example 3

Relating Fluorescence of Membrane Localizing Reporter Dyes to D-Glucose Concentration Membrane localizing dyes are used to detect activity of membrane bound proteins. Dyes such as diphenylhexatriene have been used in the past to monitor membrane fluidity. However many dyes may be used to monitor membrane activity by energy transfer mechanisms. Dyes that are useful in this role include molecules that have lower singlet energy levels than amino acid residues such as tryptophan, that is, they absorb light at longer wavelengths than 320 nm. Suitable dyes include, but are not limited to xanthenes, cyanines as well as diphenyl hexatriene and its derivatives. The efficiency of energy transfer is determined by the separation of the donor and acceptor pair and is given by the expression in equation (7):

$$E = \frac{R_o^6}{R_o^6 + r^6} \quad (7)$$

where E is the efficiency, $R_o$ is the Förster radius and r is the donor acceptor separation. The Förster radius is defined as the donor acceptor separation that gives an energy transfer efficiency of 50% and is dependent on the donor and acceptor used. This mechanism is particularly useful for proteins that physically move during activity such as glucose transporter (GluT) proteins. The distance between excited state amino acid residues and an acceptor molecule, usually located in the membrane, will change as the protein carries out its function and hence the efficiency with which the acceptor fluoresces will vary with the activity of the protein. GluT undergoes conformational changes as it transports glucose across the membrane. Excitation of tryptophan residues in a GluT molecule leads to energy transfer to the membrane bound acceptor and the overall fluorescence is then dependent on the concentration of glucose transported across the membrane.

Example 4

Relating Fluorescence of pH Indicating Reporter Dyes to D-Glucose Concentration

Determination of the cytosolic intracellular pH relates the ratio of the cytosolic NAD/NADH ratio to the pyruvate/lactate ratio by the expression as can be derived from textbook information such as that provided by L. Stryer, *Biochemistry*, W.H. Freeman and Co., New York, 1988 (3$^{rd}$ Ed.), pp. 363-364, Chapter 18. An example calculation of intracellular pH is given in equation (8):

$$\frac{[NAD]_{cyt}}{[NADH]_{cyt}} \propto \frac{[\text{pyruvate}] \times 10^{-\text{pH}}}{[\text{lactate}]} \quad (8)$$

The measurement of pH as a direct indicator of lactate/H$^+$ concentration in skin yields direct information on skin and blood glucose concentrations. The parameter of pH as $-\log_{10}$ [H$^+$] can be measured using calibrated pH sensitive dyes or with a variety of known microprobe electrodes specifically designed for pH determination. One embodiment involves a series of techniques that allow the placement of a specialized "tattoo", or more precisely the "active viewing window" comprised of one of a choice of specific pH indicating SMMRs, into the epidermis using methods including, but not limited to, electroporation, direct application by painting with specific transporter solvent mixtures, tattooing methodologies, laser poration, sonic poration, iontophoresis, mechanical-poration, solvent transport, wicking, microneedle, pressurized delivery or by an equivalent active or passive application technique.

In another embodiment of the SMMR application techniques a small disposable polymer patch containing an SMMR dispersed into a transfer gel is applied to the skin using a pre-specified protocol.

Another embodiment is to have a small dispenser with a specialized tip for placing a measured dose of the SMMR, with or without a solvent mixture, onto the skin. The molecular tag or SMMR is allowed to penetrate the skin for some period of time to allow activation (from 1 minute to 3 hours, depending upon the mixture used). Once activated, the response of the skin cells to glucose is monitored directly using an optical reader on the SMMR-treated viewing window. The optical reader calculates the skin fluorescence response to glucose, applies first principles mathematical models to the response, and provides a determination of the blood glucose levels.

These concepts and results are demonstrated in FIGS. 1-9, especially in FIGS. 3-5, 8, 9. A quality value may be simultaneously calculated in the optical reader/sensor telling the user the quality of the glucose value reported. Based on this quality value, the user may be instructed to make one or more additional measurements until the quality value is indicative of an accurate result.

These features provide a technique for establishing the dose-response relationship for tracking glucose. See, e.g., FIGS. 3, 8, 9. Specific SMMRs to be used have demonstrated properties of being pH:lactate/H$^+$-indicating SMMRs that respond in a direct linear, exponential, or sigmoid relationship to intracellular glucose concentration. An increase in intracellular glucose causes a direct increase in intracellular lactate/H$^+$ via glycolysis, thereby decreasing the intracellular pH in real-time by a stoichiometric inverse proportionality, relative to the increase in glucose concentration. The visible light response of these SMMRs is such that a diffuse reflection or fluorescent emission spectrum or signal obtained after excitation at one or more optimum wavelength(s), e.g., between 300 nm and 750 nm and more preferably at least 450 nm, is directly correlated to the quantity of glucose available to fuel metabolic (glycolytic) activity and is unaffected by cellular metabolic rate. Therefore the absorption/diffuse reflection or fluorescence spectrum measured is in direct proportion to the intracellular glucose concentration. The reaction velocity assumption set for quantitative analysis of metabolites, including pH, is described above.

When the SMMR is comprised of a mixture including a fluorescent indicator dye, then fluorescence spectroscopy may be used to determine the pH/lactate/H$^+$ in the microenvironment of the cell. Once the tattoo or SMMR mark is produced, these methods and compositions can be used for in vivo noninvasive determination of the rate of glucose utilization, whether occurring by glycolysis, oxidative phosphorylation (i.e., the Kreb's cycle), or a combination of these metabolic processes. In the case of mammalian or human keratinocytes, anaerobic glycolysis is the pathway defined using this technique. The determination of glucose is accurate for living mammal or human epidermal cells as long as the SIR remains within the area of the stratum spinosum. SMMRs meeting the requirements for this embodiment include but are not limited to phenolphthalein, which is useful for absorption measurements of pH. Fluorescent SMMRs include but are not limited to molecules that are xanthene dyes, especially 2',7'-bis-(2-carboxyethyl)-5-(and -6)-carboxyfluorescein, (BCECF), and other standard pH indicating fluorescent dyes available from, e.g., Aldrich, Sigma, Molecular Probes, and other manufacturers. Alternatively, as the structures are known, those skilled in the art may be able to synthesize these materials.

Other SMMRs meeting these requirements include BCECF, which can be used at 439 nm and 490 nm excitation. pH is calculated from the emission detected at 520 nm. Measurements may also be made of the lifetime of BCECF, and such measurements have been made in the stratum corneum. See, e.g., Hanson, K. M., et al., Two-photon fluorescence lifetime imaging of the skin stratum corneum pH gradient. *Biophysical Journal*, Vol. 83, pp. 1682-1690. An alternative molecule is benzenedicarboxylic acid, 2(or 4)-[10-(dimethylamino)-3-oxo-3H-benzo[c]xanthene-7-yl]-(SNARF-1) using 514 nm excitation and fluorescence detection at 640 nm and 587 nm, respectively. The fluorescence ratio at these emission wavelengths allows the determination of the ratio of the protonated and unprotonated forms of the dye. This ratio allows the determination of the pH of the dye environment using the Henderson-Hasselbalch equation (9).

$$\text{pH} = pKa - \log\frac{HA}{A^-} \quad (9)$$

As an illustrative example, for BCECF this relationship becomes equation (10):

$$\text{pH} = pK_a + \log\left(\frac{(F_{490}/F_{439}) - (F_{490}^a/F_{439}^a)}{(F_{490}^b/F_{439}^b) - (F_{490}/F_{439})}\right) \quad (10)$$

In this expression the fluorescence is monitored at a wavelength of 535 nm, the terms $F_{490}$ and $F_{439}$ refer to the fluorescence intensity monitored at excitation wavelengths of 490 nm and 439 nm respectively and the terms with superscripts a and b represent the limiting values of the fluorescence ratio in acid (a) and base (b) respectively.

Use of the dye to measure absolute values of pH requires a small correction of the fluorescence ratio since the two fluorescence emission bands are not completely separated.

A difference comparison of both intracellular and extracellular pH measurements allows measurements to be made of lactate synthesis, transport and diffusion out of the interstitial fluid. The difference between intracellular and extracellular pH is indicative of the hydrogen ion produced within the cell (due to glycolysis) and those hydrogen ions that are produced systemically.

Estimation of the Effect of Glucose Metabolism on Changes in Intracellular pH

Numerous prior studies measured intracellular pH in a variety of organisms and cell types. See, e.g., Roos, A. and Boron, W. F. (1981) Intracellular pH. *Physiological Reviews*, vol. 61, pp. 297-434. Of interest are experiments that examine the effect of weak acids and bases on the pH of cell extracts and homogenates. Using a simple equation (11) from Michaelis to describe the buffering capacity of a solution, the physicochemical buffering of these samples can be expressed as "intracellular buffering power" as follows:

$$\beta = \frac{d(A \text{ or } B)}{d\text{pH}} \quad (11)$$

β: total buffering power of intracellular fluid
A: amount of added acid
B: amount of added base
See, e.g., Roos and Boron, 1981, pp. 389-400.

The intracellular buffering power of different tissues and cell types are summarized in Roos and Boron (1981), supra, Table 13, at p. 399. Table 1 (below) uses equation (11) and the intracellular buffering power of rat tissues to calculate the potential effect of 5 mM glucose (undergoing glycolysis) on intracellular pH. These calculations are based on studies reporting that a net of two protons (two lactate) are produced for every molecule of glucose that is metabolized. See e.g., Busa, W. B. and Nuccitelli, R. (1984) *Am. J. Physiol.*, vol. 246, R409-R438; and Robergs, R. (2001), *Professionalization of Exercise Physiology-Online*. vol. 4, no. 11. Thus, by deriving this information for a specific cell type and for the conditions of an individual subject, the glucose available to a cell for glycolysis can be calculated from the measured pH.

TABLE 1

| Tissue | Buffering Power | pH change (5 mM glucose or 10 mM H⁺) |
|---|---|---|
| Rat Brain (whole) | 18.5 | −0.54 |
| Rat Diaphragm Muscle | 67 | −0.15 |
| Rat Skeletal Muscle | 66–68 | −0.15 to −0.16 |
| Rat Cardiac Muscle | 51 | −0.19 |
| Rat Ventricular Muscle | 77 | −0.13 |

Measurement Protocol

The rationale for making measurements of D-glucose and other simple sugars using pH (i.e., lactate/H⁺) sensitive intracellular dyes is described. The specific rationale is based upon the concept that glycolytic mechanisms may be monitored via metabolite concentration to give an estimation of the total D-glucose available to the cell (Scheme 1, FIG. 17A). In this embodiment of the invention, the fluorescence of a pH-sensitive dye is used to determine blood glucose concentrations. This measurement is possible because for every glucose molecule undergoing glycolysis, two lactate/H⁺ molecules result. Thus, depending upon the buffering capacity for any specialized cell types, the pH is indicative of the quantity of glucose available. During glycolysis, the glucose is immediately converted to lactate.

In most embodiments, two steps are required for the glucose measurement. The measurements to be made are the intensity of fluorescence at about 580 nm and 640 nm with 532 nm excitation. The bandwidth of these measurements is typically 10 nm wide. Intracellular pH is monitored using an intracellular dye that is equivalent or superior in efficacy to SNARF 5 AM; i.e., extracellular pH is monitored using an extracellular dye equivalent or superior in efficacy to SNARF 5 (SNARF®-5F 5-(and -6)-carboxylic acid). The dyes are typically applied in two different places. A third spot is applied using an intracellular dye equivalent or superior in efficacy to SNARF 5 AM to be used to determine the spectra of the acidic and basic forms of the dye. All dyes are applied in a 10 μL volume having a final concentration of 200 μM.

The protocol used for application of the dye requires that a skin temperature between 30° C. and 37° C. be maintained. The area of skin to be measured is rinsed with approximately 1 mL of distilled water and wiped dry with an uncoated tissue or Kimwipe. It is preferable to wipe the area clean with a clinical alcohol wipe. Once a clean area of skin has been prepared, 10 μL of dye is applied to the skin with an automatic dispenser or pipette. The dye spots are protected from room light and all manipulations are carried out under dimmed room light. After one hour, any dye that remains on the surface of the skin is blotted off with a Kimwipe. The uptake of dye was monitored using a two-photon microscope and by measuring spectra after the dye is applied. It was determined by observation that measurement should begin three hours following application of the SMMR.

To test the efficacy of the sensor measurement during the measurement period, sensor readings were recorded every time a blood sample was withdrawn for reference measurements. The test measurement was designed so that the autofluorescence, and the fluorescence from SMMRs located in the intra and extracellular spaces can be acquired ideally at the same time. The only way to do this at present is to move the sensor to different sites between measurements. However, other methods may be used as they become available to provide equivalent information.

Reference blood samples drawn were analyzed for blood glucose, lactate and hematocrit. Spectra were acquired from the skin, to obtain autofluorescence, from the spot where an extracellular dye equivalent or superior in efficacy to SNARF 5 was applied to obtain the extracellular pH, and from the spot where an intracellular dye equivalent or superior in efficacy to SNARF 5 AM form (available from Molecular Probes, Inc. Eugene, Oreg.) was applied to obtain the intracellular pH. Finally, acid and base were applied to the control spot to obtain the spectra from the fully protonated and fully deprotonated dyes.

For normal prandial studies, this measurement protocol lead to a smaller range of glucose values than those obtained using clamp studies. Typically, fasted mammals have a blood glucose concentration of anywhere between 50 mg/dL to 100 mg/dL, whereas fed mammals have a glucose concentration range of 100 mg/dL to 150 mg/dL.

The data were analyzed according to equation (12):

$$\text{pH} = pK_A + \log\left[\frac{R - R_B}{R_A - R} \times \frac{F_{B(\lambda 2)}}{F_{A(\lambda 2)}}\right] \quad (12)$$

where R is the ratio of the fluorescence intensity at 580 nm and 640 nm, $R_B$ is the same ratio when the dye has been made alkaline and $R_A$ is when the dye has been acidified. The terms $F_A$ and $F_B$ are the intensity measurements at 640 nm in acid and base respectively.

Equation (12) is a modified version of the Henderson-Hasselback equation that describes the fraction of molecules that are protonated in an acid-base system at a certain pH. The term in parentheses is inversely proportional to the hydrogen ion concentration. The ability to relate glucose concentration to pH is based on the stoichiometry of glycolysis. For every equivalent of glucose that is metabolized, two equivalents of hydrogen ions are generated. pH is simply the negative log of the hydrogen ion concentration.

The fluorescence ratio values were obtained after the intensity of the autofluorescence has been subtracted. Although this expression actually gives the pH value in these measurements, it should be realized that the glucose concentration is only a function of the pH. If the oxidation of glucose results in the formation of hydrogen ions then it is the corrected fluorescence ratio that is important in the determination of glucose concentration. As far as the influence of external pH, it is hypothesized that the changes in intracellular pH are dependent on the difference between intracellular and extracellular pH. The basis for this assumption is that the monocarboxylate transporter is a facilitated diffusion pump. As a result, hydrogen ions can be pumped out if the external pH is high compared to the intracellular pH. It is more difficult to pump hydrogen ions out if the pH is low.

Example 5

Empirical Calibration Scheme—General Case

An empirical correction scheme for obtaining quantitative fluorescence spectra from molecules embedded within the skin of individual human subjects is required due to the unique scattering and absorptive properties of individuals. The effects on fluorescent spectra brought about by these individualistic optical properties include changes in bandshape and relative fluorescence intensity. A general equation (13) for obtaining quantitative fluorescence calibration spectra, which will accommodate for unique tissue matrix effects, is written as:

$$\hat{C}_i = (\mathcal{J} - \mathcal{J}_B) \frac{c_1 - c_2}{(f_1 - \mathcal{J}_B) - (f_2 - \mathcal{J}_B)} \quad (13)$$

where $\hat{C}_i$ is the estimated concentration for a test sample I; $\mathcal{J}$ is the fluorescence response of the test sample I; $\mathcal{J}_B$ is the fluorescence response of the test sample site with solvent treatment only; $f_1$ is the fluorescence response of the sample site at concentration $c_1$ (a concentration higher than the expected concentration of the test sample I); $f_2$ is the fluorescence response of the sample site at concentration $c_2$ (a concentration lower than the expected concentration of the test sample I). See, e.g., Harrison, G. R., Lord, R. C., and Loofbourow, J. R. *Practical Spectroscopy*, Prentice-Hall, Inc., New York, N.Y., 1948, pp. 412-414.

Example 6

Empirical Calibration Scheme—Special Case of Lactate/H+: pH Measurements

Specifically for the case involving quantitative determination of lactate/$H^+$ using intracellular or extracellular pH measurements, one would work with hydrogen ion concentration directly as $[H^+]$. In the case where an indicator dye exhibits a fluorescence response due to a change in $[H^+]$ following the relationship as shown in equation (14):

$$[H^+] = k_a \left( \frac{\frac{f(\lambda_1)}{f(\lambda_2)} - \frac{f_B(\lambda_1)}{f_B(\lambda_2)}}{\frac{f_A(\lambda_1)}{f_A(\lambda_2)} - \frac{f(\lambda_1)}{f(\lambda_2)}} \right) \cdot \left( \frac{f_B(\lambda_1)}{f_A(\lambda_2)} \right) \quad (14)$$

where $f(\lambda_i)$ is the fluorescence measurement at wavelength i and the subscripts A and B represent the respective acidic and basic endpoints using a titrimetric approach. See, e.g., Molecular Probes Product Information Sheet #MP 01270, *SNARF pH Indicators*, Molecular Probes, Eugene, Oreg., Oct. 22, 2002). This relationship, shown in equation (15), holds noting that background correction is applied to each fluorescent signal prior to ratio calculation. If $\lambda_2$ is selected as the isosbestic point, then the relationship below holds. For a dye such as SNARF-1: $\lambda_1$=580 nm, $\lambda_2$=640 nm, and $\lambda_{EX}$=514 nm, $\lambda_{Isosbestic}$=608 nm.

$$[H^+] = k_a \left( \frac{\frac{f(\lambda_1)}{f(\lambda_2)} - \frac{f_B(\lambda_1)}{f_B(\lambda_2)}}{\frac{f_A(\lambda_1)}{f_A(\lambda_2)} - \frac{f(\lambda_1)}{f(\lambda_2)}} \right) \quad (15)$$

Then the corrected equation 13 for measurement of hydrogen ion concentration accounting for matrix effects should be as equation (16):

$$[\hat{H}^+]_i = (\mathcal{J} - \mathcal{J}_B) \frac{[H^+]_1 - [H^+]_2}{(f_1 - \mathcal{J}_B) - (f_2 - \mathcal{J}_B)} \quad (16)$$

where $\lfloor \hat{H}^+ \rfloor_j$ is the estimated concentration for a test sample i; $\mathcal{J}$ is the fluorescence response of the test sample i; $\mathcal{J}_B$ is the fluorescence response of the test sample site with solvent treatment only; $f_1$ is the fluorescence response of the sample site at concentration $\lfloor H^+ \rfloor_1$ (a concentration higher than the expected concentration of the test sample i); $f_2$ is the fluorescence response of the sample site at concentration $\lfloor H^+ \rfloor_2$ (a concentration lower than the expected concentration of the test sample i).

Example 7

Use of External Calibration Standards for General Case

The use of external calibration standards (i.e., standard addition) is essential in providing a bloodless method for calibrating in vivo measurements. In theory, a set of two or more calibration standards comprised of known concentrations of analytes (e.g., glucose) can be externally added to tissue and delivered to the specific analysis target site(s). Such a practice does not rely on a purely theoretical approach dependent on some fixed assumption set. Thus a more broadly applicable method would involve reliance on an empirical measurement approach. Such an approach must be applied across idiosyncratic physiological properties of specific tissue sites including: perfusion rate, interstitial fluid volume, rates of diffusion into and out of the tissue, glucose transport, and the like. Such phenomena can be illustrated generally as in Scheme 4 (FIG. 17D) illustrating fluid issues related to in vivo skin calibration.

As an example, an in vitro experiment using such standard addition can be reviewed. The experiment is to determine the final concentration of a cuvet initially containing a liquid of 100 volume units (Vi) and a concentration of 100 w/v (Ci). In this case, neither the initial volume nor the initial concentration is known. To begin, a known Standard liquid (A1) is added to the cuvet having a volume of 100 volume units (Va1) and a concentration of 0.0 w/v (Ca1). A fluorescence measurement is made of the solution plus Standard A1 and the result recorded as $\Im a1$. The final concentration of the cuvet at this point may be determined using the general equation (17):

$$C_{f_{a1}} = \frac{(C_i \cdot V_i) + (C_{a1} \cdot V_{a1})}{V_i + V_{a1}} = \frac{(100 \cdot 100) + (0.0 \cdot 100)}{100 + 100} = 50\frac{w}{v} \quad (17)$$

A second Standard liquid (A2) is then added to the cuvet having a volume of 100 volume units (Va2) and a concentration of 500 w/v (Ca2). A fluorescence measurement is made of the solution plus Standard A2 and the result recorded as $\Im a2$. Following the addition of Standard A2 the cuvet now contains a concentration calculated using equation (18):

$$C_{f_{a2}} = \frac{(C_i \cdot V_i) + (C_{a2} \cdot V_{a2})}{V_i + V_{a2}} = \frac{(50 \cdot 200) + (500 \cdot 100)}{200 + 100} = 200\frac{w}{v} \quad (18)$$

If a fluorescence method has been developed capable of measuring the concentration of analyte defined as a linear relationship over a concentration range of between 50 and 400 w/v (see Table 2), then equation (19) holds as:

$$\frac{\Im_{a2}}{\Im_{a1}} = \frac{C_{f_{a2}}}{C_{f_{a1}}} \quad (19)$$

Thus a ratio measurement of $\Im a2$ and $\Im a1$ yields a value of 200/50=4.0 and provides sufficient information to compute absolute concentration of the initial fluid as well as the final fluid levels. The examples below consider two examples of the in vivo case.

Example 8

Equivalent volumes of Standards A1 and A2 are added to the tissue as volumes Va1 and Va2; these volumes approximate the current interstitial volume. The concentration of the added Standards A1 and A2 are 0.0 w/v (Ca1) and 300 w/v (Ca2). The interstitial volumes are assumed to remain approximately the same as the liquid from the Standards mix with the interstitial fluid, i.e., after a period, there is a mixing of liquids causing an equilibrium of the analyte levels, but no overall interstitial fluid volume change. The equivalent relationships can be calculated for any set of assumptions. Since in this case the equivalent volume assumption is made then equation (20) holds:

$$C_{f_{ai}} = \frac{(C_i \cdot V_i) + (C_{ai} \cdot V_{ai})}{V_i + V_{ai}} \quad (20)$$

Equation (20) reduces to a simple relationship where the volumes Vi, Va1 and Va2 are equivalent and there is assumed diffusion of the analyte from the Standards to the interstitial fluid equilibrating the concentration given sufficient time. Thus, equation (21) is used:

$$C_{f_{ai}} = \frac{C_i + C_{ai}}{2} \quad (21)$$

This scenario takes into consideration that the addition of the first Standard A1 at 0.0 w/v concentration reduces the concentration; and then the second Standard A2 at 300 w/v concentration is added. As such the following Table 2 holds.

TABLE 2

Application of Standards A1 and A2 as 100 unit volume and 0.0 w/v and 300 w/v concentration.

| Initial Volume (Vi) | Initial Conc. (Ci) | $C_{f_{a1}}$ | $C_{f_{a2}}$ | $\frac{C_{f_{a2}}}{C_{f_{a1}}} = \frac{\Im_{a2}}{\Im_{a1}}$ |
|---|---|---|---|---|
| 100 units | 50 | 25 | 162.5 | 6.5 |
| 100 units | 100 | 50 | 175 | 3.5 |
| 100 units | 150 | 75 | 187.5 | 2.5 |
| 100 units | 200 | 100 | 200 | 2.0 |
| 100 units | 250 | 125 | 212.5 | 1.7 |
| 100 units | 300 | 150 | 225 | 1.5 |
| 100 units | 350 | 175 | 237.5 | 1.36 |
| 100 units | 400 | 200 | 250 | 1.25 |

Example 9

Equivalent volumes of Standards A1 and A2 are added to the tissue as volumes Va1 and Va2; these volumes approximate the current interstitial volume. The concentration of the added Standards A1 and A2 are 0.0 w/v (Ca1) and 400 w/v (Ca2). As in Example 8, the interstitial volumes are assumed to remain approximately the same as the liquid from the Standards mix with the interstitial fluid, i.e., there is a mixing of liquids causing an equilibrium of the analyte levels, but no overall interstitial fluid volume change. Since this assumption is made, then equations 20 and 21 are used.

This scenario takes into consideration that the addition of the first Standard A1 at 0.0 w/v concentration reduces the concentration; and then the second Standard A2 at 400 w/v concentration is added. As such the following Table 3 holds as.

TABLE 3

For the application of Standards A1 and A2 as 100 unit volume and 0.0 w/v and 400 w/v concentration.

| Initial Volume (Vi) | Initial Conc. (Ci) | $C_{f_{a1}}$ | $C_{f_{a2}}$ | $\frac{C_{f_{a2}}}{C_{f_{a1}}} = \frac{\Im_{a2}}{\Im_{a1}}$ |
|---|---|---|---|---|
| 100 units | 50 | 25 | 212.5 | 8.5 |
| 100 units | 100 | 50 | 225 | 4.5 |
| 100 units | 150 | 75 | 237.5 | 3.17 |
| 100 units | 200 | 100 | 250 | 2.5 |
| 100 units | 250 | 125 | 262.5 | 2.1 |
| 100 units | 300 | 150 | 275 | 1.83 |
| 100 units | 350 | 175 | 287.5 | 1.64 |
| 100 units | 400 | 200 | 300 | 1.5 |

Example 10

Screening and Optimizing Organic Dyes for SMMR Activity

In some embodiments of the invention, a dye is added into a tissue with an anticipated SMMR-response activity, and spectra are collected for a set of predetermined excitation and emission wavelengths. The excitation wavelength set selected corresponds to the maximum absorption spectrum of the dye being used. The optimal measurement wavelength for excitation and emission is then determined empirically for each SMMR application such that the selected excitation wavelength results in a combined effect where maximum emission intensity and response is achieved for each metabolite of interest. Metabolites useful for tracking glucose were derived from an understanding of the glycolytic pathway for the cells of interest and an understanding of which dyes may actually behave as SMMRs for quantitative reporting of these metabolites. By selecting the optimum wavelengths for SMMR measurement in an empirical fashion, the precise method for quantitative detection of each metabolite was achieved, thereby yielding maximum analytical selectivity, repeatability, and reproducibility.

Empirical Procedure for the Development of Calibration Protocols

The following procedure can be used to develop the calibration protocol for a blood glucose analysis method combining SMMRs with a low-cost, handheld sensor: (1) the glucose (or another blood or tissue analyte) is measured for the test subject (or series of test subjects) by withdrawing blood from a subject and by analysis via a reference blood glucose measurement (the glucose may be intentionally varied within the test subject for the test evaluation period); (2) the metabolic reporter signal and a marker (or reference) wavelength signal are measured at a time-stamped interval corresponding to the blood glucose reference measurement (this is completed for a series of excitation and emission wavelengths); (3) the ratio of the metabolic reporter and reference or marker wavelengths is calculated for each set of excitation and emission wavelengths; (4) the series of ratio measurements of the reporter/reference is compared to the reference blood glucose measurements; (5) the optimum wavelength sets are derived and the absolute ratios determined that best correspond to specific blood glucose levels, taking into account the lag times and best mathematical model; (6) a small handheld device is provided, preferably where the device has the capability to measure the signal at the optimized specific wavelengths using exact excitation sources and emission detection schemes (with defined intensity and bandshape characteristics); (7) the ratio measurements of the device when coupled with specific SMMRs produces a metabolite profile that is used to directly predict blood glucose concentration using algorithms described herein. Those skilled in the art will recognize that when the metabolic pathways for multiple biosyntheses are defined, that this empirical testing method can be used to screen multiple dyes for their efficacy as SMMRs for a variety of metabolic measurements. Thus, without much knowledge about specific pharma-kinetic activity or dyes, a series of compounds can be screened and optimized for SMMR activity.

Ideally, all dye candidates to be tested for SMMR activity in humans are first screened properly to ensure safety.

Example 11

Factors Affecting the Molecular Structure and Action of Organic Dyes Suitable for Use as SMMRs Molecular Design There are six main characteristics of a dye molecule that determine its efficacy as an SMMR according to the methods and devices of the invention. These include: (1) its affinity and specificity for target cells and cell structures; (2) its binding properties and residence time in skin; (3) its safety to cells and organisms; (4) its speed of delivery; (5) its specificity for the metabolite of interest; and (6) its spectral properties. Properties that control the affinity and specificity for target cells and cell structures for SMMR molecules into skin cells include:

1. The partition coefficient in octanol/water together with the solubility in aqueous solution, which determines how the molecule is distributed between the aqueous and lipid phases in the tissue;
2. The charge, which affects electrostatic interactions of the compound;
3. The vapor pressure at 25° C., which determines the evaporation rate at the skin surface;
4. The molecular size, which controls the diffusion of the material through a porous interface or a viscous liquid.

Factors affecting the functionality of the molecule include the reactivity and reduction potential of the molecule, the pKa and the energy level of the first excited state.

Spectral properties that are important for SMMRs include the absorption spectrum of the chromophore, the fluorescence spectrum and the emission quantum yield. Properties that moderate the absorption characteristics include the degree of conjugation in the molecule, the number of electrons in the conjugated system and the electro-negativities of substituents attached to the molecule. Factors that affect the fluorescence emission spectrum are similar to those that affect the absorption spectrum. The fluorescence quantum yield, which determines the intensity of the fluorescence, is influenced by the flexibility of the molecule and the intramolecular reactivity.

An example of how a xanthene dye may be modified to act as a long wavelength pH sensitive dye for specific action as a lactate/H$^+$ SMMR is described herein. One possible structure is shown in Scheme 3 (FIG. 17C). As shown in FIG. 17C, the xanthene ring is substituted with hetero atoms (A) that extend the conjugation of the molecule across the fused ring system. Electron density in the ring system is increased by the lone pair of electrons on the heteroatom that are partly delocalized into the ring system. Typical groups at these positions would include an amine and an amide, such as rhodamine.

The pKa of the molecule is controlled by the substitution of acidic and basic groups (B) and the nature of the heteroatoms (A). Small changes to the pKa may be made by substitution of electron donating or withdrawing groups to the ring (D). The quantum yield of fluorescence ($\phi_F$) and hence the intensity of the fluorescence is determined by the balance between the rate constants for radiative ($k_r$) and non-radiative ($k_{nr}$) decay as shown in equation (22):

$$\phi_F = \frac{k_r}{(k_r + k_{nr})} \qquad (22)$$

The radiative rate constant is determined by the probability of a transition whereas the non-radiative rate constant is affected by the number of modes of vibration that a molecule has and any intramolecular reactivity that can quench the excited state.

The absorption spectrum of the molecule is determined by the extent of the conjugation as well as substitution on the ring (C). Substitution of both electron withdrawing and electron donating groups in a push-pull type of system extends the overall conjugation of the system and causes a bathochromic shift (to longer wavelengths) of the spectrum. A number of empirical rules have been put forward to predict spectra. The well-known Woodward rules, for example, predict that for a simple conjugated system the addition of a double bond adds about 30 nm to the wavelength maximum.

The polarity of the molecule can be altered, without grossly affecting other properties of the molecule, by substitution of non-conjugated groups to the ring system (E). Many xanthene dyes are synthesized with a substituted phenyl ring at $R_2$. It is by specific modification of this dye and the measurement of its fluorescence signature that allows the dye to function as an SMMR to relate lactate/$H^+$ to D-glucose concentration (as noted in FIGS. 1-17).

Example 12

Use of Glycogen Particle Density

The measurement of glycogen particle numbers indicates a direct proportionality to the amount of glucose in the metabolic pathway of the cell (for an individual metabolic rate). As Scheme 2 (FIG. 17B) illustrates, a measurement of glycogen synthesis provides an indicator of glucose concentration because the only biochemical route to glycogen is directly from glucose. The use of iodine-based SMMRs within the skin can be measured using an optical reader as a direct indicator of glycogen particle concentration in the skin. Skin glycogen concentration can be related to skin glucose levels, which in turn are mathematically related to blood glucose levels. Thus, skin glycogen concentration yields direct information on skin and blood glucose concentrations. The parameter of glycogen particles can be measured using a variety of known techniques. Glycogen particles are known to have a mean particle size diameter of approximately 30 nanometers (nm). Thus, an ideal wavelength for characterizing the presence of these particles in an absorptive-scattering media such as skin would be at 2.5 to 3.5 times the diameter or approximately 75 to 105 nm ultraviolet light. This invention contemplates utilizing such a wavelength to characterize the number of glycogen particles within the skin, as well as utilizing other potential methodologies for measuring the particle density for glycogen include scattering measurements in the 290 nm to 750 nm spectral regions, and includes optical coherent tomography. Mathematical manipulations of the data derived from these techniques can provide correlative information allowing prediction of glycogen particle numbers.

In one specific embodiment, a series of techniques are described in the invention which allow the placement of a specialized tattoo, comprised of at least one of a choice of specific glycogen indicating SMMR, into the epidermis for analysis of mitochondrial membrane potential and pH indicating signals. Measurement of glycogen particles, which preferentially absorb SMMR, is monitored directly using an optical scattering reader. The optical reader calculates the total absorption of the SMMR into the glycogen particles. Once determined, the glycogen content of the skin is empirically related (by first principles mathematical models) to reference skin and blood glucose levels. Simultaneously, a quality value is calculated, which tells the user the quality of the glucose value reported. Based on this quality value, the user may be instructed to make one or more additional measurements until the quality value is indicative of an accurate result.

Once the tattoo or mark is produced, this invention may be fully sufficient for in vivo noninvasive determination of the rate of glucose utilization within living human epidermal cells as long as the SMMR remains within the stratum spinosum. SMMR meeting the requirements for this embodiment are described above, and include, e.g., iodine dissolved in potassium iodide. Iodine forms a blue-black complex with glycogen, the intensity of which is directly related to the number of particles of glycogen present in the tissue. The visible response of these SMMR is then related to blood glucose level by the relationship given in equation (23):

$$[G] \propto \frac{\#glycogen\ particles. \times NAD(P)H}{FAD \times NO \times pH \times O_2} \quad (23)$$

Equation (23) is based on measuring a cell function and normalizing this function for the relative metabolic rate of the tissue. The number of glycogen particles is directly related to the glucose concentration. This relationship will break down when metabolism is high and all the glycogen reserves have been utilized. The concentration of glycogen particles can be obtained from measurements using optical coherent tomography, light scattering, or differential staining of glycogen particles using iodine stains.

Example 13

An Example of a Targeted Pathway

Mathematical Modeling Applications to Glucose Concentration

FIG. 23 is a proportionality-qualitative description of how the glycolytic pathway (e.g., glycolysis) relates to glucose concentration in cellular metabolism. The quantitative description of these pathways is developed dependent upon accurate, selective, and responsive measurement parameters yielding indirect or direct information for glucose concentration. An example of the quantitative treatment for fluorescence changes associated with the activity of glucose oxidase is given in Equation (24).

Several examples of the mathematical models required for fitting the reported glucose to the measured blood glucose for this invention are given in Equations 1-5. The addition of glucose to a solution of glucose oxidase causes an increase in fluorescence after a lag time. The lag period can be related to the concentration of the glucose oxidase, the oxygen concentration and the glucose concentration. Assuming that the rate constant for the reoxidation of the reduced enzyme is significantly greater than the binding and oxidation of glucose, and that the concentration of the free oxidized enzyme is higher than that of other forms before the time at which the fluorescence changes, then the following expression in equation (24) has been derived.

$$t_m - t_0 = \frac{1}{k_1 [GO_x]_0} \ln\left(\frac{[G]_0}{[G]_0 - 2[O_2]_0}\right) \quad (24)$$

where
$t_m$ Time at which the fluorescence changes
$t_0$ Time at which glucose is introduced
$k_1$ Rate constant for the reduction of $GO_X$ by glucose
$[GO_X]_0$ Initial concentration of glucose oxidase
$[G]_0$ Initial concentration of glucose
$2[O_2]_0$ Initial concentration of oxygen
See, e.g., Sierra J. F., Galban J., Castillo, J. R. "Determination of Glucose in Blood Based on the Intrinsic Fluorescence of Glucose Oxidase." Anal. Chem. 1997 69(8), 1471-1476).

Example 14

Other Monitoring Techniques and Metabolites

Lactate Transport
Lactate transport is monitored by measuring intracellular and extracellular pH using fluorescent SMMRs, as previously described. The xanthene dye BCECF has been used to monitor lactate transport in a number of tissues (see e.g., Carpenter, L. and Halestrap, A. P. 1994 Biochem. J. 304, 751-760). In the present invention this dye is used to monitor both intracellular and extracellular pH. The extracellular pH is monitored to measure variations in physiology within the body that are unrelated to glucose metabolism in the epidermis, but are related to metabolic pH changes in the body. The intracellular pH, as measured, is then corrected using the value of the measured extracellular pH.

Oxidative Phosphorylation

Oxidative phosphorylation can be monitored by NADH fluorescence. This fluorescence is measured in the presence and absence of oxygen. These two measurements yield the rate of oxidative phosphorylation and a measure of the overall metabolism of the cell. The rate of oxidative phosphorylation is dependent on the overall substrate availability to the cell, which requires oxygen. In the absence of oxygen, the overall metabolism is dependent on glycolysis alone.

The oxidative phosphorylation pathway for glucose is determined by measuring oxygen consumption along with the NADH/FAD fluorescence ratio. This ratio has been used in the past to determine the overall reduction potential of the cell. The measurement of the oxygen consumption rate determines the rate of oxidative metabolism in the tissue. The sensitivity of the NADH/FAD fluorescence ratio can be increased by the use of an energy transfer or redox potential measuring dye to amplify overall signal intensity. An example of such a dye suitable for use as an SMMR is rhodamine 123, although other compounds containing conjugated aromatic systems can also be used.

In a preferred embodiment, the amplifying SMMR molecule is positively charged at pH 7 and has a high quantum yield of fluorescence. In a further embodiment, the SMMR molecule has little absorption in the region where NADH absorbs. Excitation of NADH results in energy transfer to the SMMR dye that then fluoresces with efficiency at least ten times greater than that of NADH alone.

Photobleaching

Photobleaching is a process that occurs with virtually all fluorescent dyes. The term is something of a misnomer since it literally means the loss of color as a result of irradiation by light. The loss of color is the result of a photochemical reaction that results in a new chemically distinct compound being formed that does not exhibit the same fluorescence properties as the parent SMMR compound. This new photo-degraded compound will have altered photophysics compared to the parent molecule but its properties are not necessarily loss of color. Photobleaching is a hindrance to continuous fluorescence-based monitoring and is exacerbated by the presence of oxygen, high concentrations of reactive species and high light levels. For this present invention, SMMRs are used that have high quantum yields of fluorescence (which implies that the main process for deactivation of the excited state is fluorescence), and they are excited with the minimum amount of excitation light. Photoreactivity is also reduced by the low oxygen tension in the skin.

Differential Monitoring

The mechanism presented in Scheme 1 (FIG. 17A) for the measurement of glucose requires that the majority of glucose be metabolized by glycolysis because oxidative phosphorylation may also utilize fatty acid metabolites as substrates instead of glucose. Oxidative phosphorylation in skin comprises only ~2% of metabolism and this fraction may be controlled by reducing the oxygen available to the cells, although experimental data suggests that there is little or no effect of oxygen concentration on glycolysis. By performing a differential measurement with and without oxygen, the fraction of glycolytic and oxidative metabolism is determined.

Glycolysis

In tissues that undergoes primarily anaerobic metabolism (i.e., glycolysis) the products of the glycolysis reaction pathway are lactate and adenosine triphosphate (ATP). ATP is synthesized from ADP, the diphosphate analog, and a phosphate. Lactate is generated as a waste product of the pathway. The lactate concentration within the cell is dependent on lactate transport out of the cell and on the rate of glycolysis. The extracellular lactate concentration is dependent on lactate transport and diffusion of lactate into the blood stream. The production of lactate correlates with the intracellular pH. The pH of epidermal tissue, using intra- and extracellular pH sensitive SMMRs, can be used to specifically relate intracellular pH changes to glucose utilization via glycolysis. The use of NMR techniques using phosphorous ($^{31}P$) and proton ($^{1}H$) probes allows the measurement of ATP, phosphate, pH and lactate simultaneously. This technique alone can be used to determine the relationship between glucose concentration and glycolysis. The use of $^{31}P$ NMR is described specifically for measuring the effect of exercise on the levels of ATP, phosphocreatine, and orthophosphate in human forearm muscle. See e.g., G. K. Radda. Science 233: 641 (1986). pH can also be measured in vivo and directly using $^{31}P$ NMR. See e.g., citations in D. G. Gadian et al. In: Biological Applications of Magnetic Resonance, R. G. Shulman, ed., (Academic Press, 1979), p. 475. The $^{31}P$ magnetic resonance technique also provides information on the orthophosphate concentration for glucose metabolism in the Kreb's cycle and/or oxidative phosphorylation pathway. The lactate/pyruvate ratio and the β-hydroxybutyrate/acetoacetate ratios have been used to estimate cytosolic and mitochondrial NADH/NAD(P)H ratios respectively. See e.g., Tischler, M. E., et al., Arch Biochem Biophys, 1977. 184(1): p. 222-36; Poole, R. C. and A. P. Halestrap, Am J Physiol, 1993. 264(4 Pt 1): p. C761-82; Groen, A. K., et al., J Biol Chem, 1983. 258(23): p.14346-53.

Nitric Oxide (NO):

NO has been shown to correlate inversely with glucose concentration. This reactive molecule acts as a vasodilator and interacts with thiol groups. The reaction of NO with hemoglobin has also been monitored in the past using absorption spectroscopy. NO may also be measured using an NO meter using a probe head that is as small as 30 μm.

Scheme 1 (see FIG. 17A) points to the measurement sites required to define the glucose metabolism in epidermis thereby providing complete information for the fate of glucose metabolized in the skin. NO causes physiological effects such as vasodilation and is a reactive material that interacts with thiols and the basement membrane of the dermal/epidermal junction. Direct measurement of NO is possible using commercially available technology. The measurement of NO will be used, if necessary, for final correction of the glucose concentration. The determination of the NO correction follows initial comparisons of blood glucose estimated from fluorescence measurements when compared to blood glucose measured using a reference technique (e.g., YSI Incorporated, PO Box 279, Yellow Springs, Ohio 45387 USA). The change in glucose concentration as affected by NO concentration is described in the equation (23). The use of NO concentration information for final blood glucose correction is also described herein. When required, equations (1-5) of the invention are modified by the addition of an NO term as shown in equation (25). This adjustment accounts for the cases where NO alters the perfusion rate significantly.

$$[Glucose_{blood}] = f\left(\frac{\vartheta_{Reporter}}{\vartheta_{Reference}}\right) \cdot k_i\left(\frac{1}{[NO]}\right) \qquad (25)$$

Where, $$f\left(\frac{\vartheta_{Reporter}}{\vartheta_{Reference}}\right)$$

is the in vivo fluorescence signal ratio of reporter fluorescence to reference (or marker) fluorescence varying with respect to changes in glucose concentration within the measured target tissue; and $k_i$ is the computed weighting factor attributing the effect of NO concentration on the perfusion rate. The factor $k_i$ is computed empirically following comparisons of blood glucose optically determined versus reference values using standard regression methods (see for example H. Mark and J. Workman, Statistics in Spectroscopy, $1^{st}$ Ed., Academic Press, 1991; and $2^{nd}$ Ed., Elsevier Publishers, 2003)

Example 15

Consideration of Blood Glucose Concentration and Fluorescence

Previous work has demonstrated that the lag time between blood glucose levels and non-perturbed epidermis is 2.9 to 4 percent per minute for the differential concentrations (vis-à-vis blood and epidermal glucose concentrations). See, e.g., J. M. Ellison et al. Diabetes Care, June 2002, 25(6), 961-964; B. M. Jensen et al. Scandinavian Journal of Clinical Laboratory Investigation, 1995, 55, 427-432; P. J. Stout, Diabetes Technology & Therapeutics 2001, 3(1), 81-90; C. P. Quinn, Publication 0193-1849/95 The American Physiological Society, E155-E161). In practice, a 5 to 15 minute lag is most often experienced between real-time measured blood glucose levels and glucose levels determined at the keratinocyte/epidermal layers. The fingertip area keratinocyte/epidermal layers are considered ideal due to their high vascularization. The time required for the epidermis to reach an equilibrium with blood glucose at steady-state, dependent on the measurement site, has been reported to be from 25 to 35 minutes. See, e.g. K. Jungheim and T. Koschinsky Diabetes Care, 25(6), 956, 2002; and J. Ellison et al. Diabetes Care, 25(6), 961, 2002.

When blood glucose is rapidly increasing (hyperglycemia) or decreasing (hypoglycemia), the lag time becomes a critical issue for determining the response time for any external, non-invasive blood glucose monitor. Rapid response is required for identifying important health related changes in glucose levels and to avoid critical blood glucose scenarios (i.e., clinically important high or low blood glucose levels). Issues of rapid response are addressed by using elevated temperatures at the measurement site to increase blood flow to these regions. Therefore, in various embodiments, the sensor unit is combined with a regulatable heating element and/or temperature gauge. The sensors are calibrated by comparing actual blood glucose to the sensor output. The temperature is either controlled at the measurement site or compensated for in the final blood glucose estimation. $K_a$ and $\phi_F$ are only slightly temperature dependent. The zero and slope of the sensor calibration are determined by measuring an initial baseline glucose level, and a second glucose level at higher concentration. The sensor calibration is then measured as shown in equation (26):

$$[G] = K_1(\text{sensor response}) + K_0 \qquad (26)$$

The $K_1$ and $K_0$ values are entered into the sensor and the calibration is checked against a reference standard material. The reference standard material is comprised of a matrix that responds to glucose concentration in such a way as to provide primary standard concentration and fluorescence response data. Their relationship is given in equation (27), where A, B, C, and D are comprised of one or more individual analyte measurements or ratios of measurements. The method shown in equations (26) and (27) can be used either for calibration using YSI-determined blood reference data, or without blood reference data via use of equations (13) through (21).

Algorithm:

$$[G] = f([A],[B],[C],[D])^* \qquad (27)$$

*Where [A], [B], [C], and [D] are directly measured using one or more measurement techniques for one or more metabolite signals. Each metabolite signal represents a mechanism for quantitatively measuring intracellular or extracellular glycolysis. The primary fuel for glycolysis is D-glucose combined with low concentrations of other simple sugars, such as galactose and fructose.

EQUIVALENTS

From the foregoing detailed description of the specific embodiments of the invention, it should be apparent that particular novel compositions and methods involving utilizing SMMRs for direct or indirect measurements of metabolic analyte concentrations have been described. Although these particular embodiments have been disclosed herein in detail, this has been done by way of example for purposes of illustration only, and is not intended to be limiting with respect to the scope of the appended claims that follow. In particular, it is contemplated by the inventors that various substitutions, alterations, and modifications may be made as a matter of routine for a person of ordinary skill in the art to the invention without departing from the spirit and scope of the invention as defined by the claims. Indeed, various adaptations and modifications of the invention in addition to those described herein will become apparent to those skilled in the art from the foregoing description and accompanying figures. Such modifications are intended to fall within and be incorporated into the scope of the appended claims.

What is claimed is:

1. An in vivo method for monitoring the concentration of blood glucose, the method comprising:
    applying at least one small molecule metabolic reporter (SMMR) to at least one surface of skin for a predetermined period of time;
    causing penetration of the at least one SMMR to a location having a depth corresponding to the stratum germinativum;
    controlling a temperature at said location, wherein said controller increases blood flow to the dermal layer below said location;
    monitoring a change in the stratum germinativum intracellular concentration of glucose in a metabolic pathway by detecting changes in the at least one SMMR at one or more time points using an optical reader; and
    correlating the change in the stratum germinativum intracellular glucose concentration with in vivo blood glucose levels.

2. The method of claim 1, wherein the at least one SMMR comprises a mitochondrial stain sensitive to membrane potential or chemical gradient.

3. The method of claim 2, wherein the mitochondrial stain is a polycyclic aromatic hydrocarbon dye selected from the group consisting of: rhodamine 123; di-4-ANEPPS; di-8-ANEPPS; DiBAC$_4$(3); RH421; tetramethylrhodamine ethyl ester, perchlorate; tetramethylrhodamine methyl ester, perchlorate; 2-(4-(dimethylamino)styryl)-N-ethylpyridinium iodide; 3,3'-dihexyloxacarbocyanine; 5,5',6,6'-tetrachloro-1, 1',3,3'-tetraethyl-benzimidazolylcarbocyanine chloride; 5,5', 6,6'-tetrachloro-1,1',3,3'-tetraethyl-benzimidazolylcarbocyanine iodide; nonylacridine orange; dihydrorhodamine 123; dihydrorhodamine 123, dihydrochloride salt; xanthene; 2',7'-bis-(2-carboxyethyl)-5-(and -6)-carboxyfluorescein; benzenedicarboxylic acid, 2(or 4)-[10-(dimethylamino)-3-oxo-3-H-benzo[c]xanthene-7-yl]; and iodine dissolved in potassium iodide.

4. The method of claim 1, wherein the at least one SMMR comprises a dye or stain that transfers energy from a molecule generated as a result of an oxidative metabolic pathway and that has a stoichiometric or substantially stoichiometric relationship with glucose concentration.

5. The method of claim 1, wherein the at least one SMMR comprises a dye selected from the group consisting of: coumarin; anthraquinones; cyanine dyes; azo dyes; xanthene dyes; arylmethine dyes; and ruthenium bipyridyl complexes.

6. The method of claim 1, wherein the at least one SMMR comprises a protein labeled fluorophore.

7. The method of claim 6, wherein the protein labeled fluorophore is Glucose Oxidase-Labeled Fluorophore (GO-LF) or Glucose Oxidase-Intercalated Fluorophore (GO-IF).

8. The method of claim 1, wherein the at least one SMMR comprises a protein comprising a photooxidizable cofactor.

9. The method of claim 8, wherein the protein comprising a photooxidizable cofactor is Glucose Oxidase (GOx) with a flavin adenine dinucleotide (FAD) in the triplet state (GOx-$^3$FAD*).

10. The method of claim 1, wherein monitoring the change in the stratum germinativum intracellular glucose concentration comprises detecting radiation at least one wavelength above 350 nm.

11. The method of claim 1, wherein the at least one SMMR is formulated as a cream, emulsion, ointment, oil, disposable gel film patch, reservoir device or paint.

12. The method of claim 1, wherein the at least one SMMR penetrates within the skin using at least one technique selected from the group consisting of: electroporation, solvent transport, tattooing, injecting, microneedle delivery, and passive transport.

13. The method of claim 1, wherein the monitoring comprises quantification of the change in fluorescence or absorption using fluorescence or absorption spectroscopy.

14. The method of claim 1, wherein the at least one SMMR penetrates within the skin using microneedle delivery.

15. An in vivo method for measuring blood glucose levels, said in vivo method comprising controlling a temperature at a population of stratum germinativum cells to increase blood flow to a dermal layer below said stratum germinativum cells, and monitoring intracellular glucose concentration in the population of stratum germinativum cells, wherein the monitoring comprises measuring the fluorescence spectrum emitted by at least one small molecule metabolic reporter (SMMR), wherein at least one fluorescence spectrum emitted by the at least one SMMR is stoichiometrically related to the glucose intracellular concentration in the population of stratum germinativum cells, whereby analyzing the relatedness provides the in vivo blood glucose level.

16. The method of claim 15, wherein the population of stratum germinativum cells has a predominantly glycolytic metabolism or can be induced to have a glycolytic metabolism.

17. The method of claim 16, wherein the population of stratum germinativum cells is located in the epidermis, wherein the epidermis comprises a dynamic, metabolically homogeneous, and homeostatic population of cells.

18. The method of claim 16, wherein the population of stratum germinativum cells having a glycolytic metabolism comprise live keratinocytes.

19. The method of claim 15, wherein the intracellular glucose concentration is monitored in the population of stratum germinativum cells via measurement of one or more specific metabolite or analyte of the glycolytic pathway that has a stoichiometric or substantially stoichiometric relationship with glucose concentration.

20. The method of claim 15, wherein the monitoring of intracellular glucose concentration in the population of stratum germinativum cells, comprises measuring a physico-chemical parameter that is related to the glycolytic pathway, wherein said physic-chemical parameter comprises a stoichiometric or substantially stoichiometric relationship with glucose concentration.

21. The method of claim 15, wherein the population of stratum germinativum cells comprises a predominantly oxidative metabolism or can be induced to comprise a metabolism predominantly based on oxidative phosphorylation.

22. The method of claim 21, wherein the monitoring of intracellular glucose concentration in the population of stratum germinativum cells, comprises measuring a metabolite or analyte that is generated as a result of an oxidative metabolic pathway, wherein said metabolite or analyte comprises a stoichiometric or substantially stoichiometric relationship with glucose concentration.

23. The method of claim 21, wherein the monitoring of intracellular glucose concentration in the population of stratum germinativum cells, comprises measuring a physico-chemical parameter that is generated as a result of an oxidative metabolic pathway and that comprises a stoichiometric or substantially stoichiometric relationship with glucose concentration.

24. A noninvasive method for monitoring in vivo blood glucose levels, the method comprising:
applying at least one small molecule metabolic reporter (SMMR) to at least one surface of skin for a predetermined period of time;
causing penetration of the at least one SMMR to a location corresponding to the stratum germinativum;
contacting the at least one SMMR with one or more metabolites or analytes indicative of stratum germinativum intracellular glucose concentration;
controlling a temperature at said location, wherein said controlling increases blood flow to the dermal layer below said location;
monitoring a change in the stratum germinativum intracellular glucose concentration by detecting changes in the at least one SMMR using an optical reader, and
correlating the change in the stratum germinativum intracellular glucose concentration with in vivo blood glucose levels.

25. The method of claim 24, wherein the at least one small molecule metabolic reporter is selected from the group consisting of a fluorophore, a protein labeled fluorophore, a protein comprising a photooxidizable cofactor, a protein comprising an intercalated fluorophore, a mitochondrial vital stain or dye, a dye exhibiting one or more of a redox potential, a membrane localizing dye, a dye comprising energy transfer properties, a pH indicating dye, a coumarin dye, an anthraquinone dye, a cyanine dye, an azo dye, a xanthene dye, an arylmethine dye, and a ruthenium bipyridyl complex dye.

26. The method of claim 25, wherein the protein labeled fluorophore is Glucose Oxidase-Labeled Fluorophore (GO-LF) and the one or more metabolites is glucose.

27. The method of claim 25, wherein the protein comprising a photooxidizable cofactor is Glucose Oxidase (GOx) with a flavin adenine dinucleotide (FAD) in the triplet state (GOx $^3$FAD*).

28. The method of claim 25, wherein the mitochondrial vital stain or dye is a polycyclic aromatic hydrocarbon dye selected from the group consisting of: Rhodamine 123; Di-4-ANEPPS; Di-8-ANEPPS; DiBAC$_4$(3); RH421; Tetramethylrhodamine ethyl ester, perchlorate; Tetramethylrhodamine methyl ester, perchlorate; 2-(4-(dimethylamino)styryl)-N-ethylpyridinium iodide; 3,3'-Dihexyloxacarbocyanine; 5,5',6,6'-tetrachloro-1,1',3,3'-tetraethyl-benzimidazolylcarbocyanine chloride; 5,5',6,6'-tetrachloro-1,1',3,3'-tetraethyl-benzimidazolylcarbocyanine iodide; Nonylacridine Orange; Dihydrorhodamine 123; Dihydrorhodamine 123, dihydrochloride salt; xanthene; 2',7'-bis-(2-carboxyethyl)-5-(and -6)-carboxyfluorescein; benzenedicarboxylic acid, 2(or 4)-[10-(dimethylamino)-3-oxo-3-H-benzo[c]xanthene-7-yl]; and iodine dissolved in potassium iodide.

29. The method of claim 25, where monitoring the change in stratum germinativum intracellular glucose concentration comprises measuring at least one spectral emission at a wavelength above 450 nm.

30. The method of claim 24, wherein the one or more metabolites or analytes are selected from the group consisting of glucose, lactate, H$^+$, Ca$^{2+}$, Mg$^{2+}$, Na$^+$, K$^+$, ATP, ADP, P$_i$, glycogen, pyruvate, NAD(P)+, NAD(P)H, FAD, FADH$_2$, and O$_2$.

31. A method for determining in vivo blood glucose concentration, comprising the steps of:
performing an instrument response measurement on a calibration target and recording the response data;
applying a mixture comprising at least one SMMR to the skin in a first controlled area such that the at least one SMMR resides in the stratum germinativum layer of the skin;
applying a second mixture comprising at least one SMMR to the skin in a second controlled area;
perturbing the second controlled area such that one or more extreme changes at the second controlled area are achieved;
performing a calibration measurement on the perturbed area and recording the calibration data;
performing a background measurement on an area of skin that has no SMMR and recording this background data;
controlling a temperature at the first controlled area, wherein said controlling increases blood flow to a dermal layer below the first controlled area;
illuminating the first controlled area with light and performing a first measurement on the first controlled area;
detecting at least one wavelength spectrum of light reflected back from the first controlled area;
performing at least a second measurement on the first controlled area at wavelengths suitable for each SMMR present;
calculating at least one parameter from the response data to normalize the background data, calibration data and measurement data for the response using a spectrometer;
calculating at least one parameter from the background data to correct the calibration data and measurement data for emission, absorption and scattering properties of the tissue; and
calculating at least one stratum germinativum intracellular glucose parameter from the calibration data to relate the measurement data to the blood glucose concentration;
thereby determining in vivo blood glucose concentration.

32. The method of claim 31, wherein the one or more extreme changes is a change in concentration of a metabolite or analyte between a zero or near zero concentration and a saturation level or near saturation level concentration.

33. The method of claim 31, wherein the mixture comprising at least one SMMR penetrates within the stratum germinativum layer of skin using microneedle delivery.

* * * * *